US012655219B2

(12) United States Patent
Pan et al.

(10) Patent No.: US 12,655,219 B2
(45) Date of Patent: Jun. 16, 2026

(54) ANTI-CTLA-4 ANTIBODY AND USE THEREOF

(71) Applicant: SHANGHAI JUNSHI BIOSCIENCES CO., LTD., Shanghai (CN)

(72) Inventors: Zhiwei Pan, Suzhou (CN); Jian Yao, Shanghai (CN); Jing Zhang, Suzhou (CN); Yuehua Zhou, Suzhou (CN); Hongchuan Liu, Suzhou (CN); Hai Wu, Shanghai (CN); Sheng Yao, Shanghai (CN); Hui Feng, Suzhou (CN)

(73) Assignee: SHANGHAI JUNSHI BIOSCIENCES CO., LTD., Shanghai (CN)

( * ) Notice: Subject to any disclaimer, the term of this patent is extended or adjusted under 35 U.S.C. 154(b) by 661 days.

(21) Appl. No.: 18/016,643

(22) PCT Filed: Jul. 21, 2021

(86) PCT No.: PCT/CN2021/107707
§ 371 (c)(1),
(2) Date: Jan. 17, 2023

(87) PCT Pub. No.: WO2022/017428
PCT Pub. Date: Jan. 27, 2022

(65) Prior Publication Data
US 2023/0295301 A1     Sep. 21, 2023

(30) Foreign Application Priority Data

Jul. 21, 2020     (CN) ......................... 202010708105.8

(51) Int. Cl.
*C07K 16/28*     (2006.01)
*A61K 39/00*     (2006.01)
*A61P 35/00*     (2006.01)

(52) U.S. Cl.
CPC .......... *C07K 16/2818* (2013.01); *A61K 39/00* (2013.01); *A61P 35/00* (2018.01); *C07K 2317/20* (2013.01); *C07K 2317/21* (2013.01); *C07K 2317/24* (2013.01); *C07K 2317/622* (2013.01); *C07K 2317/76* (2013.01)

(58) Field of Classification Search
None
See application file for complete search history.

(56) References Cited

U.S. PATENT DOCUMENTS 7,696,322 B2     4/2010   Bleck et al.

FOREIGN PATENT DOCUMENTS

| | | | |
|---|---|---|---|
| CN | 101074264 A | 11/2007 | |
| CN | 102134276 A | 7/2011 | |
| CN | 104292334 A | 1/2015 | |
| CN | 110248961 A | 9/2019 | |
| WO | WO-2017/087870 A1 | 5/2017 | |
| WO | WO-2018/025178 A1 | 2/2018 | |
| WO | WO-2018106862 A1 * | 6/2018 | .............. A61P 35/04 |
| WO | WO-2019/174603 A1 | 9/2019 | |

OTHER PUBLICATIONS

Miner et al. Science Translational Medicine. 9(375): aah3238; Published: Feb. 1, 2017 (Year: 2017).*
Pitot et al. Cancer. 73(3): 962-970; Published: Aug. 1, 1993 (Year: 1993).*
Hanahan et al. Cell. 144(5): 646-674; Published: Mar. 4, 2011 (Year: 2011).*
International Search Report for International Application No. PCT/CN2021/107707 mailed Oct. 20, 2021 (English Translation attached) (10 pages).
International Preliminary Report on Patentability for International Application PCT/CN2021/107707 issued Jan. 24, 2023 (7 pages).

* cited by examiner

*Primary Examiner* — Juliet C Switzer
*Assistant Examiner* — Katherine Ann Holtzman
(74) *Attorney, Agent, or Firm* — Burr & Forman

(57)     ABSTRACT

An antibody specifically binding to CTLA-4 or an antigen-binding fragment thereof, and a composition comprising same. Also provided are a nucleic acid molecule encoding the antibody or an antigen-binding fragment thereof, a vector and a host cell for expressing the antibody or an antigen-binding fragment thereof, and therapeutic and diagnostic methods and the use of the antibody or an antigen-binding fragment thereof.

17 Claims, 22 Drawing Sheets

Specification includes a Sequence Listing.

| | JS007-1 | JS007-3 | JS007-11 | JS007-15 | JS007-20 | Ipilimumab |
|---|---|---|---|---|---|---|
| EC50 | ~ 788312 | 17.23 | ~ 4.008e+006 | 19.72 | 12.88 | 17.71 |

| | JS007-1 | JS007-3 | JS007-11 | JS007-15 | JS007-20 | Ipilimumab |
|---|---|---|---|---|---|---|
| EC50 | 4181 | 249.4 | ~ 4231 | 189.4 | 486.1 | 558.2 |

| | JS007-3 | JS007-15 | JS007-20 | Ipilimumab |
|---|---|---|---|---|
| IC50 | 189.7 | 189.7 | 186.6 | 460.6 |

| | JS007-3 | JS007-15 | JS007-20 | Ipilimumab |
|---|---|---|---|---|
| IC50 | 0.6986 | 0.398 | 1.211 | 1.683 |

| | JS007-3 | JS007-15 | JS007-20 | Ipilimumab |
|---|---|---|---|---|
| IC50 | 0.196 | 0.0816 | 0.2528 | 0.1845 |

| | JS007-3 | JS007-15 | JS007-20 | Ipilimumab |
|---|---|---|---|---|
| EC50 | 0.903 | 0.5182 | ~ 0.2573 | 0.5073 |

FIG. 9

Humanized antibody number

Relative binding activity, %

FIG. 10

| | HXT hCTLA4 his | hCTLA4 Nhis P27A | hCTLA4 Nhis G28A | hCTLA4 Nhis K29A | hCTLA4 Nhis T31A |
|---|---|---|---|---|---|
| EC50 | 13.57 | 33.3 | NA | 46.71 | 13.56 |

ANTI-CTLA-4 ANTIBODY AND USE THEREOF

SEQUENCE LISTING

The instant application contains a Sequence Listing which has been submitted electronically in TXT format and is hereby incorporated by reference in its entirety. Said TXT copy, created on Jan. 16, 2026, is named "51910-003001_Sequence_Listing_1_16_26_ST25" and is 66,026 bytes in size.

TECHNICAL FIELD

The present invention provides an antibody or an antigen-binding fragment thereof specifically binding to CTLA-4 and a composition comprising the same. Also provided are a nucleic acid molecule encoding the antibody or the antigen-binding fragment thereof disclosed herein, a vector and a host cell for expressing the antibody or the antigen-binding fragment thereof disclosed herein, and therapeutic and diagnostic methods and uses of the antibody or the antigen-binding fragment thereof disclosed herein.

BACKGROUND

Cytotoxic T lymphocyte-associated protein 4 (CTLA4 or CTLA-4), also known as CD152 (cluster of differentiation 152), is a transmembrane protein encoded by the CTLA-4 gene, which is located on human chromosome 2 at 2q33. CTLA-4 is a member of the immunoglobulin superfamily, consisting of an extracellular V-region, a transmembrane region, and a cytoplasmic region. CTLA-4 is homologous with the co-stimulatory molecule receptor CD28 on the surface of a T cell. They compete for binding to their receptors B7-1 (CD80) and B7-2 (CD86); such receptors are expressed primarily on the surface of an antigen-presenting cell. CTLA-4 binds with higher affinity to CD80 and CD86 than CD28 and is, therefore, able to compete and block CD28-mediated activation. CTLA-4 is typically expressed on the surfaces of regulatory T cells (Tregs) and activated regular T cells. After binding to B7 molecules, it inhibits the activation of T cells, participates in the negative regulation of immune responses, acts as an immune checkpoint and down-regulates immune responses. Therefore, CTLA-4 plays a crucial role in immune regulation.

The activation of T cells requires two signals' stimulation. The first signal arises from the specific binding of the T cell receptor (TCR) to the antigen peptide-MHC complex on the surface of an antigen-presenting cell (APC). The second signaling pathway requires the participation of co-stimulatory molecules (such as CD28); when CD28 binds to B7-1/B7-2 (CD80/CD86), it can further activate T cells, promoting their maturation and proliferation. Current research reveals that CTLA-4 down-regulates T cell function during immune responses in several ways. First, CTLA-4 can competitively block the transmission of the co-stimulatory signal of CD28 and CD80/86 through its high affinity for CD80/CD86, thereby inhibiting T cell proliferation and reducing IL-2 secretion. Second, CTLA-4 can reduce CD28-involving T cell activation by reducing the expression level of CD80/CD86 on antigen-presenting cells (APCs) or by removing CD80/CD86 molecules from the surfaces of antigen-presenting cells (APCs) through trans-endocytosis. Third, CTLA-4 can inhibit TCR signaling by mediating the binding of dendritic cells to CD80/CD86 and inducing the expression of tryptophan-degrading enzyme IDO. Further, CTLA-4 can also inhibit APC signaling and TCR signaling by recruiting inhibitory molecules so they bind to immunological synapses, inducing the production of regulatory cytokines.

The CTLA-4's blocking has been shown in many studies to induce tumor regression. Anti-CTLA-4 antibodies can effectively and specifically inhibit cellular and humoral immune responses in vivo and in vitro, having significant therapeutic effects on transplant rejection and various autoimmune diseases without causing many toxic side effects.

Although CTLA-4 monoclonal antibody drugs ipilimumab (Bristol-Myers Squibb) and tremelimumab (AstraZeneca) are currently available as treatments for some cancers and are tested for other indications for anti-cancer therapy, there is still a need for novel anti-CTLA-4 antibodies which are improvements over the known antibodies in all respects including activity.

SUMMARY

The present invention provides an anti-CTLA-4 antibody or an antigen-binding fragment thereof, which has the advantage of having high affinity, high specificity etc., for human CTLA-4. The anti-CTLA-4 antibody or the antigen-binding fragment thereof provided herein can be used as an independent therapy or in combination with other therapies and/or other anti-cancer pharmaceutical agents to treat, for example, cancers.

In one aspect, the present invention provides an anti-CTLA-4 antibody or an antigen-binding fragment thereof, which comprises a heavy chain variable region and/or a light chain variable region, wherein the heavy chain variable region comprises:

(I) HCDR1, HCDR2 and HCDR3 whose amino acid sequences are set forth in SEQ ID NO: 1, SEQ ID NO: 2 and SEQ ID NO: 3, respectively; or HCDR1, HCDR2 and HCDR3 which differ from the amino acid sequences set forth in SEQ ID NO: 1, SEQ ID NO: 2 and SEQ ID NO: 3 respectively by 1, 2 or 3 amino acids, wherein preferably, the HCDR2 which differs from the amino acid sequence set forth in SEQ ID NO: 2 by 1, 2 or 3 amino acids is SEQ ID NO: 37; preferably, the HCDR3 which differs from the amino acid sequence set forth in SEQ ID NO: 3 by 1, 2 or 3 amino acids is SEQ ID NO: 38; or (II) HCDR1, HCDR2 and HCDR3 whose amino acid sequences are set forth in SEQ ID NO: 7, SEQ ID NO: 8 and SEQ ID NO: 9, respectively; or HCDR1, HCDR2 and HCDR3 which differ from the amino acid sequences set forth in SEQ ID NO: 7, SEQ ID NO: 8 and SEQ ID NO: 9 respectively by 1, 2 or 3 amino acids; or (III) HCDR1, HCDR2 and HCDR3 whose amino acid sequences are set forth in SEQ ID NO: 13, SEQ ID NO: 14 and SEQ ID NO: 15, respectively; or HCDR1, HCDR2 and HCDR3 which differ from the amino acid sequences set forth in SEQ ID NO: 13, SEQ ID NO: 14 and SEQ ID NO: 15 respectively by 1, 2 or 3 amino acids; or (IV) HCDR1, HCDR2 and HCDR3 whose amino acid sequences are set forth in SEQ ID NO: 19, SEQ ID NO: 20 and SEQ ID NO: 21, respectively; or HCDR1, HCDR2 and HCDR3 which differ from the amino acid sequences set forth in SEQ ID NO: 19, SEQ ID NO: 20 and SEQ ID NO: 21 respectively by 1, 2 or 3 amino acids, wherein preferably, the HCDR2 which differs from the amino acid sequence set forth in SEQ ID NO: 20 by 1, 2 or 3 amino acids is SEQ ID NO: 39; or (V) HCDR1, HCDR2 and HCDR3 whose amino acid sequences are set forth in SEQ ID NO: 22, SEQ ID NO: 23 and SEQ ID NO: 24, respectively; or HCDR1, HCDR2 and HCDR3 which differ from the amino acid sequences set forth in SEQ ID NO: 22, SEQ ID NO: 23 and SEQ ID NO: 24 respectively by 1, 2 or 3 amino acids;

the light chain variable region comprises:

(I) LCDR1, LCDR2 and LCDR3 whose amino acid sequences are set forth in SEQ ID NO: 4, SEQ ID NO: 5 and SEQ ID NO: 6, respectively; or LCDR1, LCDR2 and LCDR3 which differ from the amino acid sequences set forth in SEQ ID NO: 4, SEQ ID NO: 5 and SEQ ID NO: 6 respectively by 1, 2 or 3 amino acids; or (II) LCDR1, LCDR2 and LCDR3 whose amino acid sequences are set forth in SEQ ID NO: 10, SEQ ID NO: 11 and SEQ ID NO: 12, respectively; or LCDR1, LCDR2 and LCDR3 which differ from the amino acid sequences set forth in SEQ ID NO: 10, SEQ ID NO: 11 and SEQ ID NO: 12 respectively by 1, 2 or 3 amino acids; or (III) LCDR1, LCDR2 and LCDR3 whose amino acid sequences are set forth in SEQ ID NO: 16, SEQ ID NO: 17 and SEQ ID NO: 18, respectively; or LCDR1, LCDR2 and LCDR3 which differ from the amino acid sequences set forth in SEQ ID NO: 16, SEQ ID NO: 17 and SEQ ID NO: 18 respectively by 1, 2 or 3 amino acids, wherein preferably, the LCDR1 which differs from the amino acid sequence set forth in SEQ ID NO: 16 by 1, 2 or 3 amino acids is SEQ ID NO: 40 or 41; or (IV) LCDR1, LCDR2 and LCDR3 whose amino acid sequences are set forth in SEQ ID NO: 25, SEQ ID NO: 26 and SEQ ID NO: 27, respectively; or LCDR1, LCDR2 and LCDR3 which differ from the amino acid sequences set forth in SEQ ID NO: 25, SEQ ID NO: 26 and SEQ ID NO: 27 respectively by 1, 2 or 3 amino acids.

In some embodiments, the antibody or the antigen-binding fragment thereof comprises a heavy chain variable region and/or a light chain variable region, wherein the heavy chain variable region comprises:

(I) HCDR1, HCDR2 and HCDR3 whose amino acid sequences are set forth in SEQ ID NO: 1. SEQ ID NO: 2 and SEQ ID NO: 3, respectively; or (II) HCDR1, HCDR2 and HCDR3 whose amino acid sequences are set forth in SEQ ID NO: 7. SEQ ID NO: 8 and SEQ ID NO: 9, respectively; or (III) HCDR1, HCDR2 and HCDR3 whose amino acid sequences are set forth in SEQ ID NO: 13, SEQ ID NO: 14 and SEQ ID NO: 15, respectively; or (IV) HCDR1, HCDR2 and HCDR3 whose amino acid sequences are set forth in SEQ ID NO: 19, SEQ ID NO: 20 and SEQ ID NO: 21, respectively; or (V) HCDR1, HCDR2 and HCDR3 whose amino acid sequences are set forth in SEQ ID NO: 22, SEQ ID NO: 23 and SEQ ID NO: 24, respectively; or (VI) HCDR1, HCDR2 and HCDR3 whose amino acid sequences are set forth in SEQ ID NO: 1, SEQ ID NO: 37 and SEQ ID NO: 3, respectively; or (VII) HCDR1, HCDR2 and HCDR3 whose amino acid sequences are set forth in SEQ ID NO: 1. SEQ ID NO: 37 and SEQ ID NO: 38, respectively; or (VIII) HCDR1, HCDR2 and HCDR3 whose amino acid sequences are set forth in SEQ ID NO: 1. SEQ ID NO: 2 and SEQ ID NO: 38, respectively; or (IX) HCDR1, HCDR2 and HCDR3 whose amino acid sequences are set forth in SEQ ID NO: 19, SEQ ID NO: 39 and SEQ ID NO: 21, respectively;

and/or the light chain variable region comprises:

(I) LCDR1, LCDR2 and LCDR3 whose amino acid sequences are set forth in SEQ ID NO: 4, SEQ ID NO: 5 and SEQ ID NO: 6, respectively: or (II) LCDR1, LCDR2 and LCDR3 whose amino acid sequences are set forth in SEQ ID NO: 10, SEQ ID NO: 11 and SEQ ID NO: 12, respectively; or (III) LCDR1, LCDR2 and LCDR3 whose amino acid sequences are set forth in SEQ ID NO: 16, SEQ ID NO: 17 and SEQ ID NO: 18, respectively; or (IV) LCDR1, LCDR2 and LCDR3 whose amino acid sequences are set forth in SEQ ID NO: 25, SEQ ID NO: 26 and SEQ ID NO: 27, respectively; or (V) LCDR1, LCDR2 and LCDR3 whose amino acid sequences are set forth in SEQ ID NO: 40, SEQ ID NO: 17 and SEQ ID NO: 18, respectively; or (VI) LCDR1, LCDR2 and LCDR3 whose amino acid sequences are set forth in SEQ ID NO: 41, SEQ ID NO: 17 and SEQ ID NO: 18, respectively.

In some embodiments, the antibody or the antigen-binding fragment thereof disclosed herein comprises a heavy chain variable region and a light chain variable region, wherein the heavy chain variable region comprises HCDR1, HCDR2 and HCDR3, wherein HCDR1 is selected from the amino acid sequences set forth in SEQ ID NOs: 1 and 19; HCDR2 is selected from an amino acid sequence set forth in any one of SEQ ID NOs: 2, 20, 37 and 39; HCDR3 is selected from an amino acid sequence set forth in any one of SEQ ID NOs: 3, 21 and 38; and the light chain variable region comprises LCDR1, LCDR2 and LCDR3, wherein an amino acid sequence of LCDR1 is set forth in SEQ ID NO: 72; an amino acid sequence of LCDR2 is set forth in SEQ ID NO: 17; an amino acid sequence of LCDR3 is set forth in SEQ ID NO: 18; wherein the SEQ ID NO: 72 has an amino acid sequence set forth in the following general formula: LCDR1: XASQNVGTYVA, wherein X is selected from K, R and Q.

In some embodiments, the antibody or the antigen-binding fragment thereof disclosed herein comprises a heavy chain variable region and/or a light chain variable region, wherein, the heavy chain variable region comprises:

(I) HCDR1, HCDR2 and HCDR3 whose amino acid sequences are set forth in SEQ ID NO: 1, SEQ ID NO: 2 and SEQ ID NO: 3, respectively; or (II) HCDR1, HCDR2 and HCDR3 whose amino acid sequences are set forth in SEQ ID NO: 1, SEQ ID NO: 37 and SEQ ID NO: 3, respectively; or (III) HCDR1, HCDR2 and HCDR3 whose amino acid sequences are set forth in SEQ ID NO: 1. SEQ ID NO: 2 and SEQ ID NO: 38, respectively; or (IV) HCDR1, HCDR2 and HCDR3 whose amino acid sequences are set forth in SEQ ID NO: 1, SEQ ID NO: 37 and SEQ ID NO: 38, respectively; or (V) HCDR1, HCDR2 and HCDR3 whose amino acid sequences are set forth in SEQ ID NO: 19, SEQ ID NO: 20 and SEQ ID NO: 21, respectively; or (VI) HCDR1, HCDR2 and HCDR3 whose amino acid sequences are set forth in SEQ ID NO: 19. SEQ ID NO: 39 and SEQ ID NO: 21, respectively;

the light chain variable region comprises:

(I) LCDR1, LCDR2 and LCDR3 whose amino acid sequences are set forth in SEQ ID NO: 16, SEQ ID NO: 17 and SEQ ID NO: 18, respectively; or (II) LCDR1, LCDR2 and LCDR3 whose amino acid sequences are set forth in SEQ ID NO: 40, SEQ ID NO: 17 and SEQ ID NO: 18, respectively; or (III) LCDR1, LCDR2 and LCDR3 whose amino acid sequences are set forth in SEQ ID NO: 41, SEQ ID NO: 17 and SEQ ID NO: 18, respectively.

In some embodiments, the antibody or the antigen-binding fragment thereof comprises:

(I) a heavy chain variable region, comprising HCDR1, HCDR2 and HCDR3 whose amino acid sequences are set forth in SEQ ID NO: 1, SEQ ID NO: 2 and SEQ ID NO: 3, respectively; and a light chain variable region, comprising LCDR1, LCDR2 and LCDR3 whose amino acid sequences are set forth in SEQ ID NO: 4, SEQ ID NO: 5 and SEQ ID NO: 6, respectively; or (II) a heavy chain variable region, comprising HCDR1, HCDR2 and HCDR3 whose amino acid sequences are set forth in SEQ ID NO: 7, SEQ ID NO: 8 and SEQ ID NO: 9, respectively; and a light chain variable region, comprising LCDR1, LCDR2 and LCDR3 whose amino acid sequences are set forth in SEQ ID NO: 10, SEQ ID NO: 11 and SEQ ID NO: 12, respectively; or (III) a heavy chain variable region, comprising HCDR1, HCDR2 and HCDR3 whose amino acid sequences are set forth in SEQ ID NO: 13, SEQ ID NO: 14 and SEQ ID NO: 15, respectively; and a light chain variable region, comprising LCDR1, LCDR2 and LCDR3 whose amino acid sequences are set forth in SEQ ID NO: 16, SEQ ID NO: 17 and SEQ ID NO: 18, respectively; or (IV) a heavy chain variable region, comprising HCDR1, HCDR2 and HCDR3 whose amino acid sequences are set forth in SEQ ID NO: 19, SEQ ID NO: 20 and SEQ ID NO: 21, respectively; and a light chain variable region, comprising LCDR1, LCDR2 and LCDR3 whose amino acid sequences are set forth in SEQ ID NO: 16, SEQ ID NO: 17 and SEQ ID NO: 18, respectively; or (V) a heavy chain variable region, comprising HCDR1, HCDR2 and HCDR3 whose amino acid sequences are set forth in SEQ ID NO: 22, SEQ ID NO: 23 and SEQ ID NO: 24, respectively; and a light chain variable region, comprising LCDR1, LCDR2 and LCDR3 whose amino acid sequences are set forth in SEQ ID NO: 25, SEQ ID NO: 26 and SEQ ID NO: 27, respectively; or (VI) a heavy chain variable region, comprising HCDR1, HCDR2 and HCDR3 whose amino acid sequences are set forth in SEQ ID NO: 1, SEQ ID NO: 2 and SEQ ID NO: 3, respectively; and a light chain variable region, comprising LCDR1, LCDR2 and LCDR3 whose amino acid sequences are set forth in SEQ ID NO: 16, SEQ ID NO: 17 and SEQ ID NO: 18, respectively; or (VII) a heavy chain variable region, comprising HCDR1, HCDR2 and HCDR3 whose amino acid sequences are set forth in SEQ ID NO: 19, SEQ ID NO: 39 and SEQ ID NO: 21, respectively; and a light chain variable region, comprising LCDR1, LCDR2 and LCDR3 whose amino acid sequences are set forth in SEQ ID NO: 40, SEQ ID NO: 17 and SEQ ID NO: 18, respectively; or (VIII) a heavy chain variable region, comprising HCDR1, HCDR2 and HCDR3 whose amino acid sequences are set forth in SEQ ID NO: 1, SEQ ID NO: 37 and SEQ ID NO: 38, respectively; and a light chain variable region, comprising LCDR1, LCDR2 and LCDR3 whose amino acid sequences are set forth in SEQ ID NO: 40, SEQ ID NO: 17 and SEQ ID NO: 18, respectively; or (IX) a heavy chain variable region, comprising HCDR1, HCDR2 and HCDR3 whose amino acid sequences are set forth in SEQ ID NO: 19, SEQ ID NO: 20 and SEQ ID NO: 21, respectively; and a light chain variable region, comprising LCDR1, LCDR2 and LCDR3 whose amino acid sequences are set forth in SEQ ID NO: 40, SEQ ID NO: 17 and SEQ ID NO: 18, respectively.

In some embodiments, the antibody or the antigen-binding fragment thereof comprises a heavy chain variable region and a light chain variable region, wherein (I) the heavy chain variable region comprises an amino acid sequence set forth in any one of SEQ ID NOS: 28, 30, 32, 34 and 35, or an amino acid sequence having at least 95%, 96%, 97%, 98% or 99% sequence identity to an amino acid sequence set forth in any one of SEQ ID NOs: 28, 30, 32, 34 and 35; and the light chain variable region comprises an amino acid sequence set forth in any one of SEQ ID NOs: 29, 31, 33 and 36, or an amino acid sequence having at least 95%, 96%, 97%, 98% or 99% sequence identity to an amino acid sequence set forth in any one of SEQ ID NOs: 29, 31, 33 and 36; or (II) a heavy chain variable region whose amino acid sequence is set forth in SEQ ID NO: 28 and a light chain variable region whose amino acid sequence is set forth in SEQ ID NO: 29; or (III) a heavy chain variable region whose amino acid sequence is set forth in SEQ ID NO: 30 and a light chain variable region whose amino acid sequence is set forth in SEQ ID NO: 31; or (IV) a heavy chain variable region whose amino acid sequence is set forth in SEQ ID NO: 32 and a light chain variable region whose amino acid sequence is set forth in SEQ ID NO: 33; or (IV) a heavy chain variable region whose amino acid sequence is set forth in SEQ ID NO: 34 and a light chain variable region whose amino acid sequence is set forth in SEQ ID NO: 33; or (VI) a heavy chain variable region whose amino acid sequence is set forth in SEQ ID NO: 35 and a light chain variable region whose amino acid sequence is set forth in SEQ ID NO: 36.

In some embodiments, the antibody or the antigen-binding fragment thereof comprises a heavy chain variable region and a light chain variable region, wherein the heavy chain variable region comprises an amino acid sequence set forth in any one of SEQ ID NOs: 28 and 34 or a variant thereof, and the light chain variable region comprises the amino acid sequence set forth in SEQ ID NO: 33 or a variant thereof, wherein the variant comprises:

1, 2, 3, 4, 5, 6, 7, 8, 9 or 10 amino acid differences in the heavy chain variable region whose amino acid sequence is set forth in any one of SEQ ID NOs: 28 and 34, and/or 1, 2, 3, 4, 5, 6, 7, 8, 9 or 10 amino acid differences in the light chain variable region whose amino acid sequence is set forth in SEQ ID NO: 33.

In some embodiments, the antibody or the antigen-binding fragment thereof comprises:

(I) a heavy chain variable region, comprising an amino acid sequence set forth in any one of SEQ ID NOS: 42, 43, 44, 45, 46, 47 and 48, or an amino acid sequence having at least 95%, 96%, 97%, 98% or 99% sequence identity to an amino acid sequence set forth in any one of SEQ ID NOs: 42, 43, 44, 45, 46, 47 and 48; and a light chain variable region, comprising an amino acid sequence set forth in any one of SEQ ID NOs: 54, 55, 56, 57, 58, 59, 60, 61 and 62, or an amino acid sequence having at least 95%, 96%, 97%, 98% or 99% sequence identity to an amino acid sequence set forth in any one of SEQ ID NOs: 54, 55, 56, 57, 58, 59, 60, 61 and 62; or (II) a heavy chain variable region, comprising an amino acid sequence set forth in any one of SEQ ID NOS: 49, 50, 51, 52 and 53, or an amino acid sequence having at least 95%, 96%, 97%, 98% or 99% sequence identity to an amino acid sequence set forth in any one of SEQ ID NOs: 49, 50, 51, 52 and 53; and a light chain variable region, comprising an amino acid sequence set forth in any one of SEQ ID NOs: 54, 55, 56, 57, 58, 59, 60, 61 and 62, or an amino acid sequence having at least 95%, 96%, 97%, 98% or 99% sequence identity to an amino acid sequence set forth in any one of SEQ ID NOs: 54, 55, 56, 57, 58, 59, 60, 61 and 62; or (III) a heavy chain variable region whose amino acid sequence is set forth in SEQ ID NO: 50 and a light chain variable region whose amino acid sequence is set forth in SEQ ID NO: 54, 55, 56 or 57; or (IV) a heavy chain variable region whose amino acid sequence is set forth in SEQ ID NO: 51 and a light chain variable region whose amino acid sequence is set forth in SEQ ID NO: 54 or 55; or (V) a heavy chain variable region whose amino acid sequence is set forth in SEQ ID NO: 46, 47 or 53 and a light chain variable region whose amino acid sequence is set forth in SEQ ID NO: 54 or 60; or (VI) a heavy chain variable region whose amino acid sequence is set forth in SEQ ID NO: 50 and a light chain variable region whose amino acid sequence is set forth in SEQ ID NO: 55; or (VII) a heavy chain variable region whose amino acid sequence is set forth in SEQ ID NO: 50 and a light chain variable region whose amino acid sequence is set forth in SEQ ID NO: 56; or (VIII) a heavy chain variable region whose amino acid sequence is set forth in SEQ ID NO: 46 and a light chain variable region whose amino acid sequence is set forth in SEQ ID NO: 60; or (IX) a heavy chain variable region whose amino acid sequence is set forth in SEQ ID NO: 53 and a light chain variable region whose amino acid sequence is set forth in SEQ ID NO: 60.

In some embodiments, the antibody comprises a heavy chain and a light chain, wherein the heavy chain comprises an amino acid sequence set forth in any one of SEQ ID NOs: 63, 65, 67 and 69, or an amino acid sequence having at least 90%, 92%, 94%, 95%, 96%, 97%, 98% or 99% sequence identity to an amino acid sequence set forth in any one of SEQ ID NOs: 63, 65, 67 and 69;

the light chain comprises an amino acid sequence set forth in any one of SEQ ID NOs: 64, 66, 68 and 70, or an amino acid sequence having at least 90%, 92%, 94%, 95%, 96%, 97%, 98% or 99% sequence identity to an amino acid sequence set forth in any one of SEQ ID NOs: 64, 66, 68 and 70.

In some embodiments, the antibody comprises:
(I) a heavy chain whose amino acid sequence is set forth in SEQ ID NO: 63 and a light chain whose amino acid sequence is set forth in SEQ ID NO: 64; or
(II) a heavy chain whose amino acid sequence is set forth in SEQ ID NO: 65 and a light chain whose amino acid sequence is set forth in SEQ ID NO: 66; or
(III) a heavy chain whose amino acid sequence is set forth in SEQ ID NO: 67 and a light chain whose amino acid sequence is set forth in SEQ ID NO: 68; or
(IV) a heavy chain whose amino acid sequence is set forth in SEQ ID NO: 69 and a light chain whose amino acid sequence is set forth in SEQ ID NO: 70.

In some embodiments, the antibody or the antigen-binding fragment thereof is a murine antibody, a chimeric antibody, a humanized antibody or a fully human antibody, or an antigen-binding fragment thereof.

In some embodiments, the antigen-binding fragment is a Fab, Fab', F(ab')2, Fv, scFv or sdAb.

In some embodiments, the anti-CTLA-4 antibody or the antigen-binding fragment disclosed herein is of any IgG subtype, such as IgG1, IgG2, IgG3 or IgG4, preferably IgG1 or IgG4, and more preferably an IgG1 kappa subtype.

In another aspect, the present invention provides an isolated anti-CTLA-4 antibody or an antigen-binding fragment thereof, which has one or more of the following properties:

(1) binding to the same epitope of human CTLA-4 protein as the anti-CTLA-4 antibody or the antigen-binding fragment thereof disclosed herein, or binding to an epitope of human CTLA-4 protein that completely or partially overlaps with that to which the anti-CTLA-4 antibody or the antigen-binding fragment thereof disclosed herein binds;

(2) competing for binding to an epitope of human CTLA-4 protein with the anti-CTLA-4 antibody or the antigen-binding fragment thereof disclosed herein;

(3) binding to an epitope consisting of residues 27-29 of SEQ ID NO: 71, wherein amino acid residue numbering starts at A37 of SEQ ID NO: 71;

(4) binding to one or more of amino acid residues 27, 28 and 29 of SEQ ID NO: 71, wherein amino acid residue numbering starts at A37 of SEQ ID NO: 71;

(5) inhibiting or blocking binding of human CTLA-4 protein to human CD80 and/or human CD86 or cells expressing human CD80 and/or human CD86, wherein preferably, the isolated anti-CTLA-4 antibody or the antigen-binding fragment thereof competitively binds to CD80 via amino acid residues which are one or more of 135, 137, 138 and 140, wherein amino acid residue numbering starts at M1 of SEQ ID NO: 71;

(6) binding to an epitope consisting of residues 36-41 and/or 59-66 and/or 109-110 and/or 133-140 of SEQ ID NO: 71, wherein amino acid residue numbering starts at M1 of SEQ ID NO: 71; and (7) binding to one or more of amino acid residues 36, 39, 41, 59, 61, 62, 63, 64, 65, 66, 109, 110, 133, 135, 136, 137, 138 and 140 of SEQ ID NO: 71, wherein amino acid residue numbering starts at M1 of SEQ ID NO: 71.

The present invention also provides an isolated antibody or an antigen-binding fragment thereof, which binds to the same epitope of human CTLA-4 protein as the anti-CTLA-4 antibody described above, or which binds to an epitope of human CTLA-4 protein that overlaps with that to which the anti-CTLA-4 antibody described above binds.

The present invention also provides an isolated antibody or an antigen-binding fragment thereof, which competes with the anti-CTLA-4 antibody described above for binding to an epitope of human CTLA-4 protein.

The present invention also provides an isolated antibody or an antigen-binding fragment thereof, which binds to the same epitope of human CTLA-4 protein as antibody huJS007-47, or which binds to an epitope of human CTLA-4 protein that completely or partially overlaps with that to which antibody huJS007-47 binds.

The present invention also provides an isolated antibody or an antigen-binding fragment thereof, which competes with antibody huJS007-47 for binding to an epitope of human CTLA-4 protein.

In some embodiments, the anti-CTLA-4 antibody or the antigen-binding fragment thereof disclosed herein binds to an epitope consisting of residues 27-29 of SEQ ID NO: 71, wherein amino acid residue numbering starts at A37 of SEQ ID NO: 71.

In some embodiments, the anti-CTLA-4 antibody or the antigen-binding fragment thereof disclosed herein binds to an epitope consisting of residues 63-65 of SEQ ID NO: 71, wherein amino acid residue numbering starts at M1 of SEQ ID NO: 71.

In some embodiments, the anti-CTLA-4 antibody or the antigen-binding fragment thereof disclosed herein binds to one or more epitopes selected from amino acid residues 27, 28 and 29 of SEQ ID NO: 71, wherein amino acid residue numbering starts at A37 of SEQ ID NO: 71.

In some embodiments, the anti-CTLA-4 antibody or the antigen-binding fragment thereof disclosed herein binds to one or more epitopes selected from amino acid residues 63, 64 and 65 of SEQ ID NO: 71, wherein amino acid residue numbering starts at M1 of SEQ ID NO: 71.

In some embodiments, the anti-CTLA-4 antibody or the antigen-binding fragment thereof disclosed herein binds to human CTLA-4 at an epitope of amino acid residue 27 of SEQ ID NO: 71, wherein amino acid residue numbering starts at A37 of SEQ ID NO: 71.

In some embodiments, the anti-CTLA-4 antibody or the antigen-binding fragment thereof disclosed herein binds to human CTLA-4 at an epitope of amino acid residue 28 of SEQ ID NO: 71, wherein amino acid residue numbering starts at A37 of SEQ ID NO: 71.

In some embodiments, the anti-CTLA-4 antibody or the antigen-binding fragment thereof disclosed herein binds to human CTLA-4 at an epitope of amino acid residue 29 of SEQ ID NO: 71, wherein amino acid residue numbering starts at A37 of SEQ ID NO: 71.

In some embodiments, the anti-CTLA-4 antibody or the antigen-binding fragment thereof disclosed herein and ipilimumab bind to different epitopes of human CTLA-4 protein. In some embodiments, the anti-CTLA-4 antibody disclosed herein inhibits or blocks binding of human CTLA-4 protein to human CD80 or to human CD86; preferably, its amino acid residues that competitively bind to CD80 are one or more of 135, 137, 138 and 140, wherein amino acid residue numbering starts at M1 of SEQ ID NO: 71.

In some embodiments, the anti-CTLA-4 antibody or the antigen-binding fragment disclosed herein binds to an epitope consisting of residues 36-41 and/or 59-66 and/or 109-110 and/or 133-140 of SEQ ID NO: 71, wherein amino acid residue numbering starts at M1 of SEQ ID NO: 71.

In some embodiments, the anti-CTLA-4 antibody or the antigen-binding fragment thereof disclosed herein binds to one or more epitopes selected from amino acid residues 36, 39, 41, 59, 61, 62, 63, 64, 65, 66, 109, 110, 133, 135, 136, 137, 138 and 140 of SEQ ID NO: 71, wherein amino acid residue numbering starts at M1 of SEQ ID NO: 71.

The present invention also provides a multispecific antibody, which comprises the light chain variable region and the heavy chain variable region of the antibody or the antigen-binding fragment thereof disclosed herein.

The present invention also provides a single-chain antibody, which comprises the light chain variable region and the heavy chain variable region of the antibody or the antigen-binding fragment thereof disclosed herein.

The present invention also provides an immunoconjugate, which comprises the antibody or the antigen-binding fragment thereof disclosed herein conjugated to a therapeutic or diagnostic agent.

In yet another aspect, the present invention provides a polynucleotide, which encodes the anti-CTLA-4 antibody or the antigen-binding fragment thereof disclosed herein.

In yet another aspect, the present invention provides an expression vector, which comprises the polynucleotide disclosed herein, wherein preferably, the vector is a eukaryotic expression vector.

In yet another aspect, the present invention provides a host cell, which comprises the polynucleotide disclosed herein or the expression vector disclosed herein, wherein preferably, the host cell is a eukaryotic cell; more preferably, the host cell is a mammalian cell.

In yet another aspect, the present invention provides a method for preparing the anti-CTLA-4 antibody or the antigen-binding fragment thereof disclosed herein, which comprises expressing the antibody or the antigen-binding fragment thereof in the host cell disclosed herein under conditions suitable for expression of the antibody or the antigen-binding fragment thereof, and isolating the expressed antibody or antigen-binding fragment thereof from the host cell.

In yet another aspect, the present invention provides a pharmaceutical composition, which comprises the anti-CTLA-4 antibody or the antigen-binding fragment thereof disclosed herein, the polynucleotide disclosed herein, the expression vector disclosed herein, the host cell disclosed herein, and a pharmaceutically acceptable carrier or excipient.

In yet another aspect, the present invention provides use of the antibody or the antigen-binding fragment thereof disclosed herein, the polynucleotide disclosed herein, the expression vector disclosed herein, the host cell disclosed herein or the pharmaceutical composition disclosed herein in the manufacture of a medicament for the treatment and/or prevention of a CTLA-4-mediated disease or disorder, wherein preferably, the disease or disorder is cancer; more preferably, the cancer is selected from melanoma, renal cancer, prostate cancer, breast cancer, colon cancer, lung cancer, bone cancer, pancreatic cancer, skin cancer, head and neck cancer, uterine cancer, ovarian cancer and rectal cancer.

In yet another aspect, the present invention provides the antibody or the antigen-binding fragment thereof disclosed herein, the polynucleotide disclosed herein, the expression vector disclosed herein, the host cell disclosed herein or the pharmaceutical composition disclosed herein for use in the treatment and/or prevention of a CTLA-4-mediated disease or disorder, wherein preferably, the disease or disorder is cancer; more preferably, the cancer is selected from melanoma, renal cancer, prostate cancer, breast cancer, colon cancer, lung cancer, bone cancer, pancreatic cancer, skin cancer, head and neck cancer, uterine cancer, ovarian cancer and rectal cancer.

In yet another aspect, the present invention provides a method for treating and/or preventing a CTLA-4-mediated disease or disorder, which comprises administering to a subject in need the antibody or the antigen-binding fragment thereof disclosed herein, the polynucleotide disclosed herein, the expression vector disclosed herein, the host cell disclosed herein or the pharmaceutical composition disclosed herein, wherein preferably, the disease or disorder is cancer; more preferably, the cancer is selected from melanoma, renal cancer, prostate cancer, breast cancer, colon cancer, lung cancer, bone cancer, pancreatic cancer, skin cancer, head and neck cancer, uterine cancer, ovarian cancer and rectal cancer.

In yet another aspect, the present invention provides a pharmaceutical combination, which comprises the antibody or the antigen-binding fragment thereof disclosed herein, the polynucleotide disclosed herein, the expression vector disclosed herein, the host cell disclosed herein or the pharmaceutical composition disclosed herein, and one or more additional therapeutic agents.

In yet another aspect, the present invention provides a kit, which comprises the antibody or the antigen-binding fragment thereof disclosed herein, the polynucleotide disclosed herein, the expression vector disclosed herein, the host cell disclosed herein or the pharmaceutical composition disclosed herein, and which preferably further comprises a drug delivery device.

In yet another aspect, the present invention provides a method for detecting the presence of CTLA-4 in a sample using the antibody or the antigen-binding fragment thereof disclosed herein.

BRIEF DESCRIPTION OF THE DRAWINGS

FIG. 9: ELISA detection of the binding of humanized anti-CTLA-4 antibodies to huCTLA-4.

FIG. 10: ELISA determination of the abilities of humanized anti-CTLA-4 antibodies to block the binding of huCTLA-4 to CD80.

FIG. 20: the overall structure and interaction details of JS007 binding to CTLA-4.

FIG. 21: the molecular basis of JS007 competing with B7-1 for binding to CTLA-4.

DETAILED DESCRIPTION

Definitions

Figure 1:
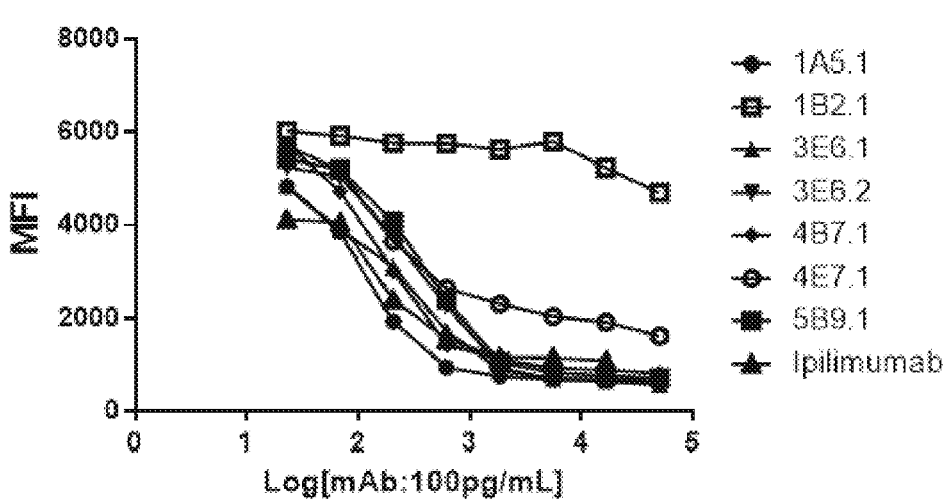
FIG. 1: FACS detection of hybridoma anti-CTLA-4 antibodies' blocking of the binding of huCTLA-4 to huCD80.

Unless otherwise stated, embodiments of the present invention will employ conventional techniques of molecular biology (including recombinant techniques), microbiology, cytobiology, biochemistry and immunology, which are all within the skill of the art.

In order to facilitate the understanding of the present invention, some technical and scientific terms are specifically defined as follows. Unless otherwise specifically defined herein, all technical and scientific terms used herein have the same meanings as commonly understood by those of ordinary skill in the art to which the present invention belongs. For definitions and terminology in the art, the skilled person can refer specifically to Current Protocols in Molecular Biology (Ausubel). Abbreviations for amino acid residues are standard 3-letter and/or 1-letter codes used in the art to denote one of the 20 commonly used L-amino acids. The singular forms used herein (including claims) include their plural forms, unless otherwise specified in the context explicitly.

The term "about" used in combination with a numerical value is intended to encompass the numerical values in a range from a lower limit less than the specified numerical value by 5% to an upper limit greater than the specified numerical value by 5%, including but not limited to ±5%, ±2%, ±1% and ±0.1%, as these variations are suitable for carrying out the disclosed methods.

The term "and/or" should be understood as any one of the options or a combination of any two or more of the options.

As used herein, the term "or" should be understood as having the same meaning as "and/or" defined above. For example, when items in a list are separated, "or" or "and/or" should be interpreted as being inclusive, that is, including at least one number or one of a list of elements, but also including more than one, and, optionally, additional unlisted items. Only in cases where contrary terms such as "only one" or "exactly one", or "consisting of . . . " used in the claims, are explicitly indicated will it refers to the one number solely listed or one element of a list.

As used herein, the terms "a/an" and "one" should be understood as "at least one", unless otherwise specified.

The terms "cytotoxic T lymphocyte-associated antigen 4", "protein CTLA-4", "CTLA-4 recombinant protein", "CTLA-4", "CTLA4" and "CTLA-4 antigen" are used interchangeably and include variants, subtypes, species homologs of human CTLA-4, or CTLA-4 of other species, and analogs which have at least one epitope in common with CTLA-4, unless otherwise stated. This term encompasses "full-length" unprocessed CTLA-4 and CTLA-4 in any form resulting from intracellular processing or any fragment thereof. In one embodiment, CTLA-4 refers to full-length CTLA-4 from humans and cynomolgus monkeys or fragments thereof (such as mature fragments thereof lacking a signal peptide).

The term "human CTLA-4" refers to human sequence CTLA-4, such as the complete amino acid sequence of the human CTLA-4 under NCBI accession No. NM_005214.3. A human CTLA-4 sequence may differ from the human CTLA-4 under NCBI accession No. NM_005214.3 by having a conservative mutation or a mutation in a non-conservative region, and CTLA-4 has substantially the same biological function as the human CTLA-4 under NCBI accession No. NM_005214.3. For example, the biological function of human CTLA-4 is to have an epitope in the extracellular domain of CTLA-4 to which the anti-CTLA-4 constructs of the present disclosure bind specifically, or the biological function of human CTLA-4 is to modulate T cell activity.

The term "huCD80" refers to human sequence huCD80, such as the complete amino acid sequence of the huCD80 under NCBI accession No. NM_005191.3. The term "huCD86" refers to human sequence huCD86, such as the complete amino acid sequence of the huCD86 under NCBI accession No. NM_006889.3. The term "cynomolgus monkey CD86" refers to cynomolgus monkey sequence cyno CD86, such as the complete amino acid sequence of the cynomolgus monkey CD86 under NCBI accession No. NM_102115124.

The term "percent (%) amino acid sequence identity", or simply "identity", is defined as the percentage of amino acid residues in a candidate amino acid sequence that are identical to those in a reference amino acid sequence after aligning the amino acid sequences (with gaps introduced if necessary) to achieve maximum percent sequence identity without considering any conservative substitution as part of sequence identity. Various methods in the art can be employed to perform sequence alignment so as to determine the percent amino acid sequence identity, for example, using computer software available to the public, such as BLAST, BLAST-2, ALIGN, or MEGALIGN (DNASTAR) software. Those skilled in the art can determine suitable parameters for measuring alignment, including any algorithm required to obtain maximum alignment for the full length of the aligned sequences.

The term "immune response" refers to the action of, for example, lymphocytes, antigen-presenting cells, phagocytes, granulocytes, and soluble macromolecules produced by the above cells or liver (including antibodies, cytokines and complements) that results in selective damage to, destruction of, or elimination from the human body of invading pathogens, cells or tissues infected with pathogens, cancerous cells, or, in the cases of autoimmunity or pathological inflammation, normal human cells or tissues.

The term "signal transduction pathway" or "signal transduction activity" refers to a biochemical causal relationship generally initiated by an interaction between proteins (such as binding of a growth factor to a receptor) and resulting in transmission of a signal from one portion of a cell to another portion of the cell. In general, the transmission includes specific phosphorylation of one or more tyrosine, serine or threonine residues on one or more proteins in a series of reactions causing signal transduction. The penultimate process typically involves a nuclear event, resulting in a change in gene expression.

The term "activity" or "bioactivity", or the term "biological property" or "biological characteristic" are used interchangeably herein and includes, but is not limited to, epitope/antigen affinity and specificity, the ability to neutralize or antagonize CTLA-4 activity in vivo or in vitro, $IC_{50}$, the in vivo stability of the antibody, and the immunogenic properties of the antibody. Other identifiable biological properties or characteristics of the antibody known in the art include, for example, cross-reactivity (i.e., cross-reactivity with non-human homologs of the targeted peptide, or with other proteins or tissues in general), and the ability to maintain high expression level of the protein in mammalian cells. The aforementioned properties or characteristics are observed, determined or assessed using techniques well known in the art, including but not limited to ELISA, FACS or BIACORE plasma resonance analysis, unlimited in vitro or in vivo neutralization assays, receptor binding, cytokine or growth factor production and/or secretion, signal transduction, and immunohistochemistry of tissue sections of different origins (including human, primate or any other origin). The term "antibody" refers to any form of an antibody with desired bioactivity. Thus, it is used in the broadest sense and specifically includes, but is not limited to, monoclonal antibodies (including full-length monoclonal antibodies), polyclonal antibodies, multispecific antibodies (e.g., bispecific antibodies), humanized antibodies, fully human antibodies, chimeric antibodies, and camelized single-domain antibodies.

The term "isolated antibody" refers to the purified state of a binding compound, and, in this case, means that the molecule is substantially free of other biomolecules, such as nucleic acids, proteins, lipids, sugars, or other substances such as cell debris and growth medium. The term "isolate (d)" does not mean the complete absence of such substances or the absence of water, buffers or salts, unless they are present in amounts that will significantly interfere with the experimental or therapeutic use of the binding compounds described herein.

The term "monoclonal antibody" refers to an antibody obtained from a substantially homogeneous population of antibodies, i.e., the antibodies composing the population are identical except for possible naturally occurring mutations that may be present in minor amounts. A monoclonal antibody is highly specific and targets a single antigen epitope. In contrast, conventional (polyclonal) antibody preparations typically include a large number of antibodies targeting (or specific for) different epitopes. The modifier "monoclonal" indicates the characteristic of an antibody obtained from a substantially homogeneous population of antibodies, and is not to be construed as producing the antibody by any particular method. The term "full-length antibody" refers to an immunoglobulin molecule comprising at least four peptide chains when present naturally, including two heavy (H) chains and two light (L) chains linked to each other by disulfide bonds. Each heavy chain consists of a heavy chain variable region (abbreviated herein as VH) and a heavy chain constant region (abbreviated herein as CH). The heavy chain constant region consists of 3 domains CH1, CH2 and CH3. Each light chain consists of a light chain variable region (abbreviated herein as VL) and a light chain constant region. The light chain constant region consists of one domain CL. The VH and VL regions can be further divided into complementarity-determining regions (CDRs) with high variability and more conservative regions called framework regions (FRs) that are spaced apart by the CDRs. Each VH or VL region consists of 3 CDRs and 4 FRs arranged in the following order from the amino terminus to the carboxyl terminus: FR1, CDR1, FR2, CDR2, FR3, CDR3, FR4. The variable regions of the heavy and light chains contain binding domains that interact with antigens. The constant regions of an antibody can mediate the binding of immunoglobulins to host tissues or factors, including the binding of various cells of the immune system (e.g., effector cells) to the first component (Clq) of a classical complement system.

The "antigen-binding fragment" of an antibody ("parent antibody") includes a fragment or a derivative of the antibody, generally including at least one fragment of an antigen-binding region or variable region (e.g., one or more CDRs) of a parent antibody, which retains at least some of the binding specificity of the parent antibody. Examples of binding fragments of an antibody include, but are not limited to, Fab, Fab', F(ab')2 and Fv fragments; a diabody; a linear antibody: a single-chain antibody molecule, such as sc-Fv; and a nanobody and a multispecific antibody formed by fragments of the antibody. A binding fragment or a derivative generally retains at least 10% of its antigen-binding activity when the antigen-binding activity is expressed on a molar concentration basis. Preferably, the binding fragment or derivative retains at least 20%, 50%, 70%, 80%, 90%, 95% or 100% or more of the antigen-binding affinity of the parent antibody. It is also contemplated that an antigen-binding fragment of an antibody may include conservative or non-conservative amino acid substitutions that do not significantly alter its bioactivity (referred to as "conservative variants" or "function-conservative variants" of the antibody). The term "binding compound" refers to both an antibody and a binding fragment thereof.

The term "single-chain Fv" or "scFv" antibody refers to an antibody fragment comprising the VH and VL domains of an antibody, where these domains are present in a single polypeptide chain. In general, an Fv polypeptide also comprises a polypeptide linker between the VH and VL domains that enables the scFv to form the desired structure for antigen-binding.

The term "domain antibody" is an immunofunctional immunoglobulin fragment that contains only the heavy chain variable region or the light chain variable region. In certain cases, two or more VH regions are covalently linked to a peptide linker to form a bivalent domain antibody. The two VH regions of the bivalent domain antibody may target the same or different antigens.

The term "bivalent antibody" comprises two antigen-binding sites. In certain cases, the two binding sites have the same antigen specificity. However, a bivalent antibody may be bispecific.

The term "diabody" refers to a small antibody fragment having two antigen-binding sites and comprising a heavy chain variable domain (VH) linked to a light chain variable domain (VL) in the same polypeptide chain (VH-VL or VL-VH). By using a linker that is too short to allow pairing between two domains in one chain, the domains are forced to pair with the complementary domains of the other chain to form two antigen-binding sites.

The term "murine antibody" or "hybridoma antibody" in the present disclosure refers to an anti-human CTLA-4 monoclonal antibody prepared according to the knowledge and skills in the art. The preparation is carried out by injecting the test subject with the CTLA-4 antigen and then isolating hybridomas expressing antibodies with the desired sequences or functional properties.

The term "chimeric antibody" is an antibody having the variable domains of a first antibody and the constant domains of a second antibody, wherein the first and second antibodies are from different species. Typically, the variable domains are obtained from an antibody of an experimental animal such as a rodent ("parent antibody"), and the constant domain sequences are obtained from a human antibody, such that the resulting chimeric antibody is less likely to induce an adverse immune response in a human subject as compared to the parent rodent antibody.

The term "humanized antibody" refers to an antibody form containing sequences from both human and non-human (such as mouse and rat) antibodies. In general, a humanized antibody comprises substantially all of at least one, and typically two, variable domains, in which all or substantially all of the hypervariable loops correspond to those of a non-human immunoglobulin and all or substantially all of the framework regions (FRs) are those of a human immunoglobulin sequence. The humanized antibody may optionally comprise at least a portion of a human immunoglobulin constant region (Fc).

The term "fully human antibody" refers to an antibody that comprises only human immunoglobulin sequences. A fully human antibody may contain mouse glycochains if produced in mice, mouse cells or hybridomas derived from mouse cells. Likewise, a "mouse antibody" refers to an antibody that comprises only mouse immunoglobulin sequences. Alternatively, a fully human antibody may contain rat glycochains if produced in rats, rat cells or hybridomas derived from rat cells. Likewise, a "rat antibody" refers to an antibody that comprises only rat immunoglobulin sequences.

"Isotypes" of antibodies refer to types of antibodies (e.g., IgM. IgE and IgG (such as IgG1, IgG2 or IgG4)) provided by heavy chain constant region genes. Isotype also includes modified forms of one of these types in which modifications have been made to alter Fc function, for example to enhance or attenuate effector function or binding to Fc receptors.

The term "epitope" refers to a protein determinant capable of specific binding to an antibody. Epitopes are usually composed of a variety of chemically active surface molecules such as amino acids or sugar side chains and usually have specific three-dimensional structural characteristics as well as specific charge characteristics. Conformational epitopes and non-conformational epitopes differ in that binding to the former rather than the latter fails in the presence of denaturing solvents.

The term "cross-reaction" as described herein refers to binding to antigenic fragments of the same target molecule of human, monkey and/or murine (mouse or rat) origin. Thus, "cross-reaction" should be understood as an interspecies reaction with the same molecule X expressed in different species. The cross-reaction specificity of monoclonal antibodies recognizing human CTLA-4, monkey and/or murine (mouse or rat) CTLA-4 can be determined by FACS analysis.

"Affinity" or "binding affinity" refers to inherent binding affinity that reflects the interaction between members of a binding pair. The affinity of molecule X for its partner Y can be generally represented by the equilibrium dissociation constant (KD), which is a ratio of the dissociation rate constant to the association rate constant (kdis and kon, respectively). Affinity can be measured using common methods known in the art. One particular method for measuring affinity is the ForteBio kinetic binding assay herein.

The term "not bind" to a protein or cell means not binding to the protein or cell, or not binding to it with high affinity, that is, binding to the protein or cell with a KD of $1.0 \times 10^{-6}$ M or higher, more preferably $1.0 \times 10^{-5}$ M or higher, more preferably $1.0 \times 10^{-4}$ M or higher, $1.0 \times 10^{-3}$ M or higher, and more preferably $1.0 \times 10^{-2}$ M or higher.

The term "high affinity" of IgG antibodies means a $K_D$ for the antigen of $1.0 \times 10^{-6}$ M or less, preferably $5.0 \times 10^{-8}$ M or less, more preferably $1.0 \times 10^{-8}$ M or less, $5.0 \times 10^{-9}$M or less, and more preferably $1.0 \times 10^{-9}$ M or less. For other antibody subtypes, "high affinity" binding may vary. For example, "high affinity" binding of the IgM subtype means a $K_D$ of $10^{-6}$ M or less, preferably $10^{-7}$ M or less, and more preferably $10^{-8}$ M or less.

The term "antibody-dependent cytotoxicity", "antibody-dependent cell-mediated cytotoxicity" or "ADCC" refer to a cell-mediated immune defense in which the effector cells of the immune system actively lyse target cells, such as cancer cells, whose cell membrane surface antigens bind to antibodies, such as CTLA-4 antibodies.

The term "complement-dependent cytotoxicity" or "CDC" refers to the effector function of IgG and IgM antibodies, which, when bind to surface antigens, trigger typical complement pathways, including formation of membrane attack complexes and lysis of target cells. The antibody disclosed herein, when binds to CTLA-4, triggers CDC against cancer cells.

The term "nucleic acid" or "polynucleotide" refers to deoxyribonucleic acid (DNA) or ribonucleic acid (RNA) and polymers thereof in either single- or double-stranded form. Unless explicitly limited, the term includes nucleic acids containing known analogs of natural nucleotides that have binding properties similar to that of the reference nucleic acid and are metabolized in a manner similar to naturally occurring nucleotides (see U.S. Pat. No. 8,278,036 to Kariko et al., which discloses an mRNA molecule with uridine replaced by pseudouridine, a method for synthesizing the mRNA molecule, and a method for delivering a therapeutic protein in vivo). Unless otherwise specified, a particular nucleic acid sequence also implicitly includes conservatively modified variants thereof (e.g., degenerate codon substitutions), alleles, orthologs, SNPs, and complementary sequences as well as the sequence explicitly indicated. Specifically, degenerate codon substitutions can be achieved by generating sequences in which the third position of one or more selected (or all) codons is substituted with mixed bases and/or deoxyinosine residues (Batzer et al.,

*Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

"Construct" refers to any recombinant polynucleotide molecule (such as plasmid, cosmid, virus, autonomously replicating polynucleotide molecule, phage, or linear or circular single- or double-stranded DNA or RNA polynucleotide molecule) derived from any source, capable of genomic integration or autonomous replication, and comprising a polynucleotide molecule where one or more polynucleotide molecules have been linked in a functionally operative manner (i.e., operably linked). The recombinant construct typically comprises a polynucleotide of the present invention operably linked to transcription initiation regulatory sequences that will direct transcription of the polynucleotide in a host cell. Both heterologous and non-heterologous (i.e., endogenous) promoters can be used to direct expression of the nucleic acids of the present invention.

"Vector" refers to any recombinant polynucleotide construct that can be used for transformation purpose (i.e., the introduction of heterologous DNA into a host cell). One type of vector is a "plasmid", which refers to a double-stranded DNA loop into which additional DNA segments can be ligated. Another type of vector is a viral vector, in which additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., nonepisomal mammalian vectors) are integrated into the genome of the host cell upon introduction into a host cell, and are thereby replicated along with the host genome. In addition, certain vectors are capable of directing the expression of operably linked genes. Such vectors are referred to herein as "expression vectors".

The term "expression vector" as used herein refers to a nucleic acid molecule capable of replicating and expressing a target gene when transformed, transfected or transduced into a host cell. The expression vector comprises one or more phenotypic selectable markers and an origin of replication to ensure maintenance of the vector and to provide amplification in the host if needed.

Unless otherwise or explicitly specified in the context, "activation", "stimulation" and "treatment" for a cell or a receptor may have the same meaning. For example, the cell or the receptor is activated, stimulated or treated with a ligand. "Ligands" include natural and synthetic ligands, such as cytokines, cytokine variants, analogs, mutant proteins, and binding compounds derived from antibodies. "Ligands" also include small molecules, such as peptidomimetics of cytokines and peptidomimetics of antibodies. "Activation" may refer to the activation of a cell regulated by internal mechanisms and external or environmental factors. "Response/reaction", e.g., a response of a cell, a tissue, an organ or an organism, includes changes in biochemical or physiological behaviors (e.g., concentration, density, adhesion or migration, gene expression rate, or differentiation state within a biological compartment), where the changes are associated with activation, stimulation or treatment, or are associated with an internal mechanism such as genetic programming.

As used herein, the term "treat", "treating" or "treatment" of any disease or disorder refers in one embodiment to ameliorating the disease or disorder (i.e., slowing or arresting or reducing the progression of the disease or at least one of its clinical symptoms). In another embodiment, "treat", "treating" or "treatment" refers to ameliorating or alleviating at least one physical parameter, including those physical parameters that may not be discernible by the patient. In another embodiment, "treat", "treating" or "treatment" refers to modulating the disease or disorder, physically (e.g., stabilization of discernible symptoms), physiologically (e.g., stabilization of physical parameters), or both. Unless explicitly described herein, methods for assessing treatment and/or prevention of a disease are generally known in the art.

A "subject" includes any human or non-human animal. The term "non-human animal" includes all vertebrates, e.g., mammals and non-mammals, such as non-human primates, sheep, dog, cat, horse, cattle, chicken, amphibians, and reptiles. As used herein, the term "cyno" refers to a cynomolgus monkey. Administration "in combination with" one or more other therapeutic agents includes simultaneous (co-) administration and sequential administration in any order.

"Therapeutically effective amount", "therapeutically effective dose" and "effective amount" refer to an amount of the anti-CTLA-4 antibody or the antigen-binding fragment thereof disclosed herein that is effective in preventing or ameliorating one or more symptoms of a disease or condition or the progression of the disease or condition when administered alone or in combination with other therapeutic drugs to a cell, a tissue or a subject. The therapeutically effective dose also refers to an amount of the antibody or the antigen-binding fragment thereof sufficient to cause amelioration of symptoms, e.g., an amount for treating, curing, preventing or ameliorating a related condition or promoting the treatment, cure, prevention or amelioration of such condition. When an active ingredient is administered to an individual alone, a therapeutically effective dose refers to the amount of the ingredient. In the case of administration in combination, a therapeutically effective dose refers to the combined amount of active ingredients that produces a therapeutic effect, regardless of whether these active ingredients are administered in combination, sequentially or simultaneously. An effective amount of a therapeutic agent will increase a diagnostic index or parameter by at least 10%, generally at least 20%, preferably at least about 30%, more preferably at least 40%, and most preferably at least 50%.

"Cancer" and "cancerous" refer to or describe the physiological condition in mammals which is typically characterized by unregulated cell growth. Included in this definition are benign and malignant cancers as well as dormant tumors or micrometastases. Examples of cancer include, but are not limited to, carcinoma, lymphoma, blastoma, sarcoma and leukemia. More specific examples of such cancers include squamous cell carcinoma, lung cancer (including small cell lung cancer, non-small cell lung cancer, adenocarcinoma of the lung and squamous carcinoma of the lung), peritoneal cancer, hepatocellular cancer, cancer of the stomach or gastric cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial cancer or uterine cancer, salivary gland carcinoma, renal cancer or cancer of the kidney, prostatic cancer, vulval cancer, thyroid cancer, cancer of the liver, and various types of head and neck cancers, as well as B-cell lymphoma (including low-grade/follicular non-Hodgkin lymphoma (NHL), small lymphocytic (SL) NHL, intermediate-grade/follicular NHL, intermediate-grade diffuse NHL, high-grade immunoblastic NHL, high-grade lymphoblastic NHL, high-grade small non-cleaved cell NHL, bulky disease NHL, mantle cell lymphoma, AIDS-related lymphomas, and Waldenstrom macroglobulinemia), chronic lymphocytic leukemia (CLL), acute lymphoblastic leukemia (ALL), hairy cell leukemia, chronic myeloblastic leukemia, post-transplant lymphoproliferative disorder (PTLD), and abnormal vascular proliferation associated with phakomatoses, edema (such as associated with brain tumors) and Meigs syndrome.

Anti-CTLA-4 Antibody

In one aspect, the present invention provides an anti-CTLA-4 antibody or an antigen-binding fragment thereof. The term "anti-CTLA-4 antibody", "anti-CTLA-4", "CTLA-4 antibody" or "CTLA-4-binding antibody" refers to an antibody that is capable of binding to a CTLA-4 protein or a fragment thereof with sufficient affinity such that the antibody can be used as a diagnostic and/or therapeutic agent targeting CTLA-4.

Any suitable method for producing antibodies may be employed to produce the antibody disclosed herein. CTLA-4 in any suitable form may be used as an immunogen (antigen) for antibody production. By way of example rather than limitation, any CTLA-4 variant or a fragment thereof may be used as an immunogen. In some embodiments, hybridoma cells that produce murine monoclonal anti-human CTLA-4 antibodies can be produced by methods well known in the art.

Antibodies derived from rodents (e.g., mice) may induce unwanted immunogenicity of the antibodies when used as therapeutic agents in vivo. Repeated use of these antibodies induces an immune response in the human body to therapeutic antibodies. Such immune responses result in at least a loss of therapeutic efficacy and, in severe cases, a potentially lethal allergic reaction. One method for reducing the immunogenicity of rodent antibodies includes producing chimeric antibodies, in which the mouse variable region is fused to the human constant region (Liu et al., (1987) *Proc. Natl. Acad. Sci. USA* 84:3439-43). However, the preservation of intact rodent variable regions in a chimeric antibody can still induce deleterious immunogenicity in patients. Grafting of the complementarity-determining region (CDR) loops of the rodent variable domain onto the human framework (i.e., humanization) has been used to further minimize rodent sequences (Jones et al., (1986) *Nature* 321:522; Verhoeyen et al., (1988) *Science* 239:1534).

In some embodiments, the chimeric or humanized antibodies disclosed herein can be prepared based on the sequences of the prepared murine monoclonal hybridoma antibodies. DNA encoding the immunoglobulin heavy and light chains can be obtained from a murine hybridoma of interest and engineered to comprise non-murine (e.g., human) immunoglobulin sequences using standard molecular biology techniques. In some embodiments, to prepare the chimeric CTLA-4 antibodies disclosed herein, the chimeric heavy chains and the chimeric light chains can be obtained by operably linking the immunoglobulin heavy chain and light chain variable regions of hybridoma origin to human IgG constant regions respectively using methods known in the art (see, e.g., U.S. Pat. No. 4,816,567 to Cabilly et al.). In some embodiments, the chimeric antibodies disclosed herein comprise constant regions which can be selected from any human IgG subtype, such as IgG1, IgG2, IgG3 and IgG4, preferably IgG1 and IgG4, and more preferably an IgG1 kappa subtype.

In some embodiments, the chimeric CTLA-4 antibodies disclosed herein can be obtained by "mixing and matching" a chimeric light chain expression plasmid with a chimeric heavy chain expression plasmid to transfect expression cells. The CTLA-4 binding of such "mixed and matched" antibodies can be assayed using the above binding assays and other conventional binding assays (e.g., ELISA).

The precise amino acid sequence boundaries of the variable region CDRs of the antibodies of the present invention can be determined using any of many well-known schemes, including Chothia based on the three-dimensional structure of antibodies and the topology of the CDR loops (Chothia et al., (1989) *Nature* 342:877-883; Al-Lazikani et al., Standard conformations for the canonical structures of immunoglobulins, *Journal of Molecular Biology*, 273, 927-948 (1997)), Kabat based on antibody sequence variability (Kabat et al., *Sequences of Proteins of Immunological Interest*, 4$^{th}$ edition, U.S. Department of Health and Human Services, National Institutes of Health (1987)), AbM (University of Bath), Contact (University College London), International ImMunoGeneTics database (IMGT) (1999 *Nucleic Acids Research*, 27, 209-212), and North CDR definition based on the affinity propagation clustering using a large number of crystal structures. The boundaries of the CDRs of the antibodies of the present invention can be determined by those skilled in the art according to any scheme (e.g., different assignment systems or combinations) in the art.

It should be noted that the boundaries of the CDRs of the variable regions of the same antibody obtained based on different assignment systems may differ. That is, the CDR sequences of the variable regions of the same antibody defined under different assignment systems are different. Thus, when it comes to defining an antibody with a particular CDR sequence defined in the present invention, the scope of the antibody also encompasses antibodies whose variable region sequences comprise the particular CDR sequence but whose claimed CDR boundaries differ from the particular CDR boundaries defined in the present invention due to the application of different schemes (e.g., different assignment systems or combinations).

Antibodies with different specificities (i.e., different binding sites for different antigens) have different CDRs. However, although CDRs vary from antibody to antibody, only a limited number of amino acid positions within a CDR are directly involved in antigen binding. The smallest overlapping region can be determined using at least two of the Kabat, Chothia, AbM, Contact and North methods, thereby providing a "smallest binding unit" for antigen binding. The smallest binding unit may be a sub-portion of the CDR. As will be appreciated by those skilled in the art, the residues in the remainder of the CDR sequences can be determined by the antibody structure and protein folding. Thus, variants of any of the CDRs presented herein are also contemplated by the present invention. For example, in a variant of one CDR, the amino acid residue of the smallest binding unit may remain unchanged, while the remaining CDR residues defined according to Kabat or Chothia may be substituted by conservative amino acid residues.

For the humanized antibodies disclosed herein, murine CDR regions can be inserted into human germline framework regions using methods known in the art. See U.S. Pat. No. 5,225,539 to Winter et al and U.S. Pat. Nos. 5,530,101; 5,585,089; 5,693,762 and 6,180,370 to Queen et al. In some embodiments, amino acid changes include amino acid deletions, insertions or substitutions. In some embodiments, the anti-CTLA-4 antibodies or the antigen-binding fragments thereof disclosed herein include those antibodies having an amino acid sequence which has been mutated by amino acid deletion, insertion or substitution but still has at least about 90%, 91%, 92%, 93%, 94%, 95%, 96%, 97%, 98%, 99% or 100% identity to the aforementioned antibodies (particularly in the CDR regions depicted in the aforementioned sequences). In some embodiments, when compared to the CDR regions depicted in a particular sequence, the antibodies disclosed herein have no more than 1, 2, 3, 4 or 5 amino acid mutations (deletions, insertions or substitutions) in the CDR regions.

In some embodiments, polynucleotides encoding the antibodies disclosed herein include those that have been mutated by nucleotide deletion, insertion or substitution but still have at least about 60%, 70%, 80%, 90%, 95% or 100% identity to the corresponding CDR coding regions set forth in the above sequences. In some embodiments, one or more amino acid modifications may be introduced into an Fc region of an antibody provided herein, thus producing an Fc region variant. The Fc region variant may comprise human Fc region sequences (e.g., human IgG1, IgG2, IgG3 or IgG4 Fc regions) which comprise amino acid modifications (e.g., substitutions) at one or more amino acid positions.

In some embodiments, antibodies modified by cysteine engineering may need to be produced, such as "sulfo-MAb", wherein one or more residues of the antibodies are substituted by cysteine residues.

In some embodiments, the antibodies provided herein can be further modified to contain other non-protein moieties known in the art and readily available. Suitable moieties for antibody derivatization include, but are not limited to, water-soluble polymers. Non-limiting examples of water-soluble polymers include, but are not limited to, polyethylene glycol (PEG), ethylene glycol/propylene glycol copolymer, carboxymethyl cellulose, glucan, polyvinyl alcohol, polyvinylpyrrolidone, poly-1,3-dioxane, poly-1,3,6-trioxane, ethylene/maleic anhydride copolymer, polyamino acid (homopolymer or random copolymer), and glucan or poly(n-vinylpyrrolidone) polyethylene glycol, propylene glycol homopolymer, polypropylene oxide/ethylene oxide copolymer, polyoxyethylated polyol (such as glycerol), polyvinyl alcohol, and mixtures thereof.

Ipilimumab of the present invention is prepared by Suzhou Junmeng with reference to patent CN1371416B.

Expression of Antibodies

In yet another aspect, the present invention provides a polynucleotide, which encodes the anti-CTLA-4 antibody or the antigen-binding fragment thereof disclosed herein. The polynucleotide can include a polynucleotide encoding an amino acid sequence of the light chain variable region and/or heavy chain variable region of the antibody, or a polynucleotide encoding an amino acid sequence of the light chain and/or heavy chain of the antibody.

In yet another aspect, the present invention provides an expression vector, which comprises the polynucleotide disclosed herein, wherein preferably, the vector is a eukaryotic expression vector. In some embodiments, the polynucleotide disclosed herein is comprised in one or more expression vectors.

In yet another aspect, the present invention provides a host cell, which comprises the polynucleotide disclosed herein or the expression vector disclosed herein, wherein preferably, the host cell is a eukaryotic cell; more preferably, the host cell is a mammalian cell.

In yet another aspect, the present invention provides a method for preparing the anti-CTLA-4 antibody or the antigen-binding fragment thereof disclosed herein, which comprises expressing the antibody or the antigen-binding fragment thereof in the host cell disclosed herein under conditions suitable for expression of the antibody or the antigen-binding fragment thereof, and isolating the expressed antibody or antigen-binding fragment thereof from the host cell.

The present invention provides a mammalian host cell for expressing the recombinant antibody of the present invention, which includes a number of immortalized cell lines available from American Type Culture Collection (ATCC). Those cell lines include, in particular, Chinese hamster ovary (CHO) cells, NS0, SP2/0 cells, HeLa cells, baby hamster kidney (BHK) cells, monkey kidney cells (COS), human hepatocellular carcinoma cells, A549 cells, 293T cells and many other cell lines. Mammalian host cells include human, mouse, rat, dog, monkey, pig, goat, cow, horse and hamster cells. Particularly preferred cell lines are selected by determining which cell line has high expression level.

In one embodiment, the present invention provides a method for preparing an anti-CTLA-4 antibody, which comprises: introducing an expression vector into a mammalian host cell, and culturing the host cell for a period of time sufficient to allow expression of the antibody in the host cell or more preferably to allow secretion of the antibody into a medium in which the host cell is grown, thereby producing the antibody. The antibody can be isolated from the medium using standard protein purification methods.

It is likely that antibodies expressed by different cell lines or in transgenic animals have different glycosylations from each other. However, all antibodies encoded by the nucleic acid molecules provided herein or comprising the amino acid sequences provided herein are integral parts of the present invention, regardless of the glycosylation of the antibody. Likewise, in certain embodiments, nonfucosylated antibodies are advantageous because they generally have more potent efficacy in vitro and in vivo than their fucosylated counterparts, and are unlikely to be immunogenic because their glycan structures are normal components of natural human serum IgG.

Pharmaceutical Composition and Pharmaceutical Formulation

In yet another aspect, the present invention provides a pharmaceutical composition, which comprises the anti-CTLA-4 antibody or the antigen-binding fragment thereof disclosed herein, the polynucleotide disclosed herein, the expression vector disclosed herein, the host cell disclosed herein, and a pharmaceutically acceptable carrier or excipient. It should be understood that the anti-CTLA-4 antibody or the pharmaceutical composition thereof provided herein can be integrated into a suitable carrier, an excipient and other reagents in a formulation for administration in combination, thus providing improved transfer, delivery, tolerance, etc.

The term "pharmaceutical composition" refers to a formulation which allows the biological activity of active ingredients contained therein to be present in an effective form and does not contain additional ingredients having toxicity unacceptable to a subject to which the formulation is administered.

The pharmaceutical formulation comprising the anti-CTLA-4 antibody described herein, preferably in the form of an aqueous solution or a lyophilized formulation, may be prepared by mixing the anti-CTLA-4 antibody disclosed herein having the desired purity with one or more optional pharmaceutical excipients (*Remington's Pharmaceutical Sciences*, 16*th* edition, Osol, A. Ed. (1980)).

The pharmaceutical composition or preparation disclosed herein can further comprise one or more additional active ingredients which are required for a specific indication being treated, preferably active ingredients having complementary activities that do not adversely affect one another. In some embodiments, the additional active ingredients are chemotherapeutic agents, immune checkpoint inhibitors, growth inhibitors, antibiotics or various known anti-tumor or anti-cancer agents, which are suitably present in combination in amounts that are effective for purpose intended. In some embodiments, the pharmaceutical composition disclosed herein also comprises a composition of a polynucleotide encoding the anti-CTLA-4 antibody.

In yet another aspect, the present invention provides a pharmaceutical combination, which comprises the antibody or the antigen-binding fragment thereof disclosed herein, the polynucleotide disclosed herein, the expression vector disclosed herein, the host cell disclosed herein or the pharmaceutical composition disclosed herein, and one or more additional therapeutic agents.

In yet another aspect, the present invention provides a kit, which comprises the antibody or the antigen-binding fragment thereof disclosed herein, the polynucleotide disclosed herein, the expression vector disclosed herein, the host cell disclosed herein or the pharmaceutical composition disclosed herein, and which preferably further comprises a drug delivery device.

Medical Use

In yet another aspect, the present invention provides use of the antibody or the antigen-binding fragment thereof disclosed herein, the polynucleotide disclosed herein, the expression vector disclosed herein, the host cell disclosed herein or the pharmaceutical composition disclosed herein in the manufacture of a medicament for the treatment and/or prevention of a CTLA-4-mediated disease or disorder, wherein preferably, the disease or disorder is cancer; more preferably, the cancer is selected from melanoma, renal cancer, prostate cancer, breast cancer, colon cancer, lung cancer, bone cancer, pancreatic cancer, skin cancer, head and neck cancer, uterine cancer, ovarian cancer and rectal cancer.

In yet another aspect, the present invention provides the antibody or the antigen-binding fragment thereof disclosed herein, the polynucleotide disclosed herein, the expression vector disclosed herein, the host cell disclosed herein or the pharmaceutical composition disclosed herein for use in the treatment and/or prevention of a CTLA-4-mediated disease or disorder, wherein preferably, the disease or disorder is cancer; more preferably, the cancer is selected from melanoma, renal cancer, prostate cancer, breast cancer, colon cancer, lung cancer, bone cancer, pancreatic cancer, skin cancer, head and neck cancer, uterine cancer, ovarian cancer and rectal cancer.

In yet another aspect, the present invention provides a method for treating and/or preventing a CTLA-4-mediated disease or disorder, which comprises administering to a subject in need the antibody or the antigen-binding fragment thereof disclosed herein, the polynucleotide disclosed herein, the expression vector disclosed herein, the host cell disclosed herein or the pharmaceutical composition disclosed herein, wherein preferably, the disease or disorder is cancer; more preferably, the cancer is selected from melanoma, renal cancer, prostate cancer, breast cancer, colon cancer, lung cancer, bone cancer, pancreatic cancer, skin cancer, head and neck cancer, uterine cancer, ovarian cancer and rectal cancer.

In some embodiments, the cancer or tumor disclosed herein can be selected from melanoma, renal cancer, prostate cancer, breast cancer, colon cancer, lung cancer, bone cancer, pancreatic cancer, skin cancer, head and neck cancer, uterine cancer, ovarian cancer and rectal cancer.

In some embodiments, the routes of administration of the present invention include, but are not limited to, oral administration, intravenous administration, subcutaneous administration, intramuscular administration, intra-arterial administration, intra-articular administration (e.g., in arthritic joints), administration by inhalation or aerosol delivery, intratumoral administration, and the like.

The present invention also provides co-administration of a therapeutically effective amount of one or more therapies (e.g., treatment modalities and/or additional therapeutic agents) to a subject. In some embodiments, the therapies include surgical treatment and/or radiation therapy.

In some embodiments, the methods or uses provided herein also comprise administering to the individual one or more therapies (e.g., treatment modalities and/or additional therapeutic agents). The antibody disclosed herein may be used alone or in combination with other therapeutic agents in a therapy. For example, the antibody may be co-administered with at least one additional therapeutic agent. For example, a PD-1 antibody, a PD-L1 antibody and a LAG-3 antibody.

The present application also provides use of the anti-CTLA-4 antibody or the antigen-binding fragment thereof, the polynucleotide, the vector, the host cell, the immunoconjugate of the antibody or the fragment thereof, or the pharmaceutical composition described above in the manufacture of a medicament for the prevention and/or treatment of a CTLA-4-related disease or disorder, such as a tumor.

In some embodiments, the tumor disclosed herein can be colon cancer, melanoma, mesothelioma, renal cell carcinoma, lymphoma, advanced solid tumors or metastases thereof, and the like.

Methods for Diagnosis and Detection

In yet another aspect, the present invention provides a method for detecting the presence of CTLA-4 in a sample using the antibody or the antigen-binding fragment thereof disclosed herein. The term "detection" as used herein includes quantitative or qualitative detection. In some embodiments, the sample is a biological sample. In certain embodiments, the biological sample is blood, serum, or other liquid samples of biological origin. In certain embodiments, the biological sample includes cells or tissues.

The present invention includes any combinations of the specific embodiments described. Further embodiments of the present invention and the full scope of applicability will become apparent from the detailed description provided below. However, it should be understood that the detailed description and the specific examples, while indicating preferred embodiments of the present invention, are provided by way of illustration only, as various changes and modifications within the spirit and scope of the present invention will become apparent to those skilled in the art from the detailed description. All publications, patents and patent applications cited herein, including the citations, are hereby incorporated by reference in their entirety for all purposes.

The compounds of the present invention can be prepared using a variety of synthesis methods well known to those skilled in the art, including the specific embodiments listed below, embodiments formed by combinations thereof with other methods, and equivalents well known to those skilled in the art; preferred embodiments include, but are not limited to, the examples of the present invention.

The following abbreviations are used in this application: his-tag for histidine tag: Fc tag for crystallizable fragment tag; ECD for extracellular domain; PEI for polyethyleneimine; BSA for bovine serum albumin; PBS for phosphate-buffered saline; CFSE for carboxyfluorescein diacetate succinimidyl ester; APC for allophycocyanin; NA-PE for phycoerythrin-labeled neutral avidin; PE for phycoerythrin; TMB for 3,3',5,5'-tetramethylbenzidine; HEPES for hydroxyethylpiperazine ethanethiosulfonic acid buffer; and DTT for dithiothreitol.

EXAMPLES

The present invention is illustrated by the following examples, which, however, are not intended to be limiting in any way. The present invention has been described in detail, and the specific embodiments are also disclosed. Any modifications, equivalents, improvements, etc., made to the specific embodiments of the present invention without departing from the spirit and scope of the present invention shall fall within the protection scope of the present invention. The methods and materials used in the examples are, unless otherwise indicated, conventional in the art.

Example 1. Preparation of Recombinant Proteins for Anti-CTLA-4 Antibody Preparation and Testing 1.1 Preparation of Human CTLA-4 Extracellular Domain Recombinant Proteins The human CTLA-4 (huCTLA-4) gene (Sino Biological) was obtained. The gene sequence of huCTLA-4 ECD was under NCBI accession No. NM_005214.3. Corresponding primers are designed. The gene encoding huCTLA-4 ECD was obtained by PCR amplification. The restriction endonuclease sites BSPQI and NotI were added upstream and downstream of the gene, respectively. The fragments obtained from the PCR amplification were digested with enzymes BSPQI and NotI and cloned into a eukaryotic expression plasmid system (HX1). 293 cells were transfected with the plasmid by PEI and cultured for 6 days, and then the culture supernatant was collected and purified to give recombinant proteins huCTLA-4 ECD (his-tag) and huCTLA-4 ECD (FC) separately.

1.2 Preparation of Cynomolgus Monkey CTLA-4 Extracellular Domain Recombinant Protein The cynomolgus monkey CTLA-4 (cynoCTLA-4) gene (Sino Biological) was obtained. The gene sequence of cynoCTLA-4 ECD was under NCBI accession No. 102115124. Corresponding primers are designed. The gene encoding cynoCTLA-4 ECD was obtained by PCR amplification. The restriction endonuclease sites BSPQI and NheI were added upstream and downstream of the gene, respectively. The fragments obtained from the PCR amplification were digested with enzymes BSPQI and NheI and cloned into a eukaryotic expression plasmid system (HX1). 293 cells were transfected with the plasmid by PEI and cultured for 6 days, and then the culture supernatant was collected and purified to give a recombinant protein cynoCTLA-4 ECD (FC).

1.3 Preparation of Human CD80 Extracellular Domain Recombinant Proteins

The human CD80 (huCD80) gene (Sino Biological) was obtained. The gene sequence of huCD80 ECD was under NCBI accession No. NM_005191.3. Corresponding primers are designed. The gene encoding huCD80 ECD was obtained by PCR amplification. The restriction endonuclease sites EcoRI and NheI were added upstream and downstream of the gene, respectively. The fragments obtained from the PCR amplification were digested with enzymes EcoRI and NheI and cloned into a eukaryotic expression plasmid system (MX2-FC). 293 cells were transfected with the plasmid by PEI and cultured for 6 days, and then the culture supernatant was collected and purified by affinity chromatography to give a recombinant protein huCD80 ECD (Fc tag).

1.4 Preparation of Human CD86 Extracellular Domain Recombinant Proteins

The human CD86 (huCD86) gene (Sino Biological) was obtained. The gene sequence of huCD86 ECD was under NCBI accession No. NM_006889.3. Corresponding primers are designed. The gene encoding huCD86 ECD was obtained by PCR amplification. The restriction endonuclease site SapI was added upstream and downstream of the gene. The fragments obtained from the PCR amplification were digested with enzyme SapI and cloned into a eukaryotic expression plasmid system (HX1-FC). 293 cells were transfected with the plasmid by PEI and cultured for 6 days, and then the culture supernatant was collected and purified by affinity chromatography to give a recombinant protein huCD86 ECD (Fc tag).

Example 2. Preparation of Mouse Hybridoma Cells 2.1 Animal Immunization

HuCTLA-4 ECD (his tag) was used as an antigen to immunize 5 mice (purchased from Simonsen Laboratories of Gilroy, female BALB/c. 8 weeks). After primary immunization (50 µg/mouse), booster immunization (25 µg/mouse) was performed once every other week or every 2 weeks. Immunization was performed 6 times in total.

2.2 Cell Fusion

Four days after the last booster immunization, the inguinal lymph nodes, the popliteal lymph nodes and the spleens of the mice were collected and ground in normal saline, and then the suspension rich in lymphocytes was collected and fused with mouse myeloma Sp2/0 (from ATCC) using the conventional electrotransfection method. The fusion product was cultured in a DMEM complete medium containing 1:50 HAT (hypoxanthine, amethopterin and thymidine) for 5 days so as to obtain successful fusion cells (i.e., hybridoma cells) by screening. Then the medium was changed to a DMEM complete medium containing 1:50 HT (hypoxanthine and thymidine), and the culture continued until the end of the screening.

The formula of the DMEM complete medium was as follows: 15% FBS (fetal bovine serum)+1:50 L-Glutamine+ 100 U/mL penicillin-streptomycin+1:100 OPI (oxaloacetic acid, pyruvic acid and insulin). The incubator conditions were 8% $CO_2$, 37° C.

Example 3. Mouse Hybridoma Cell Screening and Performance Tests of the Obtained Anti-CTLA-4 Murine Antibodies From 11,520 strains of polyclonal hybridoma cells, 461 strains of hybridoma cells secreting antibodies capable of binding to huCTLA-4 Fc were obtained by ELISA screening. 219 of the 461 strains of hybridoma cells expressed antibodies capable of binding to cynoCTLA-4 Fc. ForteBio-based blocking analyses showed that antibodies expressed by 24 of the 219 strains of hybridoma cells were capable of blocking the binding of huCTLA-4 to huCD86. By further FACS-based blocking analysis, 11 strains of polyclonal hybridoma cells expressing antibodies with huCD80-blocking activity were obtained from the 24 strains. They were then subcloned. Finally, a total of 7 strains of monoclonal hybridoma cells were obtained from the above hybridoma cell strains by screening, and antibodies secreted by them were separately purified and analyzed. Further, the mRNA of each of the 7 strains of monoclonal hybridoma cells was extracted and its coding sequences for antibody variable regions were determined. The 7 hybridoma antibodies preliminarily obtained by screening were numbered 1B2.1, 1A5.1, 3E6.1, 3E6.2, 4B7.1, 4E7.1 and 5B9.1. Further, it was confirmed that the 7 hybridoma antibodies did not significantly cross-react with other antigens (TIGIT and BTLA).

The experimental methods and results are shown below.

3.1 FACS Detection of Hybridoma Antibodies' Blocking of Binding of huCTLA-4 to huCD80

HuCTLA-4-expressing CHO cells (from ATCC) were incubated with the above hybridoma antibodies or a control antibody (ipilimumab) diluted 1:3 from an initial antibody concentration of 5 µg/mL to different concentrations. Then 5 µg/mL biotin-labeled huCD80 was added, and detection was performed using NA-PE.

As shown in FIG. 1, the detection results indicate that 1A5.1, 3E6.1, 3E6.2, 4B7.1, 4E7.1 and 5B9.1 were all able to significantly block the binding of huCTLA-4 to huCD80 except for 1B2.1.

3.2 Biological Antagonistic Activity of Hybridoma Antibodies Against huCTLA-4

Different concentrations of diluted hybridoma antibodies (1B2.1, 1A5.1, 3E6.1, 3E6.2, 4B7.1, 4E7.1 and 5B9.1) were mixed with huCTLA-4-expressing Jurkat effector cells (Promega) and Raji APC target cells (Promega) (ipilimumab as control antibody) to detect the Jurkat effector cells' luciferase expression mediated by the downstream signaling pathway and thus to determine the biological activity of the hybridoma antibodies.

Figure 2:
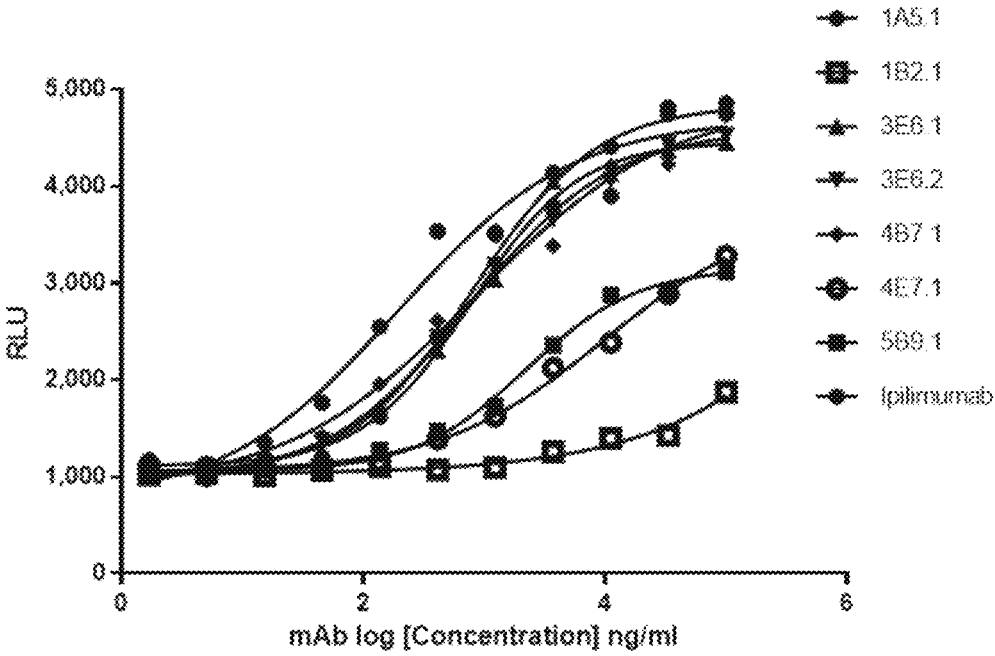
FIG. 2: the biological antagonistic activity of hybridoma anti-CTLA-4 antibodies against huCTLA-4.

As shown in FIG. 2, 1B2.1 had lower antagonistic biological activity against huCTLA-4, and 4E7.1, 5B9.1, 3E6.1, 3E6.2, 4B7.1 and 1A5.1 all had relatively good antagonistic biological activity against huCTLA-4.

3.3 Cross-Reactions of Hybridoma Antibodies with Other Antigens (TIGIT and BTLA)

293T-TIGIT, 293T-CTLA4, 293T-BTLA or 293T mother cells were incubated with 1 µg of hybridoma antibody 1B2.1, 1A5.1, 3E6.1, 3E6.2, 4B7.1, 4E7.1 or 5B9.1 or control antibody at 4° C. for 30 min. Then the above cell mixture was incubated with 5 µL of APC-labeled murine secondary antibody (Southern Biotech) at 4° C. for 20 min, and the secondary antibody bound onto the cells was detected. The control antibody was selected from commercially available CTLA4 monoclonal antibody L3D10 (BioLegend) and TIGIT monoclonal antibody MBSA43 (eBioscience).

Figure 3:
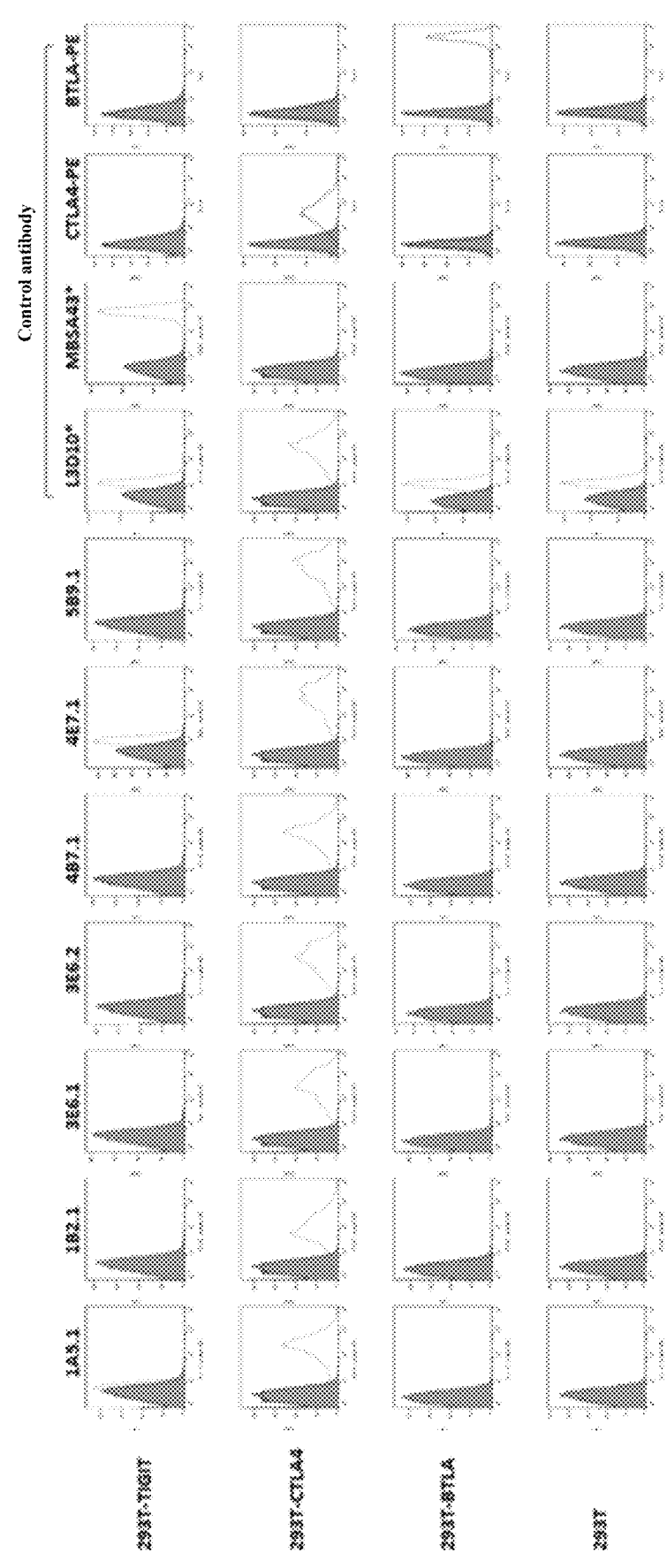
FIG. 3: the cross-reactions of hybridoma anti-CTLA-4 antibodies with other antigens (TIGIT and BTLA).

As shown in FIG. 3, the above antibodies did not significantly cross-react with other antigens (TIGIT and BTLA).

3.4 Affinity of hybridoma antibodies for huCTLA-4 As shown in Table 1, the affinity of the above hybridoma antibodies for huCTLA-4 was determined using a ForteBio instrument. It was confirmed that the hybridoma antibodies prepared above were able to specifically bind to huCTLA-4.

TABLE 1

| Affinity of hybridoma antibodies for huCTLA-4 | | | | | | |
|---|---|---|---|---|---|---|
| Sample | 1A5.1 | 1B2.1 | 3E6.1 | 3E6.2 | 4B7.1 | 4E7.1 | 5B9.1 |
| $K_D$(M) | 1.74E−09 | 1.02E−9 | <1.0E−12 | 5.24E−10 | 5.70E−10 | 1.47E−09 | <1.0E−12 |

Example 4. Sequencing of Variable Regions of Anti-CTLA-4 Murine Antibodies (Shown According to the Kabat or IMGT Scheme)

The corresponding DNA sequences coding for the variable regions of the anti-CTLA-4 murine antibodies were determined using a degenerate primer PCR-based method. Briefly, the hybridoma cell strains were separately expanded and centrifuged at 1000 rpm, and the cells were collected. Total RNA was extracted with Trizol. A first-strand cDNA was synthesized using the total RNA as a template, and then the DNA sequences coding for variable regions were amplified by PCR using the first-strand cDNA as a subsequent template. The PCR primer used was based on an Ig-primer set. The PCR products were recovered and purified. The products of the amplification were sequenced to obtain the amino acid sequences of the heavy chain variable regions and light chain variable regions of the anti-CTLA-4 murine antibodies.

The NCBI Ig-Blast (http://www.ncbi.nlm.nih.gov/projects/igblast/) was used to search for consensus sequences in germline and rearranged Ig variable region sequence databases. The amino acid sequences of complementarity-determining regions (CDRs) were identified by sequence annotation and by Internet-based sequence analysis (http://www.imgt.org/IMGT_vquest/vquest and http://www.ncbi.nlm.nih.gov/igblast/), based on the Kabat system (Wu, T. T and Kabat, E. A. 1970 *J. Exp. Med.*, 132:211-250) and the IMGT system (Lefranc M.-P. et al., 1999 *Nucleic Acids Research*, 27, 209-212).

The amino acid sequences of the light chain variable regions and heavy chain variable regions and CDRs of the selected anti-CTLA-4 murine antibodies are shown in Table 2.

TABLE 2

| Amino acid sequences of CDRs and variable regions of anti-CTLA-4 murine antibodies (KABAT scheme) | | | | | |
|---|---|---|---|---|---|
| | 1A5.1 | 3E6.1 | 4B7.1-1 | 4B7.1-2 | 5B9.1 |
| HCDR1 | SEQ ID NO: 1 | SEQ ID NO: 7 | SEQ ID NO: 13 | SEQ ID NO: 19 | SEQ ID NO: 22 |
| HCDR2 | SEQ ID NO: 2 | SEQ ID NO: 8 | SEQ ID NO: 14 | SEQ ID NO: 20 | SEQ ID NO: 23 |
| HCDR3 | SEQ ID NO: 3 | SEQ ID NO: 9 | SEQ ID NO: 15 | SEQ ID NO: 21 | SEQ ID NO: 24 |
| LCDR1 | SEQ ID NO: 4 | SEQ ID NO: 10 | SEQ ID NO: 16 | SEQ ID NO: 16 | SEQ ID NO: 25 |
| LCDR2 | SEQ ID NO: 5 | SEQ ID NO: 11 | SEQ ID NO: 17 | SEQ ID NO: 17 | SEQ ID NO: 26 |
| LCDR3 | SEQ ID NO: 6 | SEQ ID NO: 12 | SEQ ID NO: 18 | SEQ ID NO: 18 | SEQ ID NO: 27 |
| VH | SEQ ID NO: 28 | SEQ ID NO: 30 | SEQ ID NO: 32 | SEQ ID NO: 34 | SEQ ID NO: 35 |
| VL | SEQ ID NO: 29 | SEQ ID NO: 31 | SEQ ID NO: 33 | SEQ ID NO: 33 | SEQ ID NO: 36 |

Note:
4B7.1-1 and 4B7.1-2 were both derived from 4B7.1.

Example 5. Construction of Anti-CTLA-4 Chimeric Antibodies

According to the assessment results of Example 3, the light chain variable regions and heavy chain variable regions of the anti-CTLA-4 murine antibodies 1A5.1, 3E6.1, 4B7.1 and 5B9.1 were selected to construct anti-CTLA-4 chimeric antibodies.

The coding sequences for the heavy chain constant region Fc and the light chain constant region κ were cloned from human B lymphocytes (from Beijing Blood Institute) and introduced into the pCDNA3.1 plasmid. The coding sequences for the heavy chain variable regions and light chain variable regions of the anti-CTLA-4 murine antibodies were synthesized by Genescript. The coding sequences for the heavy chain variable regions of various anti-CTLA-4 murine antibodies were digested with enzyme BSPQI and the coding sequences for their light chain variable regions were digested with enzyme BSPQI. Then the digested sequences were introduced, in various combinations as shown in Table 3, into the pCDNA3.1 plasmid into which the coding sequences for the constant regions had been introduced, and correct clones were determined by sequencing. Various chimeric heavy and light chain expression plasmids were mixed and paired and used to transfect expression cells (CHOK1 18, Suzhou Junmeng). Twenty chimeric antibodies were obtained, and their numbers and amino acid sequences of corresponding variable regions are shown in detail in Table 3.

TABLE 3

| Numbering of chimeric antibodies and sources of their heavy chain variable regions and light chain variable regions | | | | | |
|---|---|---|---|---|---|
| | 1A5.1 VH | 3E6.1 VH | 4B7.1-1 VH | 4B7.1-2 VH | 5B9.1 VH |
| 1A5.1 VL | JS007-1 | JS007-5 | JS007-9 | JS007-13 | JS007-17 |
| 3E6.1 VL | JS007-2 | JS007-6 | JS007-10 | JS007-14 | JS007-18 |
| 4B7.1-1 VL | JS007-3 | JS007-7 | JS007-11 | JS007-15 | JS007-19 |
| 5B9.1 VL | JS007-4 | JS007-8 | JS007-12 | JS007-16 | JS007-20 |

Example 6. Chimeric Antibody Screening

The optimal chimeric antibodies were obtained by screening according to the binding of the chimeric antibodies in Table 3 to huCTLA-4, their abilities to block the binding of huCTLA-4 to CD80/CD86, and their antagonistic biological activity against huCTLA-4. The experimental methods and results are shown below.

6.1 ELISA Detection of Binding of Chimeric Antibodies to huCTLA-4

HX1 hCTLA4 his was diluted with PBS (Hyclone) to 1.0 μg/mL, and the dilution was added to a microplate at 100 μL/well. The plate was let stand in an incubator at 37° C. and coated for 90 min and then washed, and 2% BSA was added to the plate at 200 μL/well. The plate was incubated in an incubator at 37° C. for 90 min and then washed. The chimeric antibodies in Table 3 and the control antibody (ipilimumab) were diluted with a diluent (2% BSA) to 1000 ng/mL. The dilution performed each time was not higher than 10-fold. Then, the chimeric antibodies and the control antibody were serially diluted 2.5-fold on a sample dilution plate. All the chimeric antibody solutions and the control antibody solution were added to a microplate at 100 μL/well. The plate was incubated in an incubator at 37° C. for 60 min and then washed. A horseradish peroxidase (HRP)-conjugated goat anti-human antibody IgG (Sigma, Catalog No. A0170) (Fc specific) was diluted 5000-fold with 2% BSA, and the dilution was added to the microplate at 100 μL/well. The plate was incubated in an incubator at 37° C. for 60 min and then washed. The color development solution TMB was added at 100 μL/well, during which bubbles were avoided. Color development was allowed at 37° C. for 15 min in the dark and then terminated by adding 2 M hydrochloric acid solution at 100 μL/well, during which bubbles were avoided. Reading (wavelength: 450/620 nm) was done within 10 min using a microplate reader.

Figure 4:
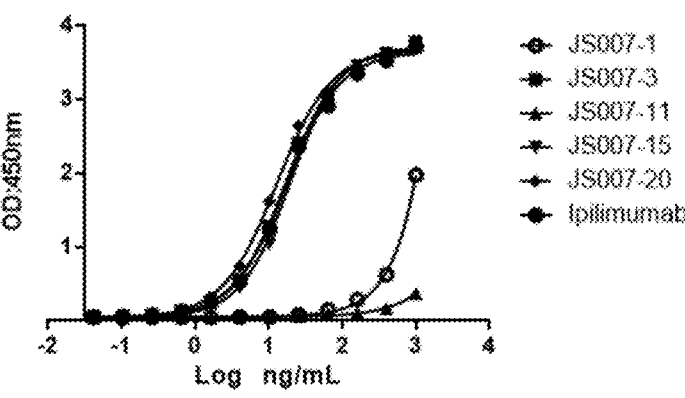
FIG. 4: ELISA detection of the binding of chimeric anti-CTLA-4 antibodies to huCTLA-4.

As shown in FIG. 4, the JS007-3, JS007-15 and JS007-20 chimeric antibodies bound to huCTLA-4 well, with $EC_{50}$ of 17.23 ng/ml, 19.72 ng/ml and 12.88 ng/mL, respectively; they were comparable or superior to the control antibody in this respect.

6.2 FACS Detection of Binding of Chimeric Antibodies to huCTLA-4-Expressing Cells HuCTLA-4-expressing cells (constructed in-house by Junmeng; CHO from ATCC) were co-incubated with each of the chimeric antibodies in Table 3 and the control antibody (ipilimumab) (serially diluted 3-fold from an initial concentration of 10 μg/mL) at room temperature for 30 min, and then a fluorescent secondary antibody (PE-anti human IgG) was added to detect the binding of the chimeric antibodies to the huCTLA-4-expressing cells.

Figure 5:
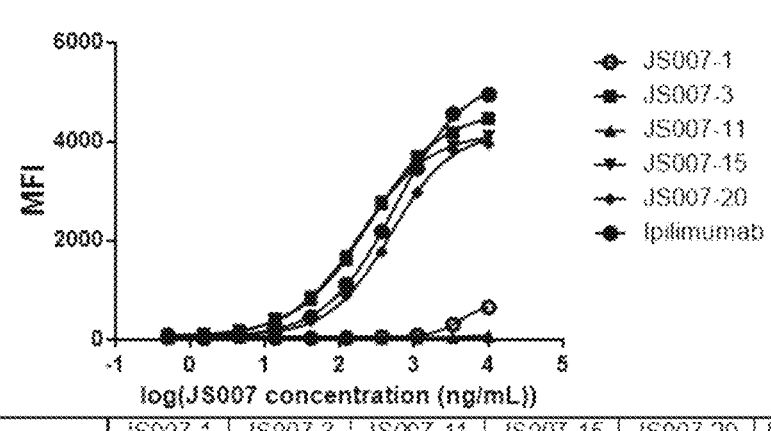
FIG. 5: FACS detection of the binding of chimeric anti-CTLA-4 antibodies to huCTLA-4-expressing cells.

As shown in FIG. 5, the JS007-3, JS007-15 and JS007-20 chimeric antibodies bound to the huCTLA-4-expressing cells well, with $EC_{50}$ of 249.4 ng/mL, 189.4 ng/ml and 486.1 ng/ml, respectively; they were all superior to the control antibody ipilimumab in this respect.

6.3 ELISA determination of abilities of chimeric antibodies to block binding of huCTLA-4 to CD80 HX1 huCTLA4 his was diluted with PBS (Hyclone) to 1.0 μg/mL, and the dilution was added to a microplate at 100 μL/well. The plate was let stand in an incubator at 37° C. and incubated for 90 min and then washed, and 2% BSA was added to the plate at 200 μL/well. The plate was incubated in an incubator at 37° C. for 90 min and then washed. MX2 hCD80 Fc was diluted with 2% BSA to 5.0 μg/mL, and the dilution was used to dilute samples. The chimeric antibodies and the control antibody ipilimumab were diluted to 100 μg/mL. The dilution performed each time was not higher than 10-fold. Then, the chimeric antibodies and the control antibody were serially diluted 2.5-fold on a sample dilution plate. All the chimeric antibody solutions and the control antibody solution were added to a microplate at 100 μL/well. The plate was incubated in an incubator at 37° C. for 90 min and then washed. An HRP-conjugated goat anti-mouse antibody IgG (Fc specific) (Sigma, Catalog No. A2554) was diluted 5000-fold with 2% BSA, and the dilution was added to the microplate at 100 μL/well. The plate was incubated in an incubator at 37° C. for 60 min and then washed. The color development solution TMB was added at 100 μL/well, during which bubbles were avoided. Color development was allowed at 37° C. for 15 min in the dark and then terminated by adding 2 M hydrochloric acid solution at 100 μL/well, during which bubbles were avoided. Reading (wavelength: 450/620 nm) was done within 10 min using a microplate reader.

Figure 6:
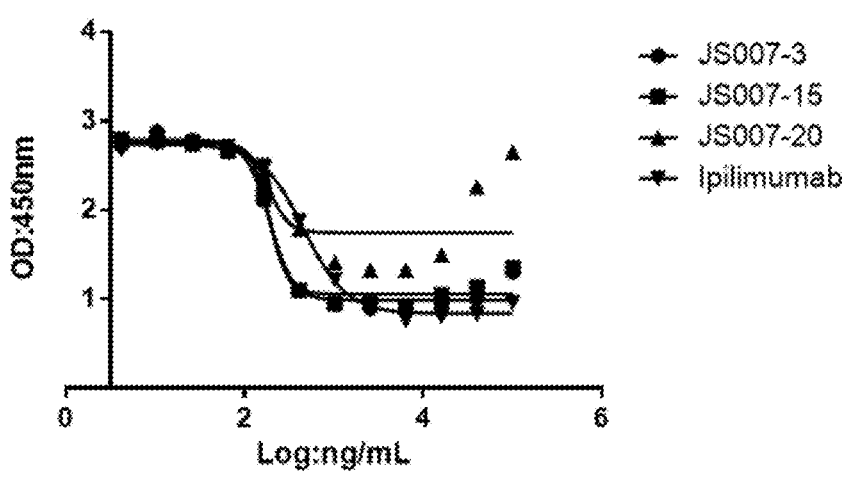
FIG. 6: ELISA determination of the abilities of chimeric anti-CTLA-4 antibodies to block the binding of huCTLA-4 to CD80.

As shown in FIG. 6, the JS007-3, JS007-15 and JS007-20 chimeric antibodies were all able to block the binding of huCTLA-4 to CD80, with $IC_{50}$ of 189.7 ng/ml, 189.7 ng/ml and 186.6 ng/ml, respectively, and they were all significantly superior to the control antibody ipilimumab in this respect.

6.4 FACS Detection of Abilities of Chimeric Antibodies to Block Binding of huCTLA-4 to CD80/CD86-Expressing Cells The chimeric antibodies in Table 3 and the control antibody ipilimumab (serially diluted 3-fold from an initial concentration of 30 μg/mL) were each added to CD80- or CD86-expressing CHO cells (constructed in-house by Junmeng) together with a certain concentration of huCTLA4 recombinant protein. After they were co-incubated at room temperature for 30 min, a fluorescent secondary antibody (PE-anti human IgG4) (Southern biotech) was added to determine the abilities of the chimeric antibodies to block the binding of huCTLA-4 to the CD80/CD86-expressing cells.

Figure 7A:
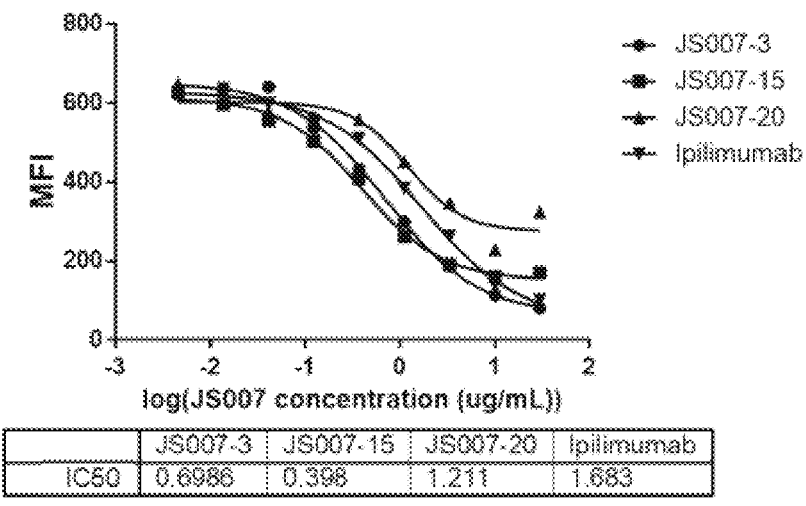
FIG. 7: 7a: FACS determination of the abilities of chimeric anti-CTLA-4 antibodies to block the binding of huCTLA-4 to CD80-expressing cells; 7b: FACS determination of the abilities of chimeric anti-CTLA-4 antibodies to block the binding of huCTLA-4 to CD86-expressing cells.
Figure 7B:
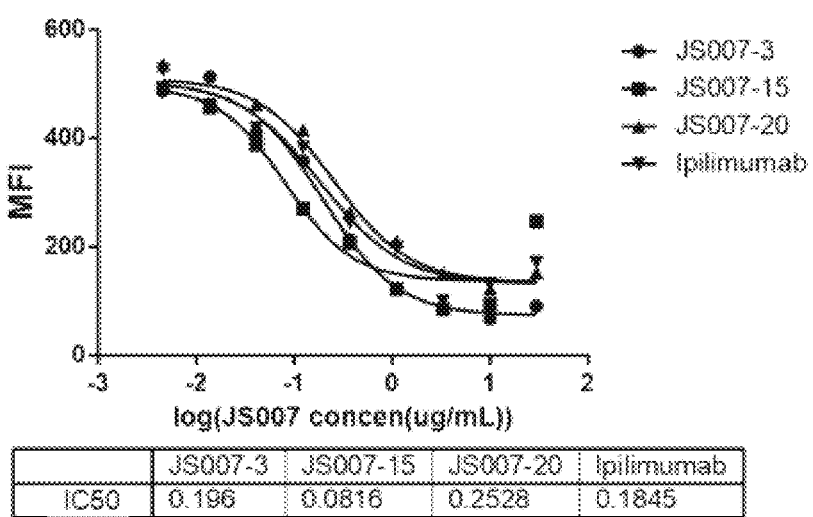

As shown in FIGS. 7a and 7b, the JS007-3, JS007-15 and JS007-20 chimeric antibodies were all able to block the binding of huCTLA-4 to CD80/CD86-expressing cells. Their $IC_{50}$ values for blocking the binding of huCTLA-4 to CD80-expressing cells were 0.6986 ng/ml. 0.398 ng/mL and 1.211 ng/mL, respectively; they were significantly superior to the control antibody ipilimumab in this respect. Their $IC_{50}$ values for blocking the binding of huCTLA-4 to CD86-expressing cells were 0.196 ng/ml, 0.0816 ng/ml and 0.2528 ng/ml; they were comparable or significantly superior to the control antibody ipilimumab in this respect.

6.5 Luciferase Assays for Determining Biological Antagonistic Activity of Chimeric Antibodies Against huCTLA-4

Different concentrations of diluted chimeric antibodies (JS007-3, JS007-15 and JS007-20) were mixed with huCTLA-4-expressing Jurkat effector cells and Raji APC target cells to detect the Jurkat effector cells' luciferase expression mediated by the downstream signaling pathway and thus to determine the antagonistic biological activity of the chimeric antibodies against huCTLA-4.

Figure 8:
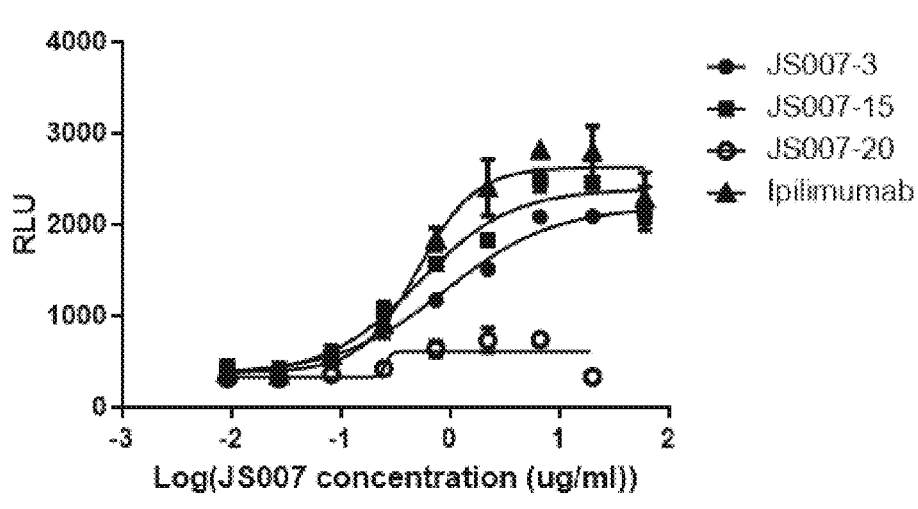
FIG. 8: Luciferase assays for determining the biological antagonistic activity of chimeric anti-CTLA-4 antibodies against huCTLA-4.

As shown in FIG. 8, the JS007-3, JS007-15 and JS007-20 chimeric antibodies have relatively good antagonistic biological activity against huCTLA-4.

Example 7. Humanization of Antibody Variable Regions

For humanization of antibody variable regions, human IgG genes homologous to the cDNA sequence of the murine antibody variable regions were retrieved in the human immunoglobulin gene database of the NCBI (http://www.ncbi.nlm.nih.gov/igblast/). The amino acid sequences of CDRs of the variable regions and their boundaries were then determined as per the Kabat numbering system or the IMGT numbering system. Human IGHV and IGKV with high homology to the variable regions of the murine antibody were selected as templates for humanization and antibody variable regions were humanized by CDR grafting.

Humanization was carried out based on the variable region sequences of the antibodies secreted by the hybridoma cells obtained above. Briefly, the humanization comprises the following steps: A. comparing the gene sequence of the antibody secreted by each hybridoma cell with the gene sequence of the human embryonic antibody to find out a sequence with high homology; B. analyzing and investigating HLA-DR affinity, and selecting a human embryonic framework region sequence with low affinity; C. analyzing the variable regions and their periphery framework region amino acid sequences by using a computer simulation technology and applying molecular docking to investigate their spatial and stereo combination modes; analyzing the key amino acid individuals that can interact with hCTLA-4 and maintain the spatial framework in the gene sequence of the antibody secreted by each hybridoma cell by calculating electrostatic force, Van der Waals' force, hydrophilicity and hydrophobicity, and entropy value and grafting them to the selected human embryonic gene framework regions, and mapping the amino acid sites of the framework regions which must be retained; and D. performing back mutation on residues that are buried, residues that directly interact with CDR regions, and residues that have a significant effect on the conformation of VL and VH, on the basis of the three-dimensional structures of murine antibodies, and optimizing amino acid residues that lead to chemical instability of the CDR regions of antibodies. The optimization results are as follows:

```
HCDR2:
                                            (SEQ ID NO: 2)
YIGYDGSNYYNPSLKN
was optimized into (SEQ ID NO: 37)
YIGYDGSNYYNPSLKS;

HCDR3:
                                            (SEQ ID NO: 3)
NYYSGYFDF
was optimized into (SEQ ID NO: 38)
NYYSGYFDS;

HCDR2:
                                            (SEQ ID NO: 20)
YIGYDGSNNYNPSLKN
was optimized into (SEQ ID NO: 39)
YIGYDGSNNYNPSLKS;

LCDR1:
                                            (SEQ ID NO: 16)
KASQNVGTYVA
was optimized into (SEQ ID NO: 40)
RASQNVGTYVA;

LCDR1:
                                            (SEQ ID NO: 16)
KASQNVGTYVA
was optimized into (SEQ ID NO: 41)
QASQNVGTYVA.

On this basis, the following humanized anti-CTAL-4 antibody variable
regions are obtained:
1A5VH-1:
                                               SEQ ID NO: 42
QVQLQESGPGLVKPSQTLSLTCTVSGYSISSGYYWNWIRQHPGKGLEWIGYIGYDGSNYYNPSLK

SRVTISRDTSKNQFSLKLSSVTAADTAVYFCARNYYSGYFDFWG QGTTLTVSS

1A5VH-2:
                                               SEQ ID NO: 43
QVQLQESGPGLVKPSQTLSLTCTVSGYSITSGYYWNWIRQHPGKGLEWIGYIGYDGSNYYNPSLK

SRVTISRDTSKNQFSLKLSSVTAADTAVYFCARNYYSGYFDFWGQGTTLTVSS

1A5VH-3:
                                               SEQ ID NO: 44
QVQLQESGPGLVKPSETLSLTCTVTGYSITSGYYWNWIRQPAGKGLEWIGYIGYDGSNYYNPSLK

SRVTISRDTSKNQFSLKLSSVTAADTAVYFCARNYYSGYFDFWG QGTTLTVSS

1A5VH-4:
                                               SEQ ID NO: 45
QVQLQESGPGLVKPSQTLSLTCAVSGYSITSGYYWNWIRQHPGKGLEWIGYIGYDGSNYYNPSLK

SRVTISRDTSKNQFSLKLSSVTAADTAVYFCARNYYSGYFDFWGQGTTLTVSS
```

1A5VH-5:

SEQ ID NO: 46
QVQLQESGPGLVKPSQTLSLTCAVSGYSISSGYYWNWIRQPPGKGLEWIGYIGYDGSNYYNPSLK

SRVTMSVDTSKNQFSLKLSSVTAVDTAVYYCARNYYSGYFDSWGQGTTVTVSS

1A5VH-6:

SEQ ID NO: 47
QVQLQESGPGLVKPSQTLSLTCAVSGYSISSGYYWNWIRQFPGKGLEWMGYIGYDGSNYYNPSL

KNRVTMSVDTSKNQFSLKLSSVTAVDTAVYYCARNYYSGYFDSWGQGTTVTVSS

1A5VH-7:

SEQ ID NO: 48
QVQLQESGPGLVKPSQTLSLTCAVSGYSISSGYYWNWIRQPPGKGLEWIGYIGYDGSNYYNPSLK

SRITISRDTSKNQFSLKLSSVTAVDTAVYYCARNYYSGYFDSWG QGTTVTVSS

4B7VH2-1:

SEQ ID NO: 49
QVQLQESGPGLVKPSQTLSLTCTVSGYSITSGYYWNWIRQHPGKGLEWIGYIGYDGSNNYNPSLK

SRVTISRDTSKNQFSLKLSSVTAADTAVYYCARDYYSGYFDSWGQGTTLTVSS

4B7VH2-2:

SEQ ID NO: 50
QVQLQESGPGLVKPSQTLSLTCTVSAYSITSGYYWNWIRQHPGKGLEWIGYIGYDGSNNYNPSLK

SRVTISRDTSKNQFSLKLSSVTAADTAVYYCARDYYSGYFDSWGQGTTLTVSS

4B7VH2-3:

SEQ ID NO: 51
QVQLQESGPGLVKPSETLSLTCTVSGYSITSGYYWNWIRQPPGKGLEWIGYIGYDGSNNYNPSLK

SRVTISRDTSKNQFSLKLSSVTAADTAVYYCARDYYSGYFDSW GQGTTLTVSS

4B7VH2-4:

SEQ ID NO: 52
QVQLQESGPGLVKPSQTLSLTCAVSAYSITSGYYWNWIRQHPGKGLEWIGYIGYDGSNNYNPSLK

SRVTISRDTSKNQFSLKLSSVTAADTAVYYCARDYYSGYFDSWGQGTTLTVSS

4B7VH2-5:

SEQ ID NO: 53
QVQLQESGPGLVKPSQTLSLTCAVSGYSITSGYYWNWIRQPPGKGLEWIGYIGYDGSNNYNPSLK

NRVTMSVDTSKNQFSLKLSSVTAVDTAVYYCARDYYSGYFDSWGQGTTVTVSS

4B7VL-1:

SEQ ID NO: 54
DIVMTQSPDSLAVSLGERATINCKASQNVGTYVAWYQQKPGQPPKPLIYSTSYRYSGVPDRFSGS

GSGTDFTLTISSLQAEDVAVYFCHQYDTYPLTFGAGTKLELK

4B7VL-2:

SEQ ID NO: 55
DIQMTQSPSSLSASVGDRVTITCRASQNVGTYVAWYQQKPGKVPKPLIYSTSYRYSGVPSRFSGS

GSGTDFTLTISSLQPEDVATYFCHQYDTYPLTFGAGTKLELK

4B7VL-3:

SEQ ID NO: 56
DIQMTQSPSSLSASVGDRVTITCRASQNVGTYVAWYQQKPGKAPKPLIYSTSYRYSGVPSRFSGS

GSGTDFTLTISSLQPEDFATYFCHQYDTYPLTFGAGTKLELK

4B7VL-4:

SEQ ID NO: 57
DIQMTQSPSFLSASVGDRVTITCRASQNVGTYVAWYQQKPGKAPKPLIYSTSYRYSGVPSRFSGS

GSGTEFTLTISSLQPEDFATYFCHQYDTYPLTFGAGTKLELK

4B7VL-5:

SEQ ID NO: 58
DIQMTQSPSSLSASVGDRVTITCQASQNVGTYVAWYQQKPGKAPKPLIYSTSYRYSGVPSRFSGS

GSGTDFTFTISSLQPEDIATYFCHQYDTYPLTFGAGTKLELK

-continued

```
4B7VL-6:
                                                      SEQ ID NO: 59
DIVMTQSPDSLAVSLGERATINCKASQNVGTYVAWYQQKPGQPPKLLIYSTSYRYSGVPDRFSGS

GSGTDFTLTISSLQAEDVAVYYCHQYDTYPLTFGQGTKLEIK

4B7VL-7:
                                                      SEQ ID NO: 60
EIVMTQSPATLSVSPGERATLSCRASQNVGTYVAWYQQKPGQAPRPLIYSTSYRYSGIPARFSGSG

SGTEFTLTISSLQSEDFAVYYCHQYDTYPLTFGQGTKLEIK

4B7VL-8:
                                                      SEQ ID NO: 61
DIVMTQSPDSLAVSLGERATINCKASQNVGTYVAWYQQKPGQPPKPLIYSTSYRYSGVPDRFSGS

GSGTDFTLTISSLQAEDVAVYFCHQYDTYPLTFGQGTKLEIK

4B7VL-9:
                                                      SEQ ID NO: 62
EIVMTQSPATLSVSPGERATLSCKASQNVGTYVAWYQQKPGQAPRPLIYSTSYRYSGIPARFSGSG

SGTEFTLTISSLQSEDFAVYFCHQYDTYPLTFGQGTKLEIK
```

The humanized anti-CTLA-4 antibody variable regions designed above were combined as shown in Table 4. The coding sequences for the heavy and light chain variable regions of the humanized anti-CTLA-4 antibodies were synthesized by Genscript. The coding sequences for the heavy chain variable regions and light chain variable regions of the various synthesized humanized anti-CTLA-4 antibodies were digested with Bspq I and then introduced into pCDNA3.1 plasmids containing the coding sequences for constant regions, and correct clones were determined by sequencing. The various humanized heavy chain and light chain expression plasmids were mixed and paired and used to transfect expression cells (CHOK1 18, Suzhou Junmeng). The expressed antibodies were recovered by centrifugation and purified using a conventional method to obtain 108 humanized anti-CTLA-4 antibodies, the numbering and amino acid sequences of which are shown in detail in Table 4.

Example 8. Humanized Anti-CTLA-4 Antibody Screening

The optimal humanized anti-CTLA-4 antibodies were obtained by screening according to the binding of the humanized anti-CTLA-4 antibodies to huCTLA-4, their abilities to block the binding of huCTLA-4 to CD80/CD86, and their antagonistic biological activity against huCTLA-4. The experimental methods and results are shown below.

8.1 ELISA Detection of Binding of Humanized Anti-CTLA-4 Antibodies to huCTLA-4

HX1 hCTLA4 his was diluted with PBS (Hyclone) to 1.0 μg/mL, and the dilution was added to a microplate at 100 μL/well. The plate was let stand in an incubator at 37° C. and coated for 90 min and then washed, and 2% BSA was added to the plate at 200 μL/well. The plate was incubated in an incubator at 37° C. for 90 min and then washed. The humanized anti-CTLA-4 antibodies in Table 4 and the control antibody (ipilimumab) were diluted with a diluent

TABLE 4

Numbering of humanized anti-CTLA-4 antibodies and sources of their
heavy chain variable regions and light chain variable regions

| Number | 1A5 VH1 | 1A5 VH2 | 1A5 VH3 | 1A5 VH4 | 4B7 VH2-1 | 4B7 VH2-2 | 4B7 VH2-3 |
|---|---|---|---|---|---|---|---|
| 4B7VL1 | HuJS00 7-1 | HuJS00 7-10 | HuJS00 7-19 | HuJS00 7-28 | HuJS00 7-37 | HuJS00 7-46 | HuJS00 7-55 |
| 4B7VL2 | HuJS00 7-2 | HuJS00 7-11 | HuJS00 7-20 | HuJS00 7-29 | HuJS00 7-38 | HuJS00 7-47 | HuJS00 7-56 |
| 4B7VL3 | HuJS00 7-3 | HuJS00 7-12 | HuJS00 7-21 | HuJS00 7-30 | HuJS00 7-39 | HuJS00 7-48 | HuJS00 7-57 |
| 4B7VL4 | HuJS00 7-4 | HuJS00 7-13 | HuJS00 7-22 | HuJS00 7-31 | HuJS00 7-40 | HuJS00 7-49 | HuJS00 7-58 |
| 4B7VL5 | HuJS00 7-5 | HuJS00 7-14 | HuJS00 7-23 | HuJS00 7-32 | HuJS00 7-41 | HuJS00 7-50 | HuJS00 7-59 |
| 4B7VL6 | HuJS00 7-6 | HuJS00 7-15 | HuJS00 7-24 | HuJS00 7-33 | HuJS00 7-42 | HuJS00 7-51 | HuJS00 7-60 |
| 4B7VL7 | HuJS00 7-7 | HuJS00 7-16 | HuJS00 7-25 | HuJS00 7-34 | HuJS00 7-43 | HuJS00 7-52 | HuJS00 7-61 |
| 4B7VL8 | HuJS00 7-8 | HuJS00 7-17 | HuJS00 7-26 | HuJS00 7-35 | HuJS00 7-44 | HuJS00 7-53 | HuJS00 7-62 |
| 4B7VL9 | HuJS00 7-9 | HuJS00 7-18 | HuJS00 7-27 | HuJS00 7-36 | HuJS00 7-45 | HuJS00 7-54 | HuJS00 7-63 |

| | Number | 4B7 VH2-4 | 1A5 VH5 | 1A5 VH6 | 1A5 VH7 | 4B7 VH2-5 |
|---|---|---|---|---|---|---|
| | 4B7VL1 | HuJS00 7-64 | HuJS00 7-73 | HuJS00 7-82 | HuJS00 7-91 | HuJS00 7-100 |
| | 4B7VL2 | HuJS00 7-65 | HuJS00 7-74 | HuJS00 7-83 | HuJS00 7-92 | HuJS00 7-101 |
| | 4B7VL3 | HuJS00 7-66 | HuJS00 7-75 | HuJS00 7-84 | HuJS00 7-93 | HuJS00 7-102 |
| | 4B7VL4 | HuJS00 7-67 | HuJS00 7-76 | HuJS00 7-85 | HuJS00 7-94 | HuJS00 7-103 |
| | 4B7VL5 | HuJS00 7-68 | HuJS00 7-77 | HuJS00 7-86 | HuJS00 7-95 | HuJS00 7-104 |
| | 4B7VL6 | HuJS00 7-69 | HuJS00 7-78 | HuJS00 7-87 | HuJS00 7-96 | HuJS00 7-105 |
| | 4B7VL7 | HuJS00 7-70 | HuJS00 7-79 | HuJS00 7-88 | HuJS00 7-97 | HuJS00 7-106 |
| | 4B7VL8 | HuJS00 7-71 | HuJS00 7-80 | HuJS00 7-89 | HuJS00 7-98 | HuJS00 7-107 |
| | 4B7VL9 | HuJS00 7-72 | HuJS00 7-81 | HuJS00 7-90 | HuJS00 7-99 | HuJS00 7-108 |

(2% BSA) to 1000 ng/mL. The dilution performed each time was not higher than 10-fold. Then, the humanized antibodies and the control antibody were serially diluted 2.5-fold on a sample dilution plate. All the humanized antibody solutions and the control antibody solution were added to a microplate at 100 µL/well. The plate was incubated in an incubator at 37° C. for 60 min and then washed. An HRP-conjugated goat anti-human antibody IgG (Fc specific) was diluted 5000-fold with 2% BSA, and the dilution was added to the microplate at 100 µL/well. The plate was incubated in an incubator at 37° C. for 60 min and then washed. The color development solution TMB was added at 100 µL/well, during which bubbles were avoided. Color development was allowed at 37° C. for 15 min in the dark and then terminated by adding 2 M hydrochloric acid solution at 100 µL/well, during which bubbles were avoided. Reading (wavelength: 450/620 nm) was done within 10 min using a microplate reader.

Figure 9:
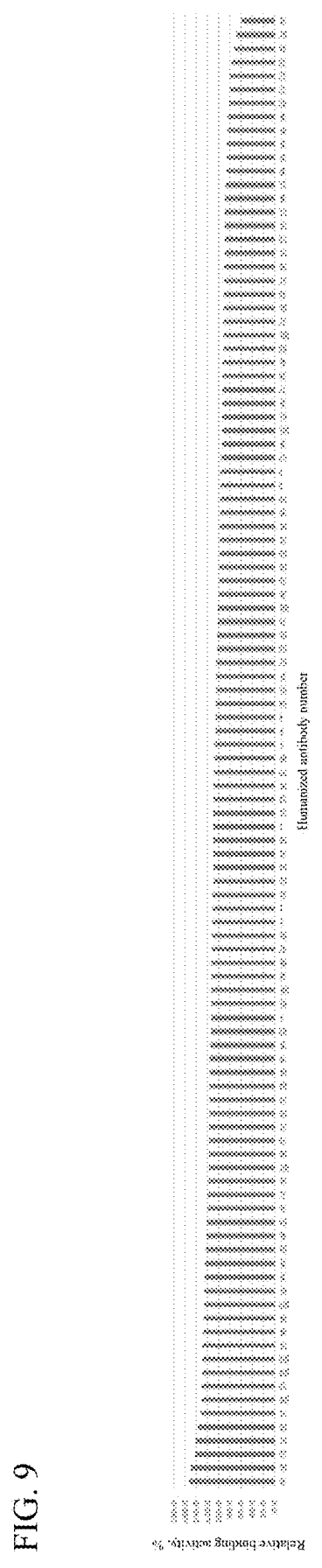

FIG. 9 shows the relative binding activity of the humanized anti-CTLA-4 antibodies in Table 4 relative to the control antibody.

As shown in FIG. 9, the humanized anti-CTLA-4 antibodies bound to huCTLA-4 well; they were comparable or superior to the control antibody in this respect.

8.2 ELISA Determination of Abilities of Humanized Anti-CTLA-4 Antibodies to Block Binding of huCTLA-4 to CD80

Figure 10:
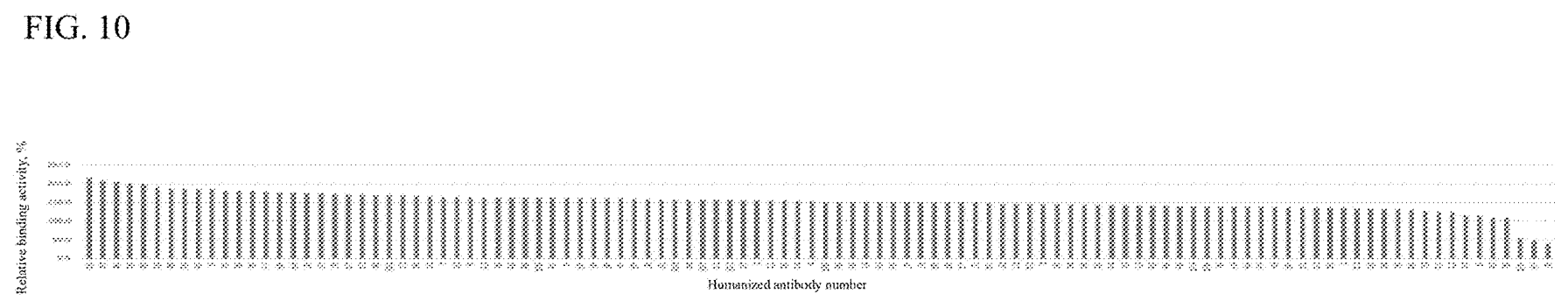

HX1 hCTLA4-his was diluted with PBS (Hyclone) to 1.0 g/mL, and the dilution was added to a microplate at 100 µL/well. The plate was let stand in an incubator at 37° C. and incubated for 90 min and then washed, and 2% BSA was added to the plate at 200 µL/well. The plate was incubated in an incubator at 37° C. for 90 min and then washed. MX2 hCD80 Fc was diluted with 2% BSA to 5.0 µg/mL, and the dilution was used to dilute antibodies. The humanized anti-CTLA-4 antibodies in Table 4 and the control antibody ipilimumab were diluted to 100 µg/mL. The dilution performed each time was not higher than 10-fold. Then, the humanized antibodies and the control antibody were serially diluted 2.5-fold on a sample dilution plate. All the humanized antibody solutions and the control antibody solution were added to a microplate at 100 µL/well. The plate was incubated in an incubator at 37° C. for 90 min and then washed. An HRP-conjugated goat anti-mouse antibody IgG (Fc specific) was diluted 5000-fold with 2% BSA, and the dilution was added to the microplate at 100 µL/well. The plate was incubated in an incubator at 37° C. for 60 min and then washed. The color development solution TMB was added at 100 µL/well, during which bubbles were avoided. Color development was allowed at 37° C. for 15 min in the dark and then terminated by adding 2 M hydrochloric acid solution at 100 µL/well, during which bubbles were avoided. Reading (wavelength: 450/620 nm) was done within 10 min using a microplate reader. FIG. 10 shows the relative inhibitory activity of the humanized anti-CTLA-4 antibodies relative to the control antibody.

As shown in FIG. 10, the humanized anti-CTLA-4 antibodies had good abilities to block the binding of huCTLA-4 to CD80; they were comparable or superior to the control antibody in this respect.

8.3 Luciferase Assays for Determining Biological Antagonistic Activity of Humanized Anti-CTLA-4 Antibodies Against huCTLA-4

Humanized anti-CTLA-4 antibodies huJS007-46, 47, 48, 49, 55, 56, 73, 79, 82, 88, 100 and 106 were selected for biological activity analysis based on the binding activity, binding-blocking activity and the degree of humanization described above.

HuCTLA-4-expressing Jurkat cells were plated at $6 \times 10^4$ cells/well, and $3 \times 10^4$ Raji PC cells and different concentrations of the above 12 humanized anti-CTLA-4 antibodies or the control antibody (ipilimumab) were added to each well. After 6 h of incubation, the T cell activation activity was determined through luciferase assays.

Figure 11:
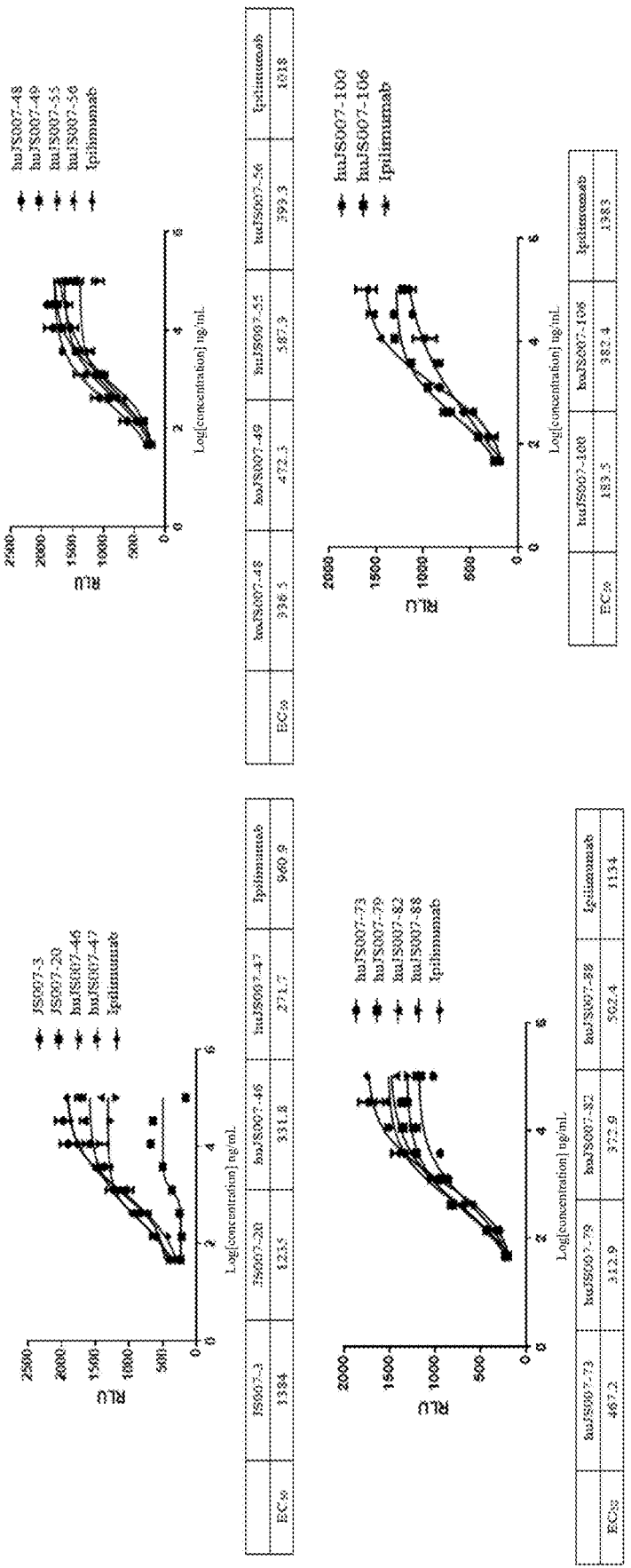
FIG. 11: Luciferase assays for determining the biological activity of humanized anti-CTLA-4 antibodies.

As shown in FIG. 11, the 12 humanized anti-CTLA-4 antibodies all had very high biological activity and were significantly superior in $EC_{50}$ to the control antibody ipilimumab.

Example 9. ADCC Activity of Humanized Anti-CTLA-4 Antibodies

293T-CTLA4 cells were labeled with CFSE. Peripheral blood mononuclear cells (PBMC2144896) and different concentrations of the above 12 humanized anti-CTLA-4 antibodies or the control antibody (ipilimumab) were added in a ratio of target cells to effector cells (target:effector) of 1:25. The cells were incubated overnight. The cells were stained with propidium iodide (PI) and analyzed using a flow cytometer. ADCC killing (%) was expressed as the percentage of dead target cells (PI and CFSE positive) to total target cells (CFSE positive).

Figure 12:
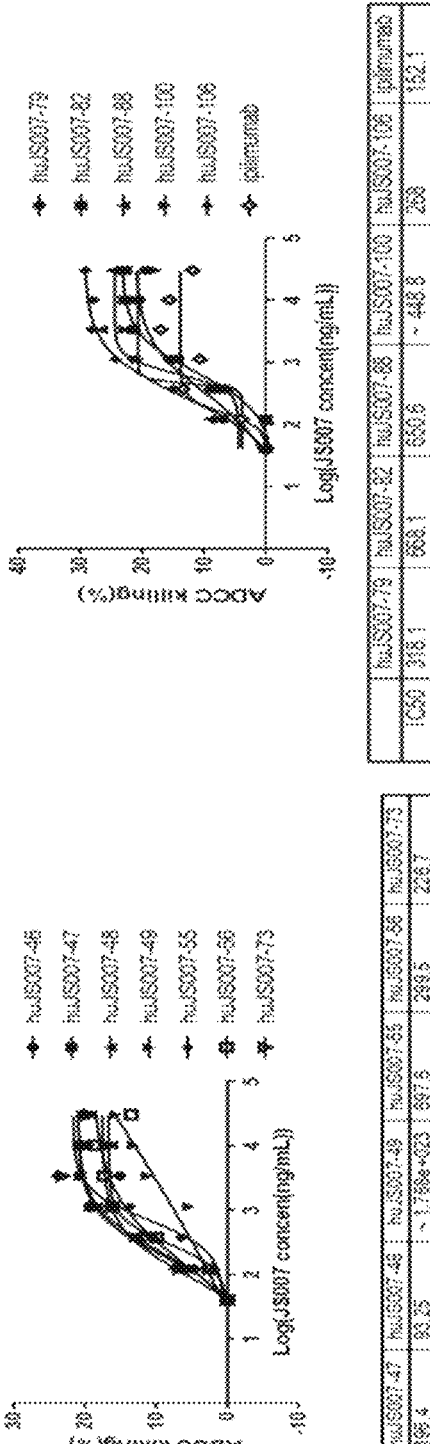
FIG. 12: the ADCC activity of humanized anti-CTLA-4 antibodies.

As shown in FIG. 12 (the two panels are shown for convenience only), the 12 humanized anti-CTLA-4 antibodies all had ADCC activity; the humanized anti-CTLA-4 antibodies 46, 47, 48, 73, 79 and 106, particularly 46 and 48, were comparable or superior in ADCC activity to the control antibody.

Example 10. CDC Activity of Humanized Anti-CTLA-4 Antibodies

Figure 13:
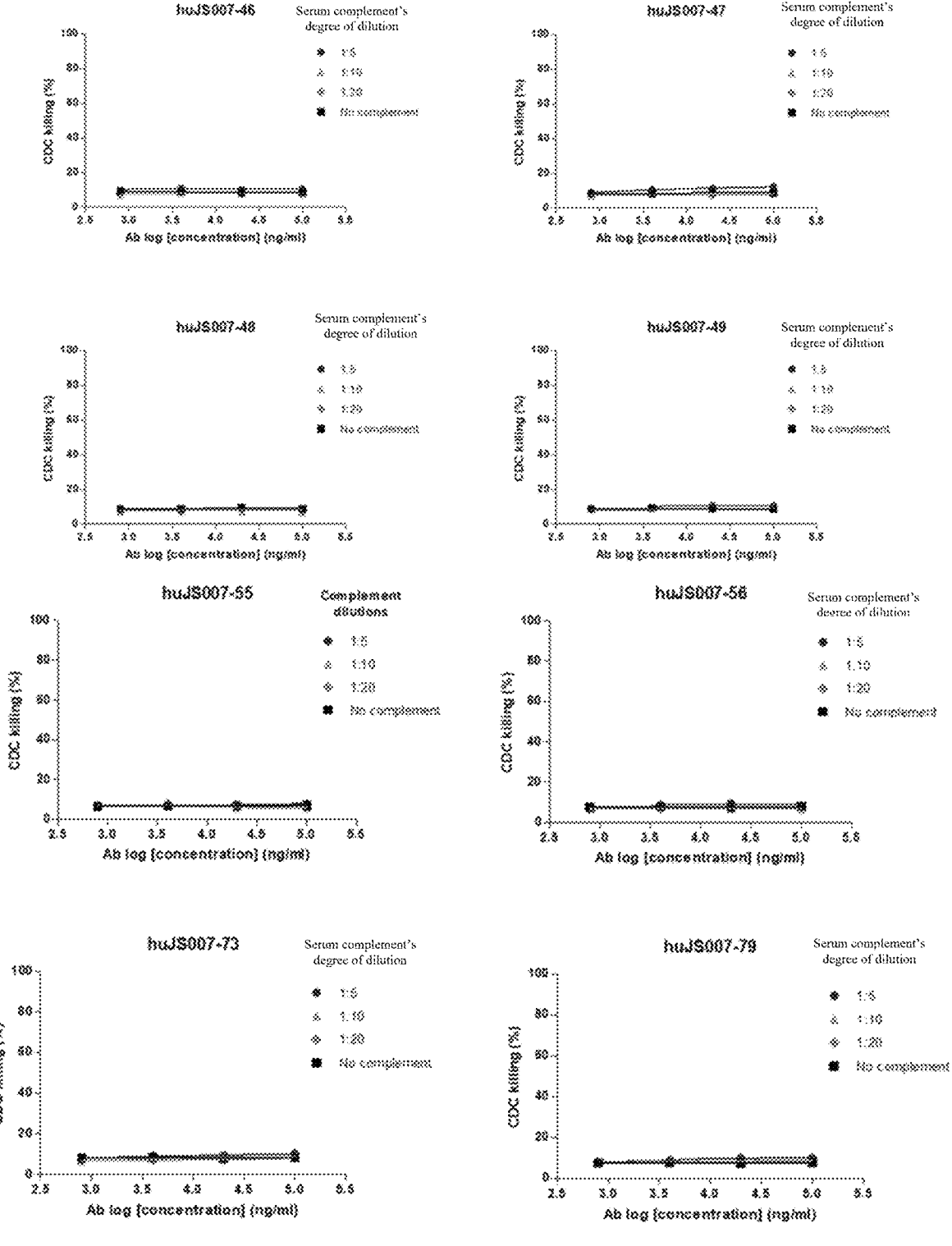
FIG. 13: the CDC activity of humanized anti-CTLA-4 antibodies.
Figure 13:
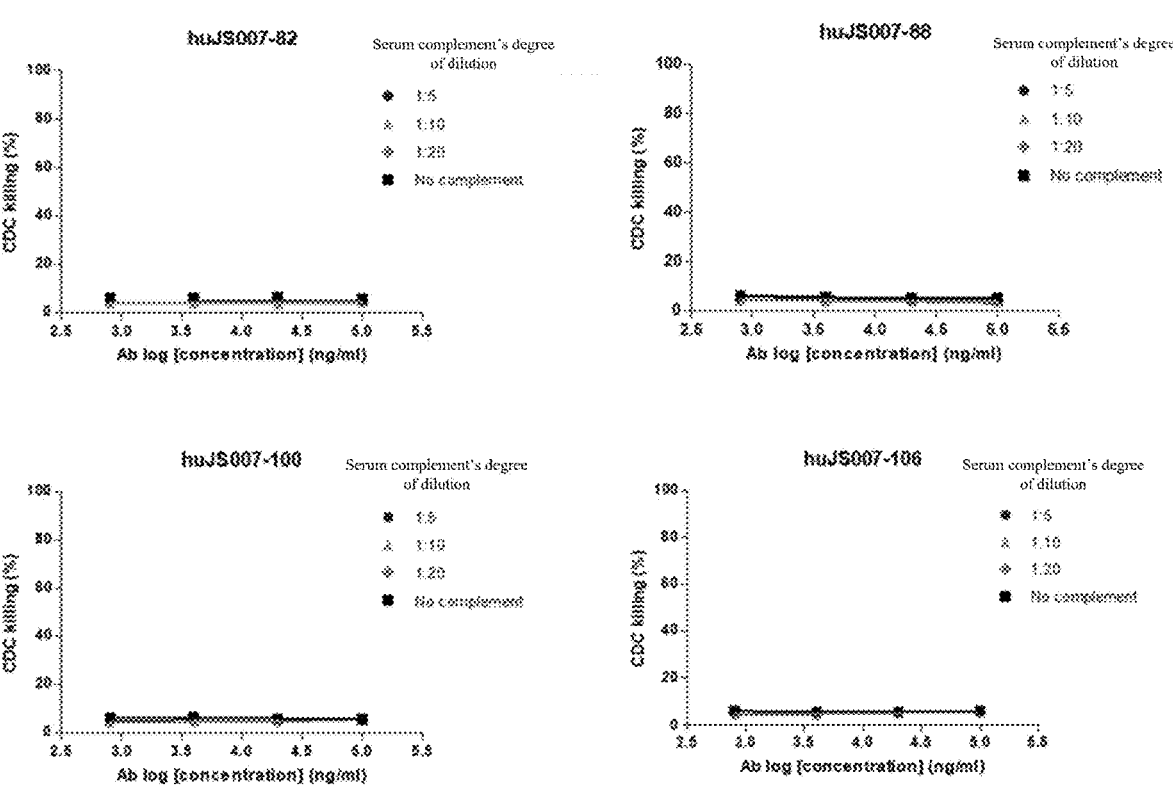
Figure 13:
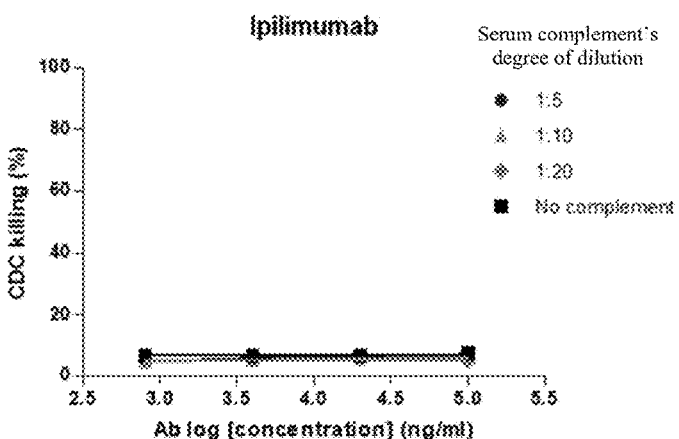

293T-CTLA4 cells were activated with different concentrations (0.8-100 µg/mL) of the 12 humanized anti-CTLA-4 antibodies or the control antibody (ipilimumab) at 37° C. for 15 min. Human serum complement of different dilution gradients (1:5, 1:10 and 1:20) was added, and the cells were cultured for 1 h. After the culture was completed, the cells were stained with propidium iodide (PI) and analyzed using a BD FACSCalibur flow cytometer. CDC killing (%) is expressed as the percentage of PI-positive target cells to total target cells. The results shown in FIG. 13 indicate that the above 12 humanized anti-CTLA-4 antibodies had no CDC activity or negligible CDC activity.

Humanized anti-CTLA-4 antibodies huJS007-47, huJS007-48, huJS007-79 and huJS007-106 were selected for further evaluation based on the binding activity, the ability to block binding, the biological activity, the ADCC activity and the CDC activity.

The CDR/variable region/light chain/heavy chain amino acid sequences of these 4 humanized anti-CTLA-4 antibodies are shown in Table 5.

TABLE 5

| Amino acid sequences of portions of 4 humanized anti-CTLA-4 antibodies (KABAT scheme) | | | |
|---|---|---|---|
| | huJS007-47 | huJS007-48 | huJS007-79 | huJS007-106 |
| HCDR1 | SEQ ID NO: 19 | SEQ ID NO: 19 | SEQ ID NO: 1 | SEQ ID NO: 19 |
| HCDR2 | SEQ ID NO: 39 | SEQ ID NO: 39 | SEQ ID NO: 37 | SEQ ID NO: 20 |
| HCDR3 | SEQ ID NO: 21 | SEQ ID NO: 21 | SEQ ID NO: 38 | SEQ ID NO: 21 |

TABLE 5-continued

Amino acid sequences of portions of 4 humanized
anti-CTLA-4 antibodies (KABAT scheme)

| | huJS007-47 | huJS007-48 | huJS007-79 | huJS007-106 |
|---|---|---|---|---|
| LCDR1 | SEQ ID NO: 40 | SEQ ID NO: 40 | SEQ ID NO: 40 | SEQ ID NO: 40 |
| LCDR2 | SEQ ID NO: 17 | SEQ ID NO: 17 | SEQ ID NO: 17 | SEQ ID NO: 17 |
| LCDR3 | SEQ ID NO: 18 | SEQ ID NO: 18 | SEQ ID NO: 18 | SEQ ID NO: 18 |
| VH | SEQ ID NO: 50 | SEQ ID NO: 50 | SEQ ID NO: 46 | SEQ ID NO: 53 |
| VL | SEQ ID NO: 55 | SEQ ID NO: 56 | SEQ ID NO: 60 | SEQ ID NO: 60 |
| HC | SEQ ID NO: 63 | SEQ ID NO: 65 | SEQ ID NO: 67 | SEQ ID NO: 69 |
| LC | SEQ ID NO: 64 | SEQ ID NO: 66 | SEQ ID NO: 68 | SEQ ID NO: 70 |

Example 11. Inhibition of Tumor Growth in Mice by Humanized Anti-CTLA-4 Antibodies Fifty female B-hCTLA4 humanized mice (Biocytogen) at 6-8 weeks of age were inoculated with MC38 WT cells subcutaneously on their right sides at a concentration of $1 \times 10^6 / 0.1$ mL. When the tumors had grown to about 138 mm$^3$, the mice were randomized into a total of 6 groups of 6 according to tumor volume, which were:

a G1 KLH IgG1 (0.3 mg/kg) negative control group,
a G2 ipilimumab (0.3 mg/kg) positive control group,
a G3 huJS007-47 (0.3 mg/kg) treatment group,
a G4 huJS007-48 (0.3 mg/kg) treatment group,
a G5 huJS007-79 (0.3 mg/kg) treatment group, and
a G6 huJS007-106 (0.3 mg/kg) treatment group.

The route of administration for all the groups was intraperitoneal injection. The administration dose was 0.3 mg/kg, and the administration concentration was 0.03 mg/mL. Administration was performed twice a week and continuously performed 5 times, and the experiment ended 3 days after the last administration. Tumor volume and body weight of mice were measured and recorded twice a week. At the end of the experiment, mice were euthanized and the relative tumor inhibition TGI %=(1−(Ti−T0)/(Vi−V0))×100% was calculated. Ti represents the mean tumor volumes of the treatment groups and the positive control group on day i of administration; TO represents the mean tumor volumes of the treatment groups and the positive control group on day 0 of administration; Vi represents the mean tumor volume of the negative control group on day i of administration; V0 represents the mean tumor volume of the negative control group on day 0 of administration.

Figure 14:
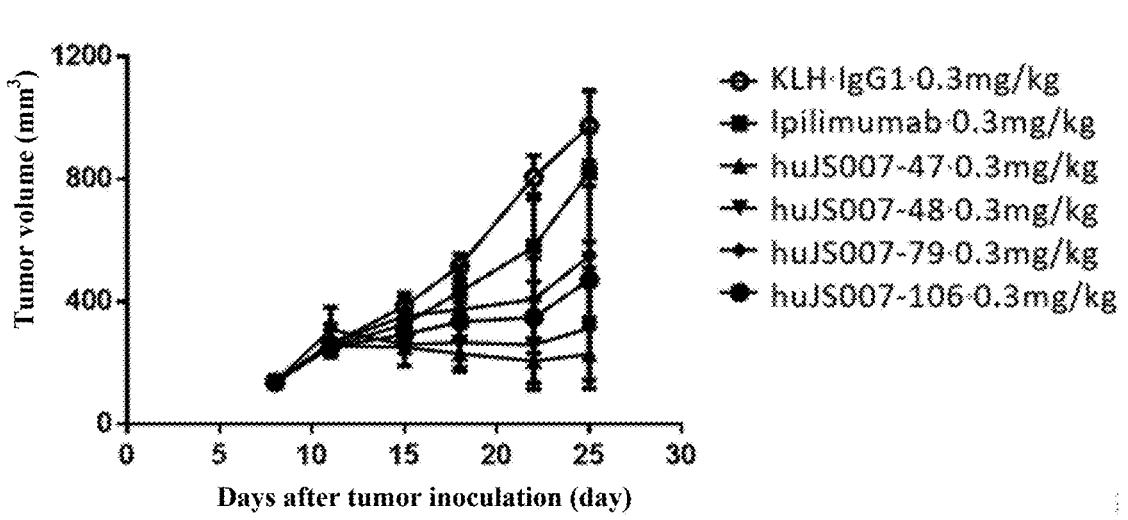
FIG. 14: the inhibition of tumor growth in mice by humanized anti-CTLA-4 antibodies.

As shown in FIG. 14, on day 25 after the mice were inoculated with tumor cells, the mean tumor volume of the KLH IgG1 negative control group was 975±115 mm$^3$, the mean tumor volume of the ipilimumab positive control group was 824±267 mm$^3$, and the relative tumor inhibition rate was 18.1% relative to KLH IgG1; the mean tumor volumes of the huJS007-47 treatment group, the huJS007-48 treatment group, the huJS007-79 treatment group and the huJS007-106 treatment group were 229±85 mm$^3$, 313±197 mm$^3$, 550±229 mm$^3$ and 472±125 mm$^3$, respectively, and the relative tumor inhibition rates were 89.2%, 79.1%, 50.9% and 60.1%, respectively, relative to KLH IgG1, which indicates that the above humanized anti-CTLA-4 antibodies were able to inhibit the growth of subcutaneously grafted MC38-WT cell tumors in B-hCTLA4 humanized mice, and were significantly superior to the control antibody ipilimumab in this respect.

Example 12: Identification of Epitopes Through Fortebio Binding Assays

The full-length antibodies, namely the humanized anti-CTLA-4 antibody huJS007-47 at 2.7 µg/mL and the control antibody ipilimumab at 2 µg/mL, were each captured first using a protein A probe (Fortebio). The probe was then immersed in a 55 nM human CTLA (huCTLA) antigen solution to allow the full-length antibodies to bind to the antigen. Finally, the probe was immersed in a 600 nM Fab solution, including the humanized Fab huJS00-47 and the control Fab (ipilimumab), to determine whether the antigen bound to the Fabs.

Figure 15:
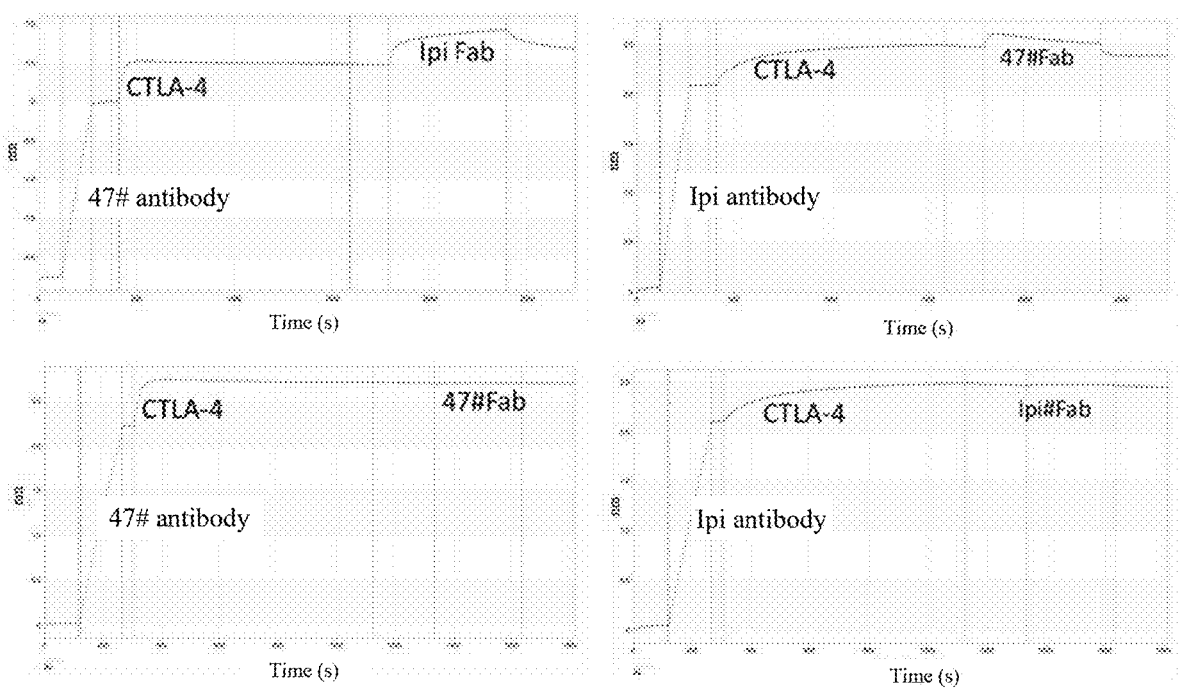
FIG. 15: the identification of epitopes through Fortebio binding assays.

As shown in FIG. 15, after the full-length antibody huJS007-47 bound to the antigen huCTLA-4, huCTLA-4 could continue to bind to the control Fab (ipilimumab), but according to the Fortebio binding assay results, huJS007-47 and ipilimumab bound to different epitopes of huCTLA-4.

Example 13: Identification of Epitopes by Hydrogen-Deuterium Exchange Mass Spectrometry Antigen-antibody two-dimensional polypeptide spectrum identification was carried out by hydrogen-deuterium exchange mass spectrometry: peptide fragments resulting from protein digestion were identified through a hydrogen-deuterium exchange mass spectrometry platform LEAP PAL3.0 using two-stage mass spectrometry (MS/MS) on a mass spectrometer (Orbitrap Fusion™ Tribrid™ Mass Spectrometer, Thermo Fisher). The MS/MS data file was submitted to the Proteome discover software for peptide fragment identification.

Preparation of hydrogen and deuterium exchange mass spectrometry samples: 5-10 micromoles of an antigen or an antibody or an antigen-antibody complex (1:1 molar ratio) (50 mM HEPES, pH 7.4, 150 mM NaCl, 2 mM DTT) were let stand at 4° C. for 1 h to form a stable complex. Five microliters of the above complex were diluted at 4° C. on an exchange buffer (50 mM HEPES, pH 7.4, 150 mM NaCl, 2 mM DTT) into 20 microliters of D$_2$O (deuterium), and various HDX time points (e.g., 0, 60, 300 and 900 seconds) were placed. After a period of hydrogen-deuterium exchange, the exchange was stopped by mixing with 25 µL of ice-cold 4 M guanidine hydrochloride and 1% trifluoroacetic acid. Immediately after the reaction was stopped, the sample tube was placed on dry ice until the sample was injected into the HDX LEAP PAL3.0 platform. After being injected into the fully automatic deuterium-hydrogen exchange platform, the sample was passed through a fixed pepsin column at 200 µL/min and the peptide fragments of digestion were captured on a C$_{18}$ capture column and desalted. The desalted peptide fragments were separated within 6 min using a 2.1 mm×5 cm C$_{18}$ column (1.9 µm Hypersil Gold, Thermo Fisher) with a linear gradient of 4-40% acetonitrile and 0.3% formic acid. The sample processing, protein digestion and peptide fragment isolation were all performed at 4° C. Mass spectral data of hydrogen-deuterium exchange were obtained using an Orbitrap mass spectrometer (Orbitrap Fusion™ Tribrid™ Mass Spectrometer, Thermo Fisher) with a measurement resolution of 65,000 (m/z 400). Each sample had three replicates at each time point.

Hydrogen-deuterium exchange mass spectrometry data analysis: the average m/z centroid value of the mass spectral peak intensity for each peptide fragment of enzymatic digestion was calculated using the HDX Workbench software and subsequently converted into percent deuterium incorporation. The key amino acid sequences involved in steric epitopes were calculated and the Delta % D difference was determined by calculating the difference between two samples (comparing changes in percent deuterium incorporation on the same peptide fragment). A Delta % D difference outside of −5 to 5% was considered significant. In addition, samples at each time point were subjected to student's t tests using HDX Workbench to determine the statistically significant (p<0.05) differences between them.

Figure 16:
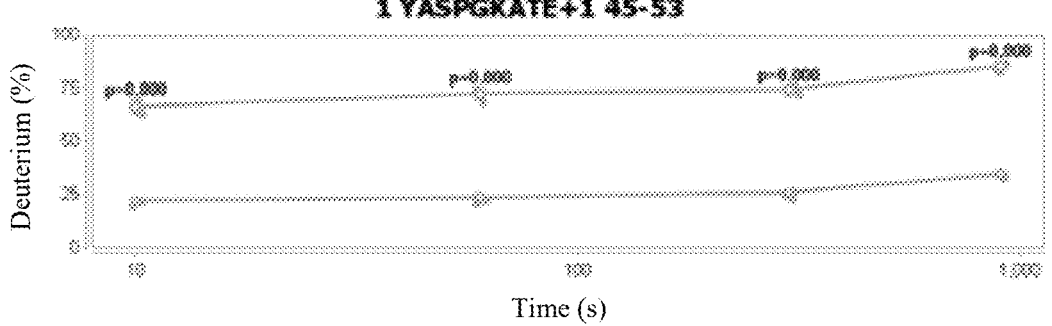
FIG. 16: the identification of epitopes by hydrogen-deuterium exchange mass spectrometry.

As shown in FIG. 16, the upper curve is indicative of the hydrogen-deuterium exchange rate of the peptide fragment (YASPGKATE, +1) which did not bind to huJS007-47, and the lower curve is indicative of the hydrogen-deuterium exchange rate of the peptide fragment which bound to huJS007-47 (significance decreased). According to the test results of the hydrogen-deuterium exchange mass spectrometry experiment, huJS007-47 and ipilimumab bound to different epitopes of huCTLA-4.

Example 14. ELISA Detection of Binding of Monoclonal Antibody HuJS007-47 to HuCTLA-4 Mutants According to the hydrogen-deuterium exchange mass spectrometry results, PCR amplified fragments obtained from mutation of "YASPGKATE" (SEQ ID NO: 72) in huCTLA-4 into P27A"YASAGKATE" (SEQ ID NO: 73), G28A"YASPAKATE" (SEQ ID NO: 74), K29A"YASPGAATE" (SEQ ID NO: 75) and T31A"YASPGKAAE" (SEQ ID NO: 76) were digested with enzymes EcoRI and NotI and then were cloned into the eukaryotic expression plasmid (HXT). 293 cells were transfected with the plasmid by PEI and cultured for 6 days, and then the culture supernatant was collected and purified to give a recombinant protein huCTLA-4 ECD (his-tag). Its amino acid sequence was a sequence of the 37$^{th}$ amino acid (A) to the 162$^{th}$ amino acid (F) of SEQ ID NO: 71.

The huCTLA-4 mutants used in the ELISA assays included non-mutated HXT huCTLA4 his, and mutated huCTLA4 N-his P27A, huCTLA4 N-his G28A, huCTLA4 N-his K29A and huCTLA4 N-his T31A. HuCTLA-4 his and its mutants were diluted with PBS (Hyclone) to 1.0 μg/mL, and a plate was coated with the dilution, incubated in an incubator at 37° C. for 90 min, washed and then blocked with 2% BSA. After the plate was washed, the monoclonal antibody huJS007-47 (serially diluted 2.5-fold with 2% BSA from 1000 ng/mL to 0.042 ng/ml) was added. The plate was incubated at 37° C. for 60 min and washed. A 1:5000 diluted HRP-conjugated goat anti-human antibody IgG (Fc specific) (Sigma, Catalog No. A0170) was used for detection. The plate was incubated at 37° C. for 60 min and then incubated with HRP substrate TMB (Sigma, Catalog No. T2885) at 37° C. for 15 min for color development. Finally, 2 M of hydrochloric acid was added to terminate the color development; during the addition, bubbles were avoided. Reading (wavelength: 450/620 nm) was done within 10 min using a microplate reader.

Figure 17:
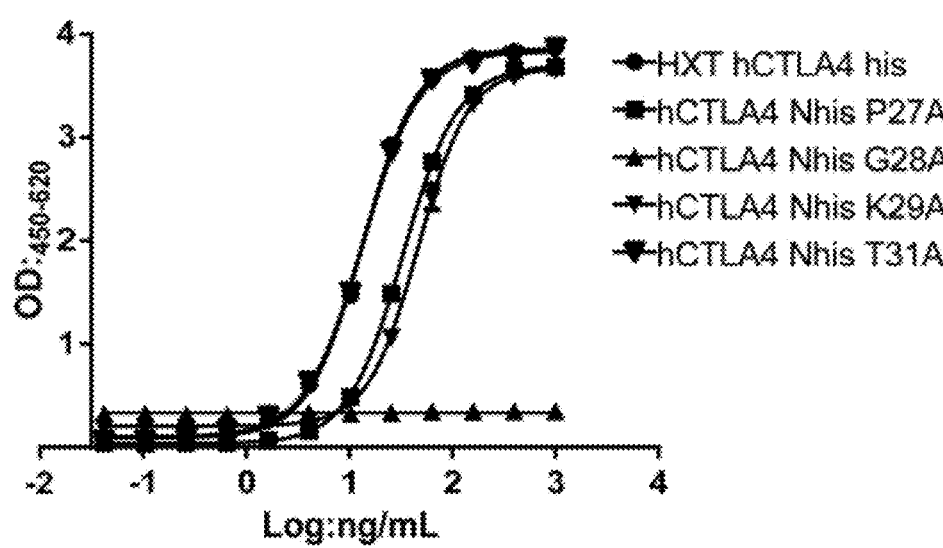
FIG. 17: ELISA detection of the binding of monoclonal antibody huJS007-47 to huCTLA-4 mutants.

As shown in FIG. 17, according to the ELISA results, when huJS007-47 bound to the antigen, the epitope on the surface of huCTLA-4 related to the binding to the antibody huJS007-47 was presumed to be at the amino acid P at position 27, the amino acid G at position 28 and the amino acid K at position 29. Mutating either the amino acid P at position 27 or the amino acid K at position 29 could greatly reduce the binding activity. Mutating only the amino acid G at position 28 could substantially completely inhibit the binding activity. These ELISA results were consistent with the hydrogen-deuterium exchange mass spectrometry results—huJS007-47 and ipilimumab bound to different epitopes of huCTLA-4.

Example 15. Inhibitory Effect of HuJS007-47 on Growth of Grafted MC38 Tumors in hCTLA4 Humanized Mice Female hCTLA4 humanized mice at 6-8 weeks of age (Biocytogen Jiangsu Co., Ltd.) were subcutaneously inoculated with $1\times10^6$ MC38 cells (0.1 mL/mouse (cell-containing medium RPMI1640 (Gibco))) on their right dorsal sides. When the mean tumor volume was about 119 mm$^3$, 40 animals were selected and randomized into 5 groups of 8 according to tumor volume, which were an anti-KLH hIgG1 negative control group, 1 mg/kg;
an ipilimumab positive control group, 1 mg/kg;
a huJS007-47 treatment group, 0.1 mg/kg;
a huJS007-47 treatment group. 0.3 mg/kg; and
a huJS007-47 treatment group, 1 mg/kg.

Administration was performed on the day of grouping, and the route of administration for all the groups was intraperitoneal injection. Administration was performed twice a week, and was continuously performed 6 times. The experiment ended 3 days after the last administration. Tumor volume and body weight of mice were measured and recorded twice a week. At the end of the experiment, mice were euthanized and tumor inhibition TGI % (TGI %=[1−(Ti−T0)/(Vi−V0)]×100%) was calculated. (Ti: the mean tumor volumes of the treatment groups on day i of administration, TO: the mean tumor volumes of the treatment groups on day 0 of administration; Vi: the mean tumor volume of the negative control group on day i of administration, V0: the mean tumor volume of the negative control group on day 0 of administration).

Figure 18:
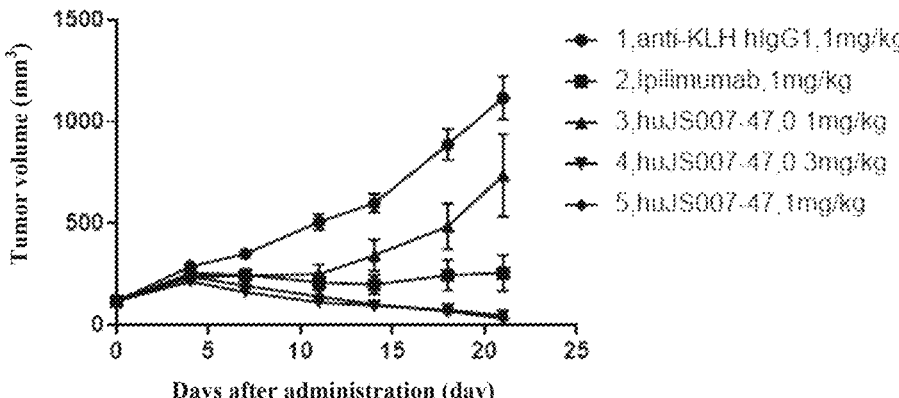
FIG. 18: the inhibitory effect of huJS007-47 on the growth of grafted MC38 tumors in hCTLA4 humanized mice.

As shown in FIG. 18, on day 21 after the administration began, the mean tumor volume of the anti-KLH hIgG1 negative control group (at a dose of 1 mg/kg) was 1116±106 mm$^3$; the mean tumor volume of the ipilimumab positive control group (at a dose of 1 mg/kg) was 255±88 mm$^3$, with TGI % of 86.36%; when huJS007-47 was administered at doses of 0.1, 0.3 and 1 mg/kg, the mean tumor volumes were 736±203 mm$^3$, 47±12 mm$^3$ and 33±15 mm$^3$, respectively, with TGI % of 38.11%, 107.22% and 108.63%. respectively. The above results indicate that when administered at doses of 0.1, 0.3 and 1 mg/kg, huJS007-47 significantly inhibited grafted MC38 tumors in hCTLA4 humanized mice from growing larger and exhibited a good dose-response relationship, and that when administered at the same dose (1 mg/kg), huJS007-47 was significantly superior to ipilimumab in inhibiting tumors.

Example 16. Inhibitory Effect of HuJS007-47 on Growth of Grafted H22 Tumors in hCTLA4 Humanized Mice Female hCTLA4 humanized mice at 6-8 weeks of age (Shanghai Model Organisms Co., Ltd.) were subcutaneously inoculated with $1\times10^6$ H22 cells (0.1 mL/mouse (cell-containing medium RPMI1640 (Gibco))) on their right-dorsal sides. When the mean tumor volume was about 119 mm$^3$, 35 animals were selected and randomized into 5 groups of 7 according to tumor volume, which were an anti-KLH hIgG1 negative control group, 0.3 mg/kg;
an ipilimumab positive control group, 0.1 mg/kg;
a huJS007-47 treatment group, 0.03 mg/kg;
a huJS007-47 treatment group. 0.1 mg/kg; and
a huJS007-47 treatment group, 0.3 mg/kg.

Administration was performed on the day of grouping, and the route of administration for all the groups was intraperitoneal injection. Administration was performed twice a week, and was continuously performed 6 times. The experiment ended 3 days after the last administration. Tumor volume and body weight of mice were measured and recorded twice a week. At the end of the experiment, mice were euthanized and tumor inhibition TGI % was calculated in the same way as in Example 15.

Figure 19:
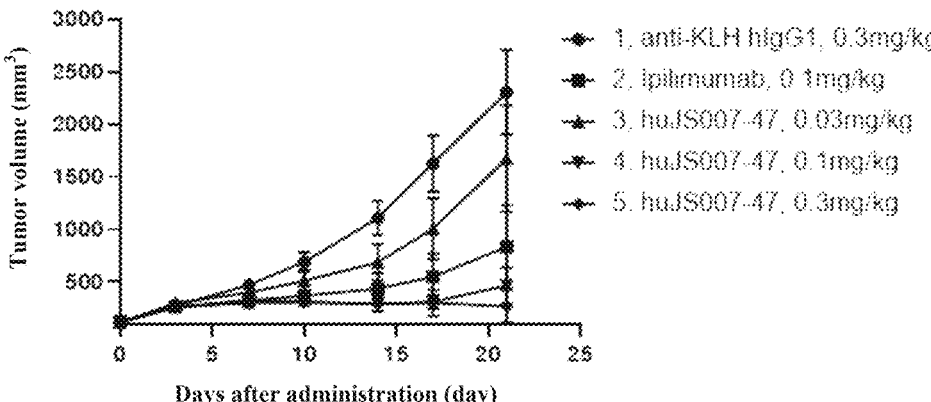
FIG. 19: the inhibitory effect of huJS007-47 on the growth of grafted H22 tumors in hCTLA4 humanized mice.

As shown in FIG. 19, on day 21 after the administration began, the mean tumor volume of the anti-KLH hIgG1 negative control group (at a dose of 0.3 mg/kg) was $2304\pm402$ mm$^3$; the mean tumor volume of the ipilimumab positive control group (at a dose of 0.1 mg/kg) was $837\pm397$ mm$^3$, with TGI % of 67.14%; when huJS007-47 was administered at doses of 0.03, 0.1 and 0.3 mg/kg, the mean tumor volumes were $1674\pm508$ mm$^3$, $466\pm171$ mm$^3$ and $271\pm155$ mm$^3$, respectively, with TGI % of 28.83%, 84.12% and 93.04%, respectively. The above results indicate that when administered at doses of 0.1 and 0.3 mg/kg, huJS007-47 significantly inhibited grafted H22 tumors in hCTLA4 humanized mice from growing larger and exhibited a good dose-response relationship, and that when administered at the same dose (0.1 mg/kg), huJS007-47 was significantly superior to ipilimumab in inhibiting tumors.

Example 17. Crystallization Method for CTLA4-JS007 scFv and Structure Analysis X-ray crystal diffraction was obtained by CTLA4-JS007 scFv complex protein preparation and crystal screening, and the structure of the complex was analyzed by molecular replacement method. Further, the molecular basis of CTLA4-JS007 scFv interaction was analyzed, so as to assess the molecular mechanism of the JS007 antibody (i.e., huJS007-47) binding to CTLA-4 and the mechanism of the antibody blocking CTLA-4/B7-1 interaction.

In the example, the JS007 scFv was huJS007-47 scFv, and the CTLA-4 protein was human CTLA-4 protein (SEQ ID NO: 71).

17.1 Experimental Method

17.1.1 Preparation of CTLA4-JS007 scFv Complex Protein and Crystal Screening The CTLA-4 protein (C35-P154) and JS007-scFv inclusion body protein were prepared using a prokaryotic expression system (*E. coli* BL21 strain), and the CTLA4 and JS007-scFv proteins were each obtained by in vitro inclusion body refolding. Both the proteins were then purified by gel filtration chromatography (GE, superdex 200 (10/300 GL)). The CTLA4 protein and JS007-scFv protein were placed on ice in a molar ratio of 1:1 and mixed and incubated for 30 min. Then the complex was further purified by gel filtration chromatography (GE, superdex 200 (10/300 GL)) to give a CTLA4-JS07 scFv complex protein. The CTLA4-JS007 scFv complex protein with a purity higher than 90% was subjected to crystal screening by using a crystal screening kit. 1 μL of protein solution was well mixed with 1 μL reservoir solution, at a concentration of 10 mg/mL, and the mixture was let stand at 16° C. for crystal growth. Finally, a CTLA4-JS007 scFv complex crystal was obtained by screening under MD1-13-20 conditions (0.1 M Tris pH: 8.5 30% w/v PEG 4000) in the Molecular Dimension company.

17.1.2 Structural Analysis of CTLA4-JS007 scFv Complex

The crystal diffraction data of the CTLA-4-JS007scFv complex protein were collected at BL17U Macromolecular Crystallography Beamline, Shanghai Synchrotron Radiation Facility (SSRF). The wavelength of X-ray used was 0.979 Å. The position of the crystal holder was adjusted, exposing and preliminary indexing (index) were performed, and diffraction data were collected. The diffraction data were processed using the HKL2000 software. Then a model was created and fine-tuned using Coot and Phenix. The final model was evaluated using Molprobity. The analyzed three-dimensional structure and electron density diagram of the protein were analyzed and displayed using the PyMOL software.

17.2 Structural Analysis

Figures 20A, 20B:
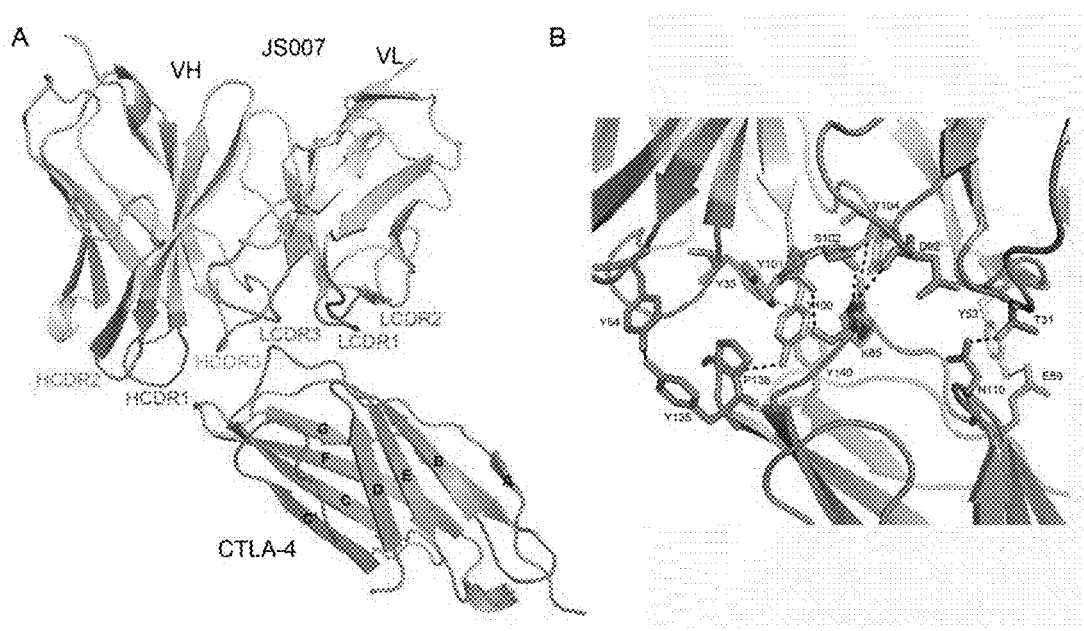
FIG. 20A is a diagram showing the overall structure of a complex of the heavy chain variable region (VH) and light chain variable region (VL) of JS007 antibody and CTLA-4, where the three heavy chain complementary determinants (HCDR1-3) and the three light chain complementary determinants (LCDR1-3) of JS007 are shown in different colors.
FIG. 20B shows a network of hydrogen bonding interactions between amino acids of JS007 and CTLA-4, where the amino acids involved in the hydrogen bonding interactions are shown as stick structures; the CDRs are shown in the same colors as in FIG. 20A, and the amino acids are shown in the same shades of colors as in corresponding regions.

17.2.1 Molecular Basis for Overall Structure and Interaction of JS007-CTLA-4 Complex A structural analysis of the complex of JS007 and CTLA-4 revealed that all the 6 CDRs of the JS007 antibody were involved in the interaction with CTLA-4 (FIG. 20A); the heavy chain contributed more interaction with CTLA-4 than the light chain (Table 6); the Y33 of the heavy chain CDR1, the Y54 of the heavy chain CDR2 and the Y100, Y101, S102 and Y104 of the heavy chain CDR3 formed extensive hydrogen bonding interactions with the BC loop (K65 and P63) and FG loop (Y135, P136 and Y140) of CTLA-4, while the T31 of the light chain CDR1, the Y53 of the light chain CDR2 and the D92 of the light chain CDR3 formed extensive hydrogen bonding interactions with the BC loop (E59 and K65) and N110 of CTLA-4 (FIG. 20B).

TABLE 6

| Interactions between the JS007 antibody's light/heavy chain and CTLA-4 | | |
| --- | --- | --- |
| | CTLA-4 | Number of interactions |
| Heavy chain | | |
| Y27 | K36, P138 | 2, 2 |
| S31 | P137 | 1 |
| G32 | P137, P138 | 7, 8 |
| Y33 | K36, P137, P138, Y140 | 7, 3, 9, 11 (1) |
| Y34 | P136 | 6 |
| Y54 | Y135, P137 | 6 (1), 8 |
| D55 | Y135 | 1 |
| Y100 | P63, G64, K65, A66, L133, Y135, P136, P137, P138, Y140 | 8, 12, 5, 6, 2, 10 (1), 2, 2, 3 |
| Y101 | G64, K65, P136 | 2, 11 (1), 3 |
| S102 | G64, K65 | 4, 8 (1) |
| G103 | P63, G64 | 4, 3 |
| Y104 | P63 | 12 (1) |
| Light chain | | |
| T31 | N110 | 13 (1) |
| Y32 | K65, G64, G109, N110 | 3, 1, 7, 7 |
| Y49 | H39, A61, S62 | 1, 8, 3 |
| S50 | E59, A61, S62, N110 | 1, 2, 1,4 |
| S52 | E59 | 1 |
| Y53 | H39, A41, E59, A61 | 1, 1, 13 (1), 10 |
| Y91 | S62, G64, K65 | 1, 2, 1 |
| D92 | K65 | 8 (1) |

Note:
the numerals not bracketed in the column "number of interactions" represent the number of Van der Waals interactions within a distance of 4.5 angstroms, and the numerals bracketed represent the number of hydrogen bonding interactions within a distance of 3.5 angstroms.

17.2.2 Structural Basis for JS007 Blocking Interaction Between CTLA-4 and B7-1

Blocking the interaction between CTLA-4 and its ligand B7-1 (i.e., CD80) or B7-2 (i.e., CD86) is one of the molecular mechanisms through which the JS007 antibody performs immune activation. By comparing the structure of the CTLA-4-JS007 complex with that of the CTLA-4-B7-1 complex (PDB: 1I8L), the mechanism of JS007 blocking the interaction between CTLA-4 and B7-1 was further analyzed.

Figures 21A, 21B:
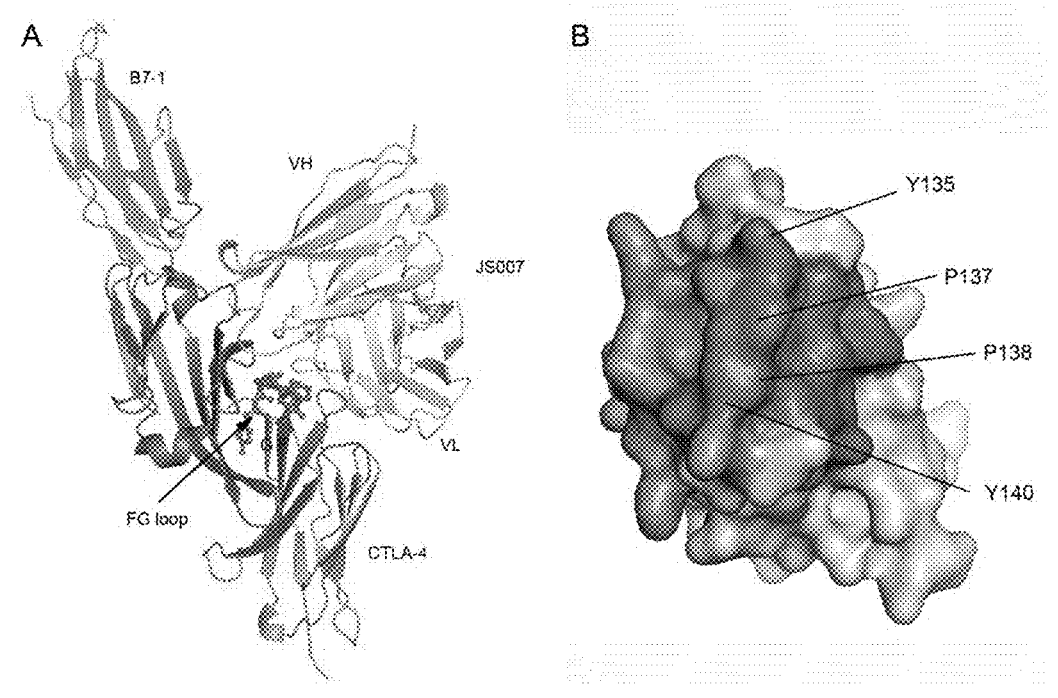
FIG. 21A is a diagram showing superimposed structures of complexes CTLA-4-JS007 and CTLA-4-B7-1 (PDB: 1I8L) with CTLA-4 as a fixed reference, where CTLA-4 is shown as the molecular structure of the CTLA-4 of CTLA-4-JS007; the FG loop of CTLA-4 mediates the major competitive binding, shown as the molecular structure diagram at the top left of FIG. 21A.
FIG. 21B is a diagram showing a surface representation of the binding to a JS007 or B7-1 molecule in CTLA-4, where the amino acids that only bind to the JS007 antibody are shown in dark colors at the top left of FIG. 21B, the amino acids that only bind to B7-1 are shown in dark colors at the top right of FIG. 21B, and the amino acids involved in interactions with both JS007 and B7-1 are shown in dark colors in the middle of FIG. 21B.

The structure of the CTLA-4-JS007 complex was superimposed on the structure of the CTLA-4-B7-1 complex (PDB: 1I8L) with CTLA-4 as a fixed reference, and the analysis results show that there was significant steric hindrance between the JS007's heavy chain and B7-1, while there were extensive interactions, including hydrogen bonding interactions and Van der Waals interactions, between the CTLA-4 molecule's FG loop and both JS007 and B7-1 (FIG. 21A). An analysis of the amino acids of the CTLA-4 molecule involved in the interactions with JS007 and B7-1 revealed that the Y135, P137, P138 and Y140 on the CTLA-4 molecule's FG loop were all involved in the binding to JS007 or B7-1, mediating the competitive binding of JS007 and B7-1 to CTLA-4 (FIG. 21B).

|  | SEQUENCE LISTING |
|---|---|
| SEQ ID NO: 1 | SGYYWN |
| SEQ ID NO: 2 | YIGYDGSNYYNPSLKN |
| SEQ ID NO: 3 | NYYSGYFDF |
| SEQ ID NO: 4 | KASQIVGSYVA |
| SEQ ID NO: 5 | STSYRHS |
| SEQ ID NO: 6 | QQHHLPLT |
| SEQ ID NO: 7 | DYYMS |
| SEQ ID NO: 8 | FIRNKANGFTAEYSASVKG |
| SEQ ID NO: 9 | DSLAYPHYYAMDY |
| SEQ ID NO: 10 | SASSSVSYMY |
| SEQ ID NO: 11 | LTSNLAS |
| SEQ ID NO: 12 | QQWSSNSFT |
| SEQ ID NO: 13 | DTYMH |
| SEQ ID NO: 14 | RIDPANGNTKSDPKFQG |
| SEQ ID NO: 15 | SMTTDPFTY |
| SEQ ID NO: 16 | KASQNVGTYVA |
| SEQ ID NO: 17 | STSYRYS |
| SEQ ID NO: 18 | HQYDTYPLT |
| SEQ ID NO: 19 | SGYYWN |
| SEQ ID NO: 20 | YIGYDGSNNYNPSLKN |
| SEQ ID NO: 21 | DYYSGYFDS |
| SEQ ID NO: 22 | DYYMK |
| SEQ ID NO: 23 | HINPNNGDTFYNQKFTG |
| SEQ ID NO: 24 | GGDGRGTWFAY |
| SEQ ID NO: 25 | RASESVDSYGISFMN |
| SEQ ID NO: 26 | AASNQGS |
| SEQ ID NO: 27 | QQSKEVPPT |

SEQ ID NO: 28
DVQLQESGQGLVKPSQSLSLTCSVTGYSITSGYYWNWIRQFPGNKLEWLGYIGYDGSNYYNPSL
KNRISITRDTSKNQFFLKLNSVTSEDTATYFCARNYYSGYFDFWGQGTT LTVSS

SEQ ID NO: 29
DIVMTQSQKFMSTSVGDRVSVTCKASQIVGSYVAWYQQKLGQSPKALIYSTSYRHSGVPDRFTG
SGSGTDFTLTISNVQSEDLAEYFCQQHHLPLTFGAGTKLEIK

-continued

SEQUENCE
LISTING

SEQ ID NO: 30
EVKLVESGGGLVQPGGSLRLSCATSGFTFTDYYMSWVRQPPGKALEWLGFIRNKANGFTAEYSA
SVKGRFTISRDNSQSILYLQMNTLRAEDSATYYCARDSLAYPHYYAMDYWGQGTSVTVSS

SEQ ID NO: 31
QIVLTQSPALMSASPGEKVTMTCSASSSVSYMWYQQKPRSSPKPWIYLTSNLASGVPVRFSGSG
SGTSYSLTISSMEAEDAATYYCQQWSSNSFTFGSGTKLEIK

SEQ ID NO: 32
EVQLQQSGAELVKSGASVKLSCTGSGFNIKDTYMHWVKQRPEEGLEWIGRIDPANGNTKSDPKF
QGKATITADTSSNTAYLQLSSLTSVDTAVYYCARSMTTDPFTYWGQGT LVTVSS

SEQ ID NO: 33
DIVMTQSQKFMSTSVGDSVSVTCKASQNVGTYVAWYQQKPGQSPKPLIYSTSYRYSGVPDRFTG
SGSGTDFTLTISNVQSEDLAEYFCHQYDTYPLTFGAGTKLELK

SEQ ID NO: 34
DVQLQESGPGLVKPSQSLSLTCSVTAYSITSGYYWNWIRQFPGNKLEWMGYIGYDGSNNYNPSL
KNRISITRDTSKNQFFLKLNSVTTEDTATYYCARDYYSGYFDSWGQGT TLTVSS

SEQ ID NO: 35
EVQLQQSGPELVKPGASVKMSCKASGYTFTDYYMKWMKQSHGKSLEWIGHINPNNGDTFYQKF
TGKATLTVDKSSSTASMHLNSLTSEDSAVYYCARGGDGRGTWFAY WGQGTLVTVSS

SEQ ID NO: 36
DIVLTQSPASLAEFLGQRATISCRASESVDSYGISFMNWFQQKPGQPPKLLIYAASNQGSGVPARF
SGSGSGTDFSLNIHPMEEDDTAMYFCQQSKEVPPTFGGGTKLEIK

SEQ ID NO: 37 YIGYDGSNYYNPSLKS

SEQ ID NO: 38 NYYSGYFDS

SEQ ID NO: 39 YIGYDGSNNYNPSLKS

SEQ ID NO: 40 RASQNVGTYVA

SEQ ID NO: 41 QASQNVGTYVA

SEQ ID NO: 42
QVQLQESGPGLVKPSQTLSLTCTVSGYSISSGYYWNWIRQHPGKGLEWIGYIGYDGSNYYNPSLK
SRVTISRDTSKNQFSLKLSSVTAADTAVYFCARNYYSGYFDFWGQGTT LTVSS

SEQ ID NO: 43
QVQLQESGPGLVKPSQTLSLTCTVSGYSITSGYYWNWIRQHPGKGLEWIGYIGYDGSNYYNPSLK
SRVTISRDTSKNQFSLKLSSVTAADTAVYFCARNYY SGYFDFWGQGTTLTVSS

SEQ ID NO: 44
QVQLQESGPGLVKPSETLSLTCTVTGYSITSGYYWNWIRQPAGKGLEWIGYIGYDGSNYYNPSLK
SRVTISRDTSKNQFSLKLSSVTAADTAVYFCARNYYSGYFDFWGQGTT LTVSS

SEQ ID NO: 45
QVQLQESGPGLVKPSQTLSLTCAVSGYSITSGYYWNWIRQHPGKGLEWIGYIGYDGSNYYNPSLK
SRVTISRDTSKNQFSLKLSSVTAADT AVYFCARNYYSGYFDFWGQGT TLTVSS

SEQ ID NO: 46
QVQLQESGPGLVKPSQTLSLTCAVSGYSISSGYYWNWIRQPPGKGLEWIGYIGYDGSNYYNPSLK
SRVTMSVDTSKNQFSLKLSSVTAVDTAVYYCARNYYSGYFDSWGQGT TVTVSS

SEQ ID NO: 47
QVQLQESGPGLVKPSQTLSLTCAVSGYSISSGYYWNWIRQFPGKGLEWMGYIGYDGSNYYNPSL
KNRVTMSVDTSKNQFSLKLSSVTAVDTAVYYCARNYYSGYFDSWGQG TTVTVSS

SEQ ID NO: 48
QVQLQESGPGLVKPSQTLSLTCAVSGYSISSGYYWNWIRQPPGKGLEWIGYIGYDGSNYYNPSLK
SRITISRDTSKNQFSLKLSSVTAVDTAVYYCARNYYSGYFDSWGQGTTVTVSS

SEQ ID NO: 49
QVQLQESGPGLVKPSQTLSLTCTVSGYSITSGYYWNWIRQHPGKGLEWIGYIGYDGSNNYNPSLK
SRVTISRDTSKNQFSLKLSSVTAADTAVYYCARDYYSGYFDSWGQGTTLTVSS

SEQUENCE
LISTING

SEQ ID NO: 50
QVQLQESGPGLVKPSQTLSLTCTVSAYSITSGYYWNWIRQHPGKGLEWIGYIGYDGSNNYNPSLK
SRVTISRDTSKNQFSLKLSSVTAADTAVYYCARDYYSGYFDSWGQGT TLTVSS

SEQ ID NO: 51
QVQLQESGPGLVKPSETLSLTCTVSGYSITSGYYWNWIRQPPGKGLEWIGYIGYDGSNNYNPSLK
SRVTISRDTSKNQFSLKLSSVTAADTAVYYCARDYYSGYFDSWGQGTT LTVSS

SEQ ID NO: 52
QVQLQESGPGLVKPSQTLSLTCAVSAYSITSGYYWNWIRQHPGKGLEWIGYIGYDGSNNYNPSLK
SRVTISRDTSKNQFSLKLSSVTAADTAVYYCARDYYSGYFDSWGQGT TLTVSS

SEQ ID NO: 53
QVQLQESGPGLVKPSQTLSLTCAVSGYSITSGYYWNWIRQPPGKGLEWIGYIGYDGSNNYNPSLK
NRVTMSVDTSKNQFSLKLSSVTAVDTAVYYCARDYYSGYFDSWGQG TTVTVSS

SEQ ID NO: 54
DIVMTQSPDSLAVSLGERATINCKASQNVGTYVAWYQQKPGQPPKPLIYSTSYRYSGVPDRFSGS
GSGTDFTLTISSLQAEDVAVYFCHQYDTYPLTFGAGTKLELK

SEQ ID NO: 55
DIQMTQSPSSLSASVGDRVTITCRASQNVGTYVAWYQQKPGKVPKPLIYSTSYRYSGVPSRFSGS
GSGTDFTLTISSLQPEDVATYFCHQYDTYPLTFGAGTKLELK

SEQ ID NO: 56
DIQMTQSPSSLSASVGDRVTITCRASQNVGTYVAWYQQKPGKAPKPLIYSTSYRYSGVPSRFSGS
GSGTDFTLTISSLQPEDFATYFCHQYDTYPLTFGAGTKLELK

SEQ ID NO: 57
DIQMTQSPSFLSASVGDRVTITCRASQNVGTYVAWYQQKPGKAPKPLIYSTSYRYSGVPSRFSGS
GSGTEFTLTISSLQPEDFATYFCHQYDTYPLTFGAGTKLELK

SEQ ID NO: 58
DIQMTQSPSSLSASVGDRVTITCQASQNVGTYVAWYQQKPGKAPKPLIYSTSYRYSGVPSRFSGS
GSGTDFTFTISSLQPEDIATYFCHQYDTYPLTFGAGTKLELK

SEQ ID NO: 59
DIVMTQSPDSLAVSLGERATINCKASQNVGTYVAWYQQKPGQPPKLLIYSTSYRYSGVPDRFSGS
GSGTDFTLTISSLQAEDVAVYYCHQYDTYPLTFGQGTKLEIK

SEQ ID NO: 60
EIVMTQSPATLSVSPGERATLSCRASQNVGTYVAWYQQKPGQAPRPLIYSTSYRYSGIPARFSGSG
SGTEFTLTISSLQSEDFAVYYCHQYDTYPLTFGQGTKLEIK

SEQ ID NO: 61
DIVMTQSPDSLAVSLGERATINCKASQNVGTYVAWYQQKPGQPPKPLIYSTSYRYSGVPDRFSGS
GSGTDFTLTISSLQAEDVAVYFCHQYDTYPLTFGQGTKLEIK

SEQ ID NO: 62
EIVMTQSPATLSVSPGERATLSCKASQNVGTYVAWYQQKPGQAPRPLIYSTSYRYSGIPARFSGSG
SGTEFTLTISSLQSEDFAVYFCHQYDTYPLTFGQGTKLEIK

SEQ ID NO: 63
QVQLQESGPGLVKPSQTLSLTCTVSAYSITSGYYWNWIRQHPGKGLEWIG**YIGYDGSNNYNPSL
KSRVTISRDTSKNQFSLKLSSVTAADTAVYYCARDYYSGYFDS**WGQGTTLTVSSASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSPGK

SEQ ID NO: 64
DIQMTQSPSSLSASVGDRVTITCRASQNVGTYVAWYQQKPGKVPKPLIYSTSYRYSGVPSRFSGS
GSGTDFTLTISSLQPEDVATYFCHQYDTYPLTFGAGTKLELKRTVAAPSVFIFPPSDEQLKSGTAS
VVCLLNNFYPREAKVQWKVDNALQSGNSQESVTEQDSKDSTYSLSSTLTLSKADYEKHKVYACE
VTHQGLSSPVTKSFNRGEC

SEQ ID NO: 65
QVQLQESGPGLVKPSQTLSLTCTVSAYSITSGYYWNWIRQHPGKGLEWIG**YIGYDGSNNYNPSL
KSRVTISRDTSKNQFSLKLSSVTAADTAVYYCARDYYSGYFDS**WGQGTTLTVSSASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSPGK

SEQUENCE
LISTING

SEQ ID NO: 66
DIQMTQSPSSLSASVGDRVTITCRASQNVGTYVAWYQQKPGKAPKPLIYSTSYRYSGVPSRFSGS
GSGTDFTLTISSLQPEDFATYFCHQYDTYPLTFGAGTKLELKRTVAAPS̲V̲F̲I̲F̲P̲P̲SDEQLKSGTAS
VVCLLNNFYPREAKVQWKVDNALQSGNSQESVTEQDSKDSTYSLSSTLTLSKADYEKHKVYACE
VTHQGLSSPVTKSFNRGEC

SEQ ID NO: 67
QVQLQESGPGLVKPSQTLSLTCAVSGYSISSGYYWNWIRQPPGKGLEWIGYIGYDGSNYYNPSL
KSRVTMSVDTSKNQFSLKLSSVTAVDTAVYYCARNYYSGYFDSWGQGTTVTVSSASTKGPSVFP
L̲APSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLSPGK

SEQ ID NO: 68
EIVMTQSPATLSVSPGERATLSCRASQNVGTYVAWYQQKPGQAPRPLIYSTSYRYSGIPARFSGS
GSGTEFTLTISSLQSEDFAVYYCHQYDTYPLTFGQGTKLEIKRTVAAPS̲V̲F̲I̲F̲P̲P̲SDEQLKSGTASV
VCLLNNFYPREAKVQWKVDNALQSGNSQESVTEQDSKDSTYSLSSTLTLSKADYEKHKVYACEV
THQGLSSPVTKSFNRGEC

SEQ ID NO: 69
QVQLQESGPGLVKPSQTLSLTCAVSGYSITSGYYWNWIRQPPGKGLEWIGYIGYDGSNNYNPSL
KNRVTMSVDTSKNQFSLKLSSVTAVDTAVYYCARDYYSGYFDSWGQGTTVTVSSASTKGPSVF
P̲LAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSLSPGK

SEQ ID NO: 70
EIVMTQSPATLSVSPGERATLSCRASQNVGTYVAWYQQKPGQAPRPLIYSTSYRYSGIPARFSGS
GSGTEFTLTISSLQSEDFAVYYCHQYDTYPLTFGQGTKLEIKRTVAAPS̲V̲F̲I̲F̲P̲P̲SDEQLKSGTASV
VCLLNNFYPREAKVQWKVDNALQSGNSQESVTEQDSKDSTYSLSSTLTLSKADYEKHKVYACEV
THQGLSSPVTKSFNRGEC

SEQ ID NO: 71
MACLGFQRHKAQLNLATRTWPCTLLFFLLFIPVFCKAMHVAQPAVVLASSRGIASFVCEYASPGK
ATEVRVTVLRQADSQVTEVCAATYMMGNELTFLDDSICTGTSSGNQVNLTIQGLRAMDTGLYIC
KVELMYPPPYYLGIGNGTQIYVIDPEPCPDSDFLLWILAAVSSGLFFYSFLLTAVSLSKMLKKRSPL
TTGVYVKMPPTEPECEKQFQPYFIPIN

SEQ ID NO: 72 YASPGKATE

SEQ ID NO: 73 YASAGKATE

SEQ ID NO: 74 YASPAKATE

SEQ ID NO: 75 YASPGAATE

SEQ ID NO: 76 YASPGKAAE

---

The invention claimed is:

1. An anti-CTLA-4 antibody or an antigen-binding fragment thereof, comprising:

(I) a heavy chain variable region, comprising HCDR1, HCDR2, and HCDR3 whose amino acid sequences are set forth in SEQ ID NO: 1, SEQ ID NO: 2 and SEQ ID NO: 3, respectively; and a light chain variable region, comprising LCDR1, LCDR2, and LCDR3 whose amino acid sequences are set forth in SEQ ID NO: 4, SEQ ID NO: 5 and SEQ ID NO: 6, respectively; or (II) a heavy chain variable region, comprising HCDR1, HCDR2, and HCDR3 whose amino acid sequences are set forth in SEQ ID NO: 7, SEQ ID NO: 8 and SEQ ID NO: 9, respectively; and a light chain variable region, comprising LCDR1, LCDR2, and LCDR3 whose amino acid sequences are set forth in SEQ ID NO: 10, SEQ ID NO: 11 and SEQ ID NO: 12, respectively; or (III) a heavy chain variable region, comprising HCDR1, HCDR2, and HCDR3 whose amino acid sequences are set forth in SEQ ID NO: 13, SEQ ID NO: 14 and SEQ ID NO: 15, respectively; and a light chain variable region, comprising LCDR1, LCDR2, and LCDR3 whose amino acid sequences are set forth in SEQ ID NO: 16, SEQ ID NO: 17 and SEQ ID NO: 18, respectively; or (IV) a heavy chain variable region, comprising HCDR1, HCDR2, and HCDR3 whose amino acid sequences are set forth in SEQ ID NO: 19, SEQ ID NO: 20 and SEQ ID NO: 21, respectively; and a light chain variable region, comprising LCDR1, LCDR2, and LCDR3 whose amino acid sequences are set forth in SEQ ID NO: 16, SEQ ID NO: 17 and SEQ ID NO: 18, respectively; or (V) a heavy chain variable region, comprising HCDR1, HCDR2, and HCDR3 whose amino acid sequences are set forth in SEQ ID NO: 22, SEQ ID NO: 23 and SEQ ID NO: 24, respectively; and a light chain variable region, comprising LCDR1, LCDR2, and LCDR3 whose amino acid sequences are set forth in SEQ ID NO: 25, SEQ ID NO: 26 and SEQ ID NO: 27, respectively; or (VI) a heavy chain variable region, comprising HCDR1, HCDR2, and HCDR3 whose amino acid sequences are set forth in SEQ ID NO: 1, SEQ ID NO: 2 and SEQ ID NO: 3, respectively; and a light chain variable region, comprising LCDR1, LCDR2, and LCDR3 whose amino acid sequences are set forth in SEQ ID NO: 16, SEQ ID NO: 17 and SEQ ID NO: 18, respectively; or (VII) a heavy chain variable region, comprising HCDR1, HCDR2, and HCDR3 whose amino acid sequences are set forth in SEQ ID NO: 19, SEQ ID NO: 39 and SEQ ID NO: 21, respectively; and a light chain variable region, comprising LCDR1, LCDR2, and LCDR3 whose amino acid sequences are set forth in SEQ ID NO: 40, SEQ ID NO: 17 and SEQ ID NO: 18, respectively; or (VIII) a heavy chain variable region, comprising HCDR1, HCDR2, and HCDR3 whose amino acid sequences are set forth in SEQ ID NO: 1, SEQ ID NO: 37 and SEQ ID NO: 38, respectively; and a light chain variable region, comprising LCDR1, LCDR2, and LCDR3 whose amino acid sequences are set forth in SEQ ID NO: 40, SEQ ID NO: 17 and SEQ ID NO: 18, respectively; or (IX) a heavy chain variable region, comprising HCDR1, HCDR2, and HCDR3 whose amino acid sequences are set forth in SEQ ID NO: 19, SEQ ID NO: 20 and SEQ ID NO: 21, respectively; and a light chain variable region, comprising LCDR1, LCDR2, and LCDR3 whose amino acid sequences are set forth in SEQ ID NO: 40, SEQ ID NO: 17 and SEQ ID NO: 18, respectively.

2. The antibody or the antigen-binding fragment thereof according to claim 1, comprising a heavy chain variable region and a light chain variable region, wherein the heavy chain variable region comprises the amino acid sequence set forth in any one of SEQ ID NOs: 28, 30, 32, 34, 35, 46, 48, 49, 50, 51, 52, and 53, or the amino acid sequence having at least 95%, 96%, 97%, 98%, or 99% sequence identity to the amino acid sequence set forth in any one of SEQ ID NOs: 28, 30, 32, 34, 35, 46, 48, 49, 50, 51, 52, and 53; and the light chain variable region comprises the amino acid sequence set forth in any one of SEQ ID NOs: 29, 31, 33, 36, 54, 55, 56, 57, 59, 60, 61, and 62, or the amino acid sequence having at least 95%, 96%, 97%, 98%, or 99% sequence identity to the amino acid sequence set forth in any one of SEQ ID NOs: 29, 31, 33, 36, 54, 55, 56, 57, 59, 60, 61, and 62.

3. The antibody or the antigen-binding fragment thereof according to claim 2, wherein the antibody comprises a heavy chain and a light chain; the heavy chain comprises the amino acid sequence set forth in any one of SEQ ID NOs: 63, 65, 67 and 69, or the amino acid sequence having at least 90%, 92%, 94%, 95%, 96%, 97%, 98% or 99% sequence identity to the amino acid sequence set forth in any one of SEQ ID NOs: 63, 65, 67 and 69; the light chain comprises the amino acid sequence set forth in any one of SEQ ID NOs: 64, 66, 68 and 70, or the amino acid sequence having at least 90%, 92%, 94%, 95%, 96%, 97%, 98% or 99% sequence identity to the amino acid sequence set forth in any one of SEQ ID NOs: 64, 66, 68 and 70.

4. The antibody or the antigen-binding fragment thereof according to claim 3, wherein the antibody comprises:

(I) a heavy chain whose amino acid sequence is set forth in SEQ ID NO: 63 and a light chain whose amino acid sequence is set forth in SEQ ID NO: 64; or (II) a heavy chain whose amino acid sequence is set forth in SEQ ID NO: 65 and a light chain whose amino acid sequence is set forth in SEQ ID NO: 66; or (III) a heavy chain whose amino acid sequence is set forth in SEQ ID NO: 67 and a light chain whose amino acid sequence is set forth in SEQ ID NO: 68; or (IV) a heavy chain whose amino acid sequence is set forth in SEQ ID NO: 69 and a light chain whose amino acid sequence is set forth in SEQ ID NO: 70.

5. The antibody or the antigen-binding fragment thereof according to claim 1, being a murine antibody, a chimeric antibody, or a humanized antibody, or an antigen-binding fragment thereof.

6. The antibody or the antigen-binding fragment thereof according to claim 2, being a murine antibody, a chimeric antibody, or a humanized antibody, or an antigen-binding fragment thereof.

7. The antibody or the antigen-binding fragment thereof according to claim 4, being a murine antibody, a chimeric antibody, or a humanized antibody, or an antigen-binding fragment thereof.

8. The antibody or the antigen-binding fragment thereof according to claim 1, wherein the antigen-binding fragment is a Fab, Fab', F(ab')2, Fv, or scFv.

9. The antibody or the antigen-binding fragment thereof according to claim 2, wherein the antigen-binding fragment is a Fab, Fab', F(ab')2, Fv, or scFv.

10. The antibody or the antigen-binding fragment thereof according to claim 1, wherein the anti-CTLA-4 antibody or the antigen-binding fragment thereof is of IgG1, IgG2, IgG3 or IgG4 subtype.

11. The antibody or the antigen-binding fragment thereof according to claim 2, wherein the anti-CTLA-4 antibody or the antigen-binding fragment thereof is of IgG1, IgG2, IgG3 or IgG4 subtype.

12. A method for treating cancer by eliminating, inhibiting, or reducing CTLA-4 activity, comprising administering to a subject in need of a therapeutically effective amount of the antibody antibodies or the antigen-binding fragment thereof according to claim 1, a polynucleotide encoding the antibody or the antigen-binding fragment thereof, an expression vector comprising the polynucleotide, a host cell comprising the expression vector, or a pharmaceutical composition comprising the antibody or the antigen-binding fragment thereof, the polynucleotide, the expression vector, or the host cell.

13. The method of claim 12, wherein the vector is a eukaryotic expression vector.

14. The method of claim 12, wherein the host cell is a eukaryotic cell; or the host cell is a mammalian cell.

15. The method of claim 12, wherein the cancer is selected from melanoma, renal cancer, prostate cancer, breast cancer, colon cancer, lung cancer, bone cancer, pancreatic cancer, skin cancer, head and neck cancer, uterine cancer, ovarian cancer, and rectal cancer.

16. A method for treating cancer by eliminating, inhibiting, or reducing CTLA-4 activity, comprising administering to a subject in need of a therapeutically effective amount of the antibody or the antigen-binding fragment thereof according to claim 2.

17. A method for treating cancer by eliminating, inhibiting, or reducing CTLA-4 activity, comprising administering to a subject in need of a therapeutically effective amount of the antibody or the antigen-binding fragment thereof according to claim 2.

\* \* \* \* \*

SEQUENCE LISTING

<160> NUMBER OF SEQ ID NOS: 76

<210> SEQ ID NO 1
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 1

Ser Gly Tyr Tyr Trp Asn
1                5

<210> SEQ ID NO 2
<211> LENGTH: 16
<212> TYPE: PRT

```
<213> ORGANISM: Artificial sequence
<220> FEATURE:
<223> OTHER INFORMATION: Synthetic polypeptide

<400> SEQUENCE: 2

Tyr Ile Gly Tyr Asp Gly Ser Asn Tyr Tyr Asn Pro Ser Leu Lys Asn
1               5                   10                  15

<210> SEQ ID NO 3
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 3

Asn Tyr Tyr Ser Gly Tyr Phe Asp Phe
1               5

<210> SEQ ID NO 4
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 4

Lys Ala Ser Gln Ile Val Gly Ser Tyr Val Ala
1               5                   10

<210> SEQ ID NO 5
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 5

Ser Thr Ser Tyr Arg His Ser
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 6

Gln Gln His His Leu Pro Leu Thr
1               5

<210> SEQ ID NO 7
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 7

Asp Tyr Tyr Met Ser
1               5

<210> SEQ ID NO 8
<211> LENGTH: 19
<212> TYPE: PRT
<213> ORGANISM: Artificial sequence
```

-continued

```
<220> FEATURE:
<223> OTHER INFORMATION: Synthetic polypeptide

<400> SEQUENCE: 8

Phe Ile Arg Asn Lys Ala Asn Gly Phe Thr Ala Glu Tyr Ser Ala Ser
1               5                   10                  15

Val Lys Gly

<210> SEQ ID NO 9
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 9

Asp Ser Leu Ala Tyr Pro His Tyr Tyr Ala Met Asp Tyr
1               5                   10

<210> SEQ ID NO 10
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 10

Ser Ala Ser Ser Ser Val Ser Tyr Met Tyr
1               5                   10

<210> SEQ ID NO 11
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 11

Leu Thr Ser Asn Leu Ala Ser
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 12

Gln Gln Trp Ser Ser Asn Ser Phe Thr
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 13

Asp Thr Tyr Met His
1               5

<210> SEQ ID NO 14
<211> LENGTH: 17
<212> TYPE: PRT
```

```
<213> ORGANISM: Artificial sequence
<220> FEATURE:
<223> OTHER INFORMATION: Synthetic polypeptide

<400> SEQUENCE: 14

Arg Ile Asp Pro Ala Asn Gly Asn Thr Lys Ser Asp Pro Lys Phe Gln
1               5                   10                  15

Gly

<210> SEQ ID NO 15
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 15

Ser Met Thr Thr Asp Pro Phe Thr Tyr
1               5

<210> SEQ ID NO 16
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 16

Lys Ala Ser Gln Asn Val Gly Thr Tyr Val Ala
1               5                   10

<210> SEQ ID NO 17
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 17

Ser Thr Ser Tyr Arg Tyr Ser
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 18

His Gln Tyr Asp Thr Tyr Pro Leu Thr
1               5

<210> SEQ ID NO 19
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 19

Ser Gly Tyr Tyr Trp Asn
1               5

<210> SEQ ID NO 20
<211> LENGTH: 16
```

```
<212> TYPE: PRT
<213> ORGANISM: Artificial sequence
<220> FEATURE:
<223> OTHER INFORMATION: Synthetic polypeptide

<400> SEQUENCE: 20

Tyr Ile Gly Tyr Asp Gly Ser Asn Asn Tyr Asn Pro Ser Leu Lys Asn
1               5                   10                  15

<210> SEQ ID NO 21
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 21

Asp Tyr Tyr Ser Gly Tyr Phe Asp Ser
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 22

Asp Tyr Tyr Met Lys
1               5

<210> SEQ ID NO 23
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 23

His Ile Asn Pro Asn Asn Gly Asp Thr Phe Tyr Asn Gln Lys Phe Thr
1               5                   10                  15

Gly

<210> SEQ ID NO 24
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 24

Gly Gly Asp Gly Arg Gly Thr Trp Phe Ala Tyr
1               5                   10

<210> SEQ ID NO 25
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 25

Arg Ala Ser Glu Ser Val Asp Ser Tyr Gly Ile Ser Phe Met Asn
1               5                   10                  15

<210> SEQ ID NO 26
```

-continued

```
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 26

Ala Ala Ser Asn Gln Gly Ser
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 27

Gln Gln Ser Lys Glu Val Pro Pro Thr
1               5

<210> SEQ ID NO 28
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 28

Asp Val Gln Leu Gln Glu Ser Gly Gln Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Leu Gly Tyr Ile Gly Tyr Asp Gly Ser Asn Tyr Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Ser Glu Asp Thr Ala Thr Tyr Phe Cys
                85                  90                  95

Ala Arg Asn Tyr Tyr Ser Gly Tyr Phe Asp Phe Trp Gly Gln Gly Thr
            100                 105                 110

Thr Leu Thr Val Ser Ser
        115

<210> SEQ ID NO 29
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 29

Asp Ile Val Met Thr Gln Ser Gln Lys Phe Met Ser Thr Ser Val Gly
1               5                   10                  15

Asp Arg Val Ser Val Thr Cys Lys Ala Ser Gln Ile Val Gly Ser Tyr
            20                  25                  30

Val Ala Trp Tyr Gln Gln Lys Leu Gly Gln Ser Pro Lys Ala Leu Ile
        35                  40                  45

Tyr Ser Thr Ser Tyr Arg His Ser Gly Val Pro Asp Arg Phe Thr Gly
    50                  55                  60
```

```
Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln His His Leu Pro Leu Thr
                85                  90                  95

Phe Gly Ala Gly Thr Lys Leu Glu Ile Lys
            100                 105
```

<210> SEQ ID NO 30
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 30

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Ala Leu Glu Trp Leu
            35                  40                  45

Gly Phe Ile Arg Asn Lys Ala Asn Gly Phe Thr Ala Glu Tyr Ser Ala
        50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Ser Leu Ala Tyr Pro His Tyr Tyr Ala Met Asp
                100                 105                 110

Tyr Trp Gly Gln Gly Thr Ser Val Thr Val Ser Ser
            115                 120
```

<210> SEQ ID NO 31
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 31

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Val Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Ser Phe Thr
                85                  90                  95

Phe Gly Ser Gly Thr Lys Leu Glu Ile Lys
            100                 105
```

<210> SEQ ID NO 32
<211> LENGTH: 118
<212> TYPE: PRT

-continued

```
<213> ORGANISM: Artificial sequence
<220> FEATURE:
<223> OTHER INFORMATION: Synthetic polypeptide

<400> SEQUENCE: 32

Glu Val Gln Leu Gln Gln Ser Gly Ala Glu Leu Val Lys Ser Gly Ala
1               5                   10                  15

Ser Val Lys Leu Ser Cys Thr Gly Ser Gly Phe Asn Ile Lys Asp Thr
            20                  25                  30

Tyr Met His Trp Val Lys Gln Arg Pro Glu Glu Gly Leu Glu Trp Ile
            35                  40                  45

Gly Arg Ile Asp Pro Ala Asn Gly Asn Thr Lys Ser Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Val Asp Thr Ala Val Tyr Tyr Cys
                85                  90                  95

Ala Arg Ser Met Thr Thr Asp Pro Phe Thr Tyr Trp Gly Gln Gly Thr
            100                 105                 110

Leu Val Thr Val Ser Ser
        115

<210> SEQ ID NO 33
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 33

Asp Ile Val Met Thr Gln Ser Gln Lys Phe Met Ser Thr Ser Val Gly
1               5                   10                  15

Asp Ser Val Ser Val Thr Cys Lys Ala Ser Gln Asn Val Gly Thr Tyr
            20                  25                  30

Val Ala Trp Tyr Gln Gln Lys Pro Gly Gln Ser Pro Lys Pro Leu Ile
            35                  40                  45

Tyr Ser Thr Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys His Gln Tyr Asp Thr Tyr Pro Leu
                85                  90                  95

Thr Phe Gly Ala Gly Thr Lys Leu Glu Leu Lys
            100                 105

<210> SEQ ID NO 34
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 34

Asp Val Gln Leu Gln Glu Ser Gly Pro Gly Leu Val Lys Pro Ser Gln
1               5                   10                  15

Ser Leu Ser Leu Thr Cys Ser Val Thr Ala Tyr Ser Ile Thr Ser Gly
            20                  25                  30

Tyr Tyr Trp Asn Trp Ile Arg Gln Phe Pro Gly Asn Lys Leu Glu Trp
            35                  40                  45
```

```
Met Gly Tyr Ile Gly Tyr Asp Gly Ser Asn Asn Tyr Asn Pro Ser Leu
    50              55                  60

Lys Asn Arg Ile Ser Ile Thr Arg Asp Thr Ser Lys Asn Gln Phe Phe
65              70                  75                  80

Leu Lys Leu Asn Ser Val Thr Thr Glu Asp Thr Ala Thr Tyr Tyr Cys
                85                  90                  95

Ala Arg Asp Tyr Tyr Ser Gly Tyr Phe Asp Ser Trp Gly Gln Gly Thr
            100                 105                 110

Thr Leu Thr Val Ser Ser
        115
```

<210> SEQ ID NO 35
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 35

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Met Lys Gln Ser His Gly Lys Ser Leu Glu Trp Ile
            35                  40                  45

Gly His Ile Asn Pro Asn Asn Gly Asp Thr Phe Tyr Asn Gln Lys Phe
        50                  55                  60

Thr Gly Lys Ala Thr Leu Thr Val Asp Lys Ser Ser Ser Thr Ala Ser
65              70                  75                  80

Met His Leu Asn Ser Leu Thr Ser Glu Asp Ser Ala Val Tyr Tyr Cys
                85                  90                  95

Ala Arg Gly Gly Asp Gly Arg Gly Thr Trp Phe Ala Tyr Trp Gly Gln
            100                 105                 110

Gly Thr Leu Val Thr Val Ser Ser
        115                 120
```

<210> SEQ ID NO 36
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 36

```
Asp Ile Val Leu Thr Gln Ser Pro Ala Ser Leu Ala Glu Phe Leu Gly
1               5                   10                  15

Gln Arg Ala Thr Ile Ser Cys Arg Ala Ser Glu Ser Val Asp Ser Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65              70                  75                  80

Pro Met Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys
```

-continued

```
                    100                 105                 110

<210> SEQ ID NO 37
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 37

Tyr Ile Gly Tyr Asp Gly Ser Asn Tyr Tyr Asn Pro Ser Leu Lys Ser
1               5                   10                  15

<210> SEQ ID NO 38
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 38

Asn Tyr Tyr Ser Gly Tyr Phe Asp Ser
1               5

<210> SEQ ID NO 39
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 39

Tyr Ile Gly Tyr Asp Gly Ser Asn Asn Tyr Asn Pro Ser Leu Lys Ser
1               5                   10                  15

<210> SEQ ID NO 40
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 40

Arg Ala Ser Gln Asn Val Gly Thr Tyr Val Ala
1               5                   10

<210> SEQ ID NO 41
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 41

Gln Ala Ser Gln Asn Val Gly Thr Tyr Val Ala
1               5                   10

<210> SEQ ID NO 42
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 42

Gln Val Gln Leu Gln Glu Ser Gly Pro Gly Leu Val Lys Pro Ser Gln
1               5                   10                  15
```

-continued

```
Thr Leu Ser Leu Thr Cys Thr Val Ser Gly Tyr Ser Ile Ser Ser Gly
            20                  25                  30

Tyr Tyr Trp Asn Trp Ile Arg Gln His Pro Gly Lys Gly Leu Glu Trp
            35                  40                  45

Ile Gly Tyr Ile Gly Tyr Asp Gly Ser Asn Tyr Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Asn Tyr Tyr Ser Gly Tyr Phe Asp Phe Trp Gly Gln Gly Thr
            100                 105                 110

Thr Leu Thr Val Ser Ser
        115
```

<210> SEQ ID NO 43
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 43

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln His Pro Gly Lys Gly Leu Glu Trp
            35                  40                  45

Ile Gly Tyr Ile Gly Tyr Asp Gly Ser Asn Tyr Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Asn Tyr Tyr Ser Gly Tyr Phe Asp Phe Trp Gly Gln Gly Thr
            100                 105                 110

Thr Leu Thr Val Ser Ser
        115
```

<210> SEQ ID NO 44
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 44

```
Gln Val Gln Leu Gln Glu Ser Gly Pro Gly Leu Val Lys Pro Ser Glu
1               5                   10                  15

Thr Leu Ser Leu Thr Cys Thr Val Thr Gly Tyr Ser Ile Thr Ser Gly
            20                  25                  30

Tyr Tyr Trp Asn Trp Ile Arg Gln Pro Ala Gly Lys Gly Leu Glu Trp
            35                  40                  45

Ile Gly Tyr Ile Gly Tyr Asp Gly Ser Asn Tyr Tyr Asn Pro Ser Leu
        50                  55                  60

Lys Ser Arg Val Thr Ile Ser Arg Asp Thr Ser Lys Asn Gln Phe Ser
```

```
65                  70                  75                  80
Leu Lys Leu Ser Ser Val Thr Ala Ala Asp Thr Ala Val Tyr Phe Cys
                85                  90                  95

Ala Arg Asn Tyr Tyr Ser Gly Tyr Phe Asp Phe Trp Gly Gln Gly Thr
                100                 105                 110

Thr Leu Thr Val Ser Ser
        115

<210> SEQ ID NO 45
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 45

Gln Val Gln Leu Gln Glu Ser Gly Pro Gly Leu Val Lys Pro Ser Gln
1                   5                   10                  15

Thr Leu Ser Leu Thr Cys Ala Val Ser Gly Tyr Ser Ile Thr Ser Gly
                20                  25                  30

Tyr Tyr Trp Asn Trp Ile Arg Gln His Pro Gly Lys Gly Leu Glu Trp
            35                  40                  45

Ile Gly Tyr Ile Gly Tyr Asp Gly Ser Asn Tyr Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Asn Tyr Tyr Ser Gly Tyr Phe Asp Phe Trp Gly Gln Gly Thr
                100                 105                 110

Thr Leu Thr Val Ser Ser
        115

<210> SEQ ID NO 46
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 46

Gln Val Gln Leu Gln Glu Ser Gly Pro Gly Leu Val Lys Pro Ser Gln
1                   5                   10                  15

Thr Leu Ser Leu Thr Cys Ala Val Ser Gly Tyr Ser Ile Ser Ser Gly
                20                  25                  30

Tyr Tyr Trp Asn Trp Ile Arg Gln Pro Pro Gly Lys Gly Leu Glu Trp
            35                  40                  45

Ile Gly Tyr Ile Gly Tyr Asp Gly Ser Asn Tyr Tyr Asn Pro Ser Leu
        50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Asn Tyr Tyr Ser Gly Tyr Phe Asp Ser Trp Gly Gln Gly Thr
                100                 105                 110

Thr Val Thr Val Ser Ser
        115
```

-continued

```
<210> SEQ ID NO 47
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 47

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
            20                  25                  30

Tyr Tyr Trp Asn Trp Ile Arg Gln Phe Pro Gly Lys Gly Leu Glu Trp
        35                  40                  45

Met Gly Tyr Ile Gly Tyr Asp Gly Ser Asn Tyr Tyr Asn Pro Ser Leu
    50                  55                  60

Lys Asn Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Asn Tyr Tyr Ser Gly Tyr Phe Asp Ser Trp Gly Gln Gly Thr
            100                 105                 110

Thr Val Thr Val Ser Ser
        115

<210> SEQ ID NO 48
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 48

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
            20                  25                  30

Tyr Tyr Trp Asn Trp Ile Arg Gln Pro Pro Gly Lys Gly Leu Glu Trp
        35                  40                  45

Ile Gly Tyr Ile Gly Tyr Asp Gly Ser Asn Tyr Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Asn Tyr Tyr Ser Gly Tyr Phe Asp Ser Trp Gly Gln Gly Thr
            100                 105                 110

Thr Val Thr Val Ser Ser
        115

<210> SEQ ID NO 49
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 49

Gln Val Gln Leu Gln Glu Ser Gly Pro Gly Leu Val Lys Pro Ser Gln
```

```
1               5                    10                   15

Thr Leu Ser Leu Thr Cys Thr Val Ser Gly Tyr Ser Ile Thr Ser Gly
            20                   25                   30

Tyr Tyr Trp Asn Trp Ile Arg Gln His Pro Gly Lys Gly Leu Glu Trp
            35                   40                   45

Ile Gly Tyr Ile Gly Tyr Asp Gly Ser Asn Asn Tyr Asn Pro Ser Leu
    50                   55                   60

Lys Ser Arg Val Thr Ile Ser Arg Asp Thr Ser Lys Asn Gln Phe Ser
65                   70                   75                   80

Leu Lys Leu Ser Ser Val Thr Ala Ala Asp Thr Ala Val Tyr Tyr Cys
                85                   90                   95

Ala Arg Asp Tyr Tyr Ser Gly Tyr Phe Asp Ser Trp Gly Gln Gly Thr
            100                  105                  110

Thr Leu Thr Val Ser Ser
        115
```

```
<210> SEQ ID NO 50
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 50

Gln Val Gln Leu Gln Glu Ser Gly Pro Gly Leu Val Lys Pro Ser Gln
1               5                    10                   15

Thr Leu Ser Leu Thr Cys Thr Val Ser Ala Tyr Ser Ile Thr Ser Gly
            20                   25                   30

Tyr Tyr Trp Asn Trp Ile Arg Gln His Pro Gly Lys Gly Leu Glu Trp
            35                   40                   45

Ile Gly Tyr Ile Gly Tyr Asp Gly Ser Asn Asn Tyr Asn Pro Ser Leu
    50                   55                   60

Lys Ser Arg Val Thr Ile Ser Arg Asp Thr Ser Lys Asn Gln Phe Ser
65                   70                   75                   80

Leu Lys Leu Ser Ser Val Thr Ala Ala Asp Thr Ala Val Tyr Tyr Cys
                85                   90                   95

Ala Arg Asp Tyr Tyr Ser Gly Tyr Phe Asp Ser Trp Gly Gln Gly Thr
            100                  105                  110

Thr Leu Thr Val Ser Ser
        115
```

```
<210> SEQ ID NO 51
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 51

Gln Val Gln Leu Gln Glu Ser Gly Pro Gly Leu Val Lys Pro Ser Glu
1               5                    10                   15

Thr Leu Ser Leu Thr Cys Thr Val Ser Gly Tyr Ser Ile Thr Ser Gly
            20                   25                   30

Tyr Tyr Trp Asn Trp Ile Arg Gln Pro Pro Gly Lys Gly Leu Glu Trp
            35                   40                   45

Ile Gly Tyr Ile Gly Tyr Asp Gly Ser Asn Asn Tyr Asn Pro Ser Leu
    50                   55                   60
```

```
Lys Ser Arg Val Thr Ile Ser Arg Asp Thr Ser Lys Asn Gln Phe Ser
65              70              75              80

Leu Lys Leu Ser Ser Val Thr Ala Ala Asp Thr Ala Val Tyr Tyr Cys
            85              90              95

Ala Arg Asp Tyr Tyr Ser Gly Tyr Phe Asp Ser Trp Gly Gln Gly Thr
            100             105             110

Thr Leu Thr Val Ser Ser
        115

<210> SEQ ID NO 52
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 52

Gln Val Gln Leu Gln Glu Ser Gly Pro Gly Leu Val Lys Pro Ser Gln
1               5               10              15

Thr Leu Ser Leu Thr Cys Ala Val Ser Ala Tyr Ser Ile Thr Ser Gly
            20              25              30

Tyr Tyr Trp Asn Trp Ile Arg Gln His Pro Gly Lys Gly Leu Glu Trp
        35              40              45

Ile Gly Tyr Ile Gly Tyr Asp Gly Ser Asn Asn Tyr Asn Pro Ser Leu
    50              55              60

Lys Ser Arg Val Thr Ile Ser Arg Asp Thr Ser Lys Asn Gln Phe Ser
65              70              75              80

Leu Lys Leu Ser Ser Val Thr Ala Ala Asp Thr Ala Val Tyr Tyr Cys
            85              90              95

Ala Arg Asp Tyr Tyr Ser Gly Tyr Phe Asp Ser Trp Gly Gln Gly Thr
            100             105             110

Thr Leu Thr Val Ser Ser
        115

<210> SEQ ID NO 53
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 53

Gln Val Gln Leu Gln Glu Ser Gly Pro Gly Leu Val Lys Pro Ser Gln
1               5               10              15

Thr Leu Ser Leu Thr Cys Ala Val Ser Gly Tyr Ser Ile Thr Ser Gly
            20              25              30

Tyr Tyr Trp Asn Trp Ile Arg Gln Pro Pro Gly Lys Gly Leu Glu Trp
        35              40              45

Ile Gly Tyr Ile Gly Tyr Asp Gly Ser Asn Asn Tyr Asn Pro Ser Leu
    50              55              60

Lys Asn Arg Val Thr Met Ser Val Asp Thr Ser Lys Asn Gln Phe Ser
65              70              75              80

Leu Lys Leu Ser Ser Val Thr Ala Val Asp Thr Ala Val Tyr Tyr Cys
            85              90              95

Ala Arg Asp Tyr Tyr Ser Gly Tyr Phe Asp Ser Trp Gly Gln Gly Thr
            100             105             110

Thr Val Thr Val Ser Ser
        115
```

```
<210> SEQ ID NO 54
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 54

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asn Val Gly Thr Tyr
                20                  25                  30

Val Ala Trp Tyr Gln Gln Lys Pro Gly Gln Pro Pro Lys Pro Leu Ile
            35                  40                  45

Tyr Ser Thr Ser Tyr Arg Tyr Ser Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys His Gln Tyr Asp Thr Tyr Pro Leu
                85                  90                  95

Thr Phe Gly Ala Gly Thr Lys Leu Glu Leu Lys
            100                 105

<210> SEQ ID NO 55
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Gly Thr Tyr
                20                  25                  30

Val Ala Trp Tyr Gln Gln Lys Pro Gly Lys Val Pro Lys Pro Leu Ile
            35                  40                  45

Tyr Ser Thr Ser Tyr Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys His Gln Tyr Asp Thr Tyr Pro Leu
                85                  90                  95

Thr Phe Gly Ala Gly Thr Lys Leu Glu Leu Lys
            100                 105

<210> SEQ ID NO 56
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Gly Thr Tyr
                20                  25                  30
```

```
Val Ala Trp Tyr Gln Gln Lys Pro Gly Lys Ala Pro Lys Pro Leu Ile
        35                  40                  45

Tyr Ser Thr Ser Tyr Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys His Gln Tyr Asp Thr Tyr Pro Leu
                85                  90                  95

Thr Phe Gly Ala Gly Thr Lys Leu Glu Leu Lys
            100                 105
```

```
<210> SEQ ID NO 57
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 57
```

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asn Val Gly Thr Tyr
            20                  25                  30

Val Ala Trp Tyr Gln Gln Lys Pro Gly Lys Ala Pro Lys Pro Leu Ile
        35                  40                  45

Tyr Ser Thr Ser Tyr Arg Tyr Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys His Gln Tyr Asp Thr Tyr Pro Leu
                85                  90                  95

Thr Phe Gly Ala Gly Thr Lys Leu Glu Leu Lys
            100                 105
```

```
<210> SEQ ID NO 58
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 58
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Gly Thr Tyr
            20                  25                  30

Val Ala Trp Tyr Gln Gln Lys Pro Gly Lys Ala Pro Lys Pro Leu Ile
        35                  40                  45

Tyr Ser Thr Ser Tyr Arg Tyr Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys His Gln Tyr Asp Thr Tyr Pro Leu
                85                  90                  95

Thr Phe Gly Ala Gly Thr Lys Leu Glu Leu Lys
            100                 105
```

```
<210> SEQ ID NO 59
```

```
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 59

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asn Val Gly Thr Tyr
            20                  25                  30

Val Ala Trp Tyr Gln Gln Lys Pro Gly Gln Pro Pro Lys Leu Leu Ile
        35                  40                  45

Tyr Ser Thr Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln Tyr Asp Thr Tyr Pro Leu
                85                  90                  95

Thr Phe Gly Gln Gly Thr Lys Leu Glu Ile Lys
            100                 105

<210> SEQ ID NO 60
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 60

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asn Val Gly Thr Tyr
            20                  25                  30

Val Ala Trp Tyr Gln Gln Lys Pro Gly Gln Ala Pro Arg Pro Leu Ile
        35                  40                  45

Tyr Ser Thr Ser Tyr Arg Tyr Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys His Gln Tyr Asp Thr Tyr Pro Leu
                85                  90                  95

Thr Phe Gly Gln Gly Thr Lys Leu Glu Ile Lys
            100                 105

<210> SEQ ID NO 61
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 61

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asn Val Gly Thr Tyr
            20                  25                  30

Val Ala Trp Tyr Gln Gln Lys Pro Gly Gln Pro Pro Lys Pro Leu Ile
        35                  40                  45
```

-continued

```
Tyr Ser Thr Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys His Gln Tyr Asp Thr Tyr Pro Leu
                85                  90                  95

Thr Phe Gly Gln Gly Thr Lys Leu Glu Ile Lys
                100                 105
```

<210> SEQ ID NO 62
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 62

```
Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Tyr
                20                  25                  30

Val Ala Trp Tyr Gln Gln Lys Pro Gly Gln Ala Pro Arg Pro Leu Ile
            35                  40                  45

Tyr Ser Thr Ser Tyr Arg Tyr Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys His Gln Tyr Asp Thr Tyr Pro Leu
                85                  90                  95

Thr Phe Gly Gln Gly Thr Lys Leu Glu Ile Lys
                100                 105
```

<210> SEQ ID NO 63
<211> LENGTH: 448
<212> TYPE: PRT
<213> ORGANISM: Artificial sequence
<220> FEATURE:
<223> OTHER INFORMATION: Synthetic polypeptide

<400> SEQUENCE: 63

```
Gln Val Gln Leu Gln Glu Ser Gly Pro Gly Leu Val Lys Pro Ser Gln
1               5                   10                  15

Thr Leu Ser Leu Thr Cys Thr Val Ser Ala Tyr Ser Ile Thr Ser Gly
                20                  25                  30

Tyr Tyr Trp Asn Trp Ile Arg Gln His Pro Gly Lys Gly Leu Glu Trp
            35                  40                  45

Ile Gly Tyr Ile Gly Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Tyr Ser Gly Tyr Phe Asp Ser Trp Gly Gln Gly Thr
                100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445
```

```
<210> SEQ ID NO 64
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Gly Thr Tyr
                20                  25                  30

Val Ala Trp Tyr Gln Gln Lys Pro Gly Lys Val Pro Lys Pro Leu Ile
            35                  40                  45

Tyr Ser Thr Ser Tyr Arg Tyr Ser Gly Val Pro Ser Arg Phe Ser Gly
        50                  55                  60
```

```
Ser Gly Ser Gly Thr Asp Phe Thr Leu Thr Ile Ser Ser Leu Gln Pro
65                  70                  75                  80

Glu Asp Val Ala Thr Tyr Phe Cys His Gln Tyr Asp Thr Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 65
<211> LENGTH: 448
<212> TYPE: PRT
<213> ORGANISM: Artificial sequence
<220> FEATURE:
<223> OTHER INFORMATION: Synthetic polypeptide

<400> SEQUENCE: 65

```
Gln Val Gln Leu Gln Glu Ser Gly Pro Gly Leu Val Lys Pro Ser Gln
1               5                   10                  15

Thr Leu Ser Leu Thr Cys Thr Val Ser Ala Tyr Ser Ile Thr Ser Gly
            20                  25                  30

Tyr Tyr Trp Asn Trp Ile Arg Gln His Pro Gly Lys Gly Leu Glu Trp
            35                  40                  45

Ile Gly Tyr Ile Gly Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Tyr Ser Gly Tyr Phe Asp Ser Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205
```

-continued

```
Asn Thr Lys Val Asp Lys Lys Val Glu Pro Lys Ser Cys Asp Lys Thr
    210             215                 220

His Thr Cys Pro Pro Cys Pro Ala Pro Glu Leu Leu Gly Gly Pro Ser
225             230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305             310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 66
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 66
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Gly Thr Tyr
            20                  25                  30

Val Ala Trp Tyr Gln Gln Lys Pro Gly Lys Ala Pro Lys Pro Leu Ile
        35                  40                  45

Tyr Ser Thr Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Phe Cys His Gln Tyr Asp Thr Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 448
<212> TYPE: PRT
<213> ORGANISM: Artificial sequence
<220> FEATURE:
<223> OTHER INFORMATION: Synthetic polypeptide

<400> SEQUENCE: 67

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Gly
            20                  25                  30

Tyr Tyr Trp Asn Trp Ile Arg Gln Pro Pro Gly Lys Gly Leu Glu Trp
            35                  40                  45

Ile Gly Tyr Ile Gly Tyr Asp Gly Ser Asn Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Asn Tyr Tyr Ser Gly Tyr Phe Asp Ser Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
        275             280             285

Lys Thr Lys Pro Arg Glu Glu Gln Tyr Asn Ser Thr Tyr Arg Val Val
    290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
            325             330             335

Ile Ser Lys Ala Lys Gly Gln Pro Arg Glu Pro Gln Val Tyr Thr Leu
            340             345             350

Pro Pro Ser Arg Asp Glu Leu Thr Lys Asn Gln Val Ser Leu Thr Cys
            355             360             365

Leu Val Lys Gly Phe Tyr Pro Ser Asp Ile Ala Val Glu Trp Glu Ser
    370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
            405             410             415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Lys
            435             440             445
```

```
<210> SEQ ID NO 68
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 68
```

```
Glu Ile Val Met Thr Gln Ser Pro Ala Thr Leu Ser Val Ser Pro Gly
1               5               10              15

Glu Arg Ala Thr Leu Ser Cys Arg Ala Ser Gln Asn Val Gly Thr Tyr
            20              25              30

Val Ala Trp Tyr Gln Gln Lys Pro Gly Gln Ala Pro Arg Pro Leu Ile
        35              40              45

Tyr Ser Thr Ser Tyr Arg Tyr Ser Gly Ile Pro Ala Arg Phe Ser Gly
    50              55              60

Ser Gly Ser Gly Thr Glu Phe Thr Leu Thr Ile Ser Ser Leu Gln Ser
65              70              75              80

Glu Asp Phe Ala Val Tyr Tyr Cys His Gln Tyr Asp Thr Tyr Pro Leu
            85              90              95

Thr Phe Gly Gln Gly Thr Lys Leu Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190
```

-continued

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 69
<211> LENGTH: 448
<212> TYPE: PRT
<213> ORGANISM: Artificial sequence
<220> FEATURE:
<223> OTHER INFORMATION: Synthetic polypeptide

<400> SEQUENCE: 69

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Thr Ser Gly
            20                  25                  30

Tyr Tyr Trp Asn Trp Ile Arg Gln Pro Pro Gly Lys Gly Leu Glu Trp
        35                  40                  45

Ile Gly Tyr Ile Gly Tyr Asp Gly Ser Asn Asn Tyr Asn Pro Ser Leu
    50                  55                  60

Lys Asn Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Asp Tyr Tyr Ser Gly Tyr Phe Asp Ser Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 70
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 70

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asn Val Gly Thr Tyr
            20                  25                  30

Val Ala Trp Tyr Gln Gln Lys Pro Gly Gln Ala Pro Arg Pro Leu Ile
            35                  40                  45

Tyr Ser Thr Ser Tyr Arg Tyr Ser Gly Ile Pro Ala Arg Phe Ser Gly
            50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys His Gln Tyr Asp Thr Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 71
<211> LENGTH: 223
<212> TYPE: PRT
<213> ORGANISM: Homo sapiens
```

<400> SEQUENCE: 71

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
    210                 215                 220
```

<210> SEQ ID NO 72
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 72

```
Tyr Ala Ser Pro Gly Lys Ala Thr Glu
1               5
```

<210> SEQ ID NO 73
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 73

```
Tyr Ala Ser Ala Gly Lys Ala Thr Glu
1               5
```

<210> SEQ ID NO 74
<211> LENGTH: 9
<212> TYPE: PRT
<213> ORGANISM: Artificial sequence
<220> FEATURE:
<223> OTHER INFORMATION: Synthetic polypeptide

```
<400> SEQUENCE: 74

Tyr Ala Ser Pro Ala Lys Ala Thr Glu
1               5

<210> SEQ ID NO 75
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 75

Tyr Ala Ser Pro Gly Ala Ala Thr Glu
1               5

<210> SEQ ID NO 76
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 76

Tyr Ala Ser Pro Gly Lys Ala Ala Glu
1               5
```